US008318795B2

(12) United States Patent
Yu et al.

(10) Patent No.: US 8,318,795 B2
(45) Date of Patent: Nov. 27, 2012

(54) ANTIOXIDANT POLYMERS CONTAINING [1,2]-DITHIOLANE MOIETIES AND USES THEREOF

(75) Inventors: John S. Yu, Los Angeles, CA (US); Bong Seop Lee, Torrance, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 461 days.

(21) Appl. No.: 12/528,067

(22) PCT Filed: Feb. 29, 2008

(86) PCT No.: PCT/US2008/055465
§ 371 (c)(1),
(2), (4) Date: Aug. 20, 2009

(87) PCT Pub. No.: WO2008/106640
PCT Pub. Date: Sep. 4, 2008

(65) Prior Publication Data
US 2010/0098653 A1 Apr. 22, 2010

Related U.S. Application Data

(60) Provisional application No. 60/892,360, filed on Mar. 1, 2007, provisional application No. 60/892,370, filed on Mar. 1, 2007, provisional application No. 60/892,376, filed on Mar. 1, 2007, provisional application No. 60/892,383, filed on Mar. 1, 2007.

(51) Int. Cl.
*A61K 31/385* (2006.01)
*C07D 339/04* (2006.01)

(52) U.S. Cl. .......................... 514/442; 549/38
(58) Field of Classification Search .................. 514/442; 549/38
See application file for complete search history.

(56) References Cited

U.S. PATENT DOCUMENTS

| | | | |
|---|---|---|---|
| 3,963,771 A | 6/1976 | Robson et al. |
| 5,122,526 A | 6/1992 | Wall et al. |
| 5,543,158 A | 8/1996 | Gref et al. |
| 5,962,520 A | 10/1999 | Smith et al. |
| 6,013,663 A | 1/2000 | Fujita et al. |
| 6,090,842 A | 7/2000 | Packer et al. |
| 6,117,899 A | 9/2000 | Wessel et al. |
| 6,127,394 A | 10/2000 | Pershadsingh et al. |
| 6,150,358 A | 11/2000 | Goldstein et al. |
| 6,204,288 B1 | 3/2001 | Pershadsingh et al. |
| 6,235,772 B1 | 5/2001 | Packer et al. |
| 6,288,106 B1 | 9/2001 | Pearson et al. |
| 6,353,011 B1 | 3/2002 | Pershadsingh et al. |
| 6,369,098 B1 | 4/2002 | Pershadsingh et al. |
| 6,380,405 B1 | 4/2002 | Ekwuribe et al. |
| 6,387,945 B2 | 5/2002 | Packer et al. |
| 6,605,637 B1 | 8/2003 | Harnett et al. |
| 6,629,995 B1 | 10/2003 | Wrenn et al. |
| 6,664,287 B2 | 12/2003 | Avery et al. |
| 6,878,374 B2 | 4/2005 | Yu et al. |
| 6,887,891 B2 | 5/2005 | Harnett et al. |
| 6,900,338 B1 | 5/2005 | Haj-Yehia |
| 6,936,715 B2 | 8/2005 | Harnett et al. |
| 6,998,115 B2 | 2/2006 | Langer et al. |
| 7,048,925 B2 | 5/2006 | Van et al. |
| 7,056,901 B2 | 6/2006 | Frechet et al. |
| 7,157,444 B2 | 1/2007 | Nelson |
| 7,220,414 B2 | 5/2007 | Brocchini et al. |
| 2004/0053989 A1 | 3/2004 | Prendergast et al. |
| 2005/0065194 A1 | 3/2005 | Shankar et al. |
| 2006/0013882 A1 | 1/2006 | Kohn et al. |
| 2007/0208134 A1 | 9/2007 | Hunter et al. |
| 2007/0281047 A1 | 12/2007 | Henry et al. |
| 2010/0291222 A1 | 11/2010 | Yu |
| 2011/0086073 A1 | 4/2011 | Yu |
| 2011/0300187 A1 | 12/2011 | Yu et al. |

FOREIGN PATENT DOCUMENTS

| | | |
|---|---|---|
| EP | 2125775 | 12/2009 |
| JP | 2010-520333 | 6/2010 |
| WO | 9743274 A1 | 11/1997 |
| WO | 9801440 A2 | 1/1998 |
| WO | WO 99/38881 | 8/1999 |
| WO | WO 01/29221 | 4/2001 |
| WO | WO 01/153312 | 7/2001 |
| WO | WO 02/46465 A3 | 6/2002 |
| WO | WO 2008/106640 A1 | 9/2008 |
| WO | 2009/086547 A1 | 7/2009 |
| WO | WO 2009/148698 A1 | 12/2009 |
| WO | WO 2010/060098 A1 | 5/2010 |

OTHER PUBLICATIONS

Schotte et al., Biochem. Pharm. (1962), vol. 11, pp. 445-461.*
Hsu et al., Proceed. ERDEC Sci. Conf. Clin. Biol. Defense Res., Aberdeen Proving Ground, MD, US, Nov. 17-20, 1998 (1999), pp. 149-153.*
International Preliminary Report on Patentability mailed Jul. 15, 2010 for PCT/US2008/088541.
International Preliminary Report on Patentability dated Sep. 1, 2009 for PCT/US2008/055465.
European publication No. 2125775 published Dec. 2, 2009, abstract corresponds to WO/2008/106640.
International PCT Search Report and Written Opinion dated Feb. 27, 2009 for PCT/US2008/088541.
International PCT Search Report and Written Opinion dated Jun. 10, 2009 for PCT/US2009/039956.
International Preliminary Report on Patentability dated Dec. 6, 2010 for PCT/US2009/039956.
International PCT Search Report and Written Opinion dated Jan. 21, 2010 for PCT/US2009/065776.

(Continued)

*Primary Examiner* — Taofiq A Solola
(74) *Attorney, Agent, or Firm* — Linda B. Huber; Nixon Peabody LLP

(57) ABSTRACT

The present invention describes polymers containing 1,2-dithiolanes capable of acting as scavengers of free radicals, metals and reactive oxygen species. Also described are methods of synthesizing the antioxidant 1,2-dithiolane derivatives and polymerization thereof to produce biodegradable antioxidant polymers. The antioxidant polymers of the present invention may be used to treat diseases or conditions caused by oxidative stress and other free radical mediated conditions. The antioxidant polymers may also be used for the preparation of antioxidant particulate delivery devices of therapeutic agents.

72 Claims, 2 Drawing Sheets

OTHER PUBLICATIONS

International Preliminary Report on Patentability dated May 24, 2011 for PCT/US2009/065776.

Van Regenmortel, Marc H.V., Mapping epitope structure and activity: from one-dimensional prediction to four-dimensional description of antigenic specifity, Methods: A Companion to Methods in Enzymology 9, (1996), pp. 465-472.

Abaza et al., Effects of amino acid substitutions outside and antigenic site on protein binding to monoclonal antibodies of predetermined specificity obtained by peptide immunization: demonstration with region 94-100 (antigenic site 3) of myoglobin, Journal of Protein Chemistry, vol. 11, No. 5, 1992, pp. 433-444.

Colman, P.M., Effects of amino acid sequence changes on antibody-antigen interactions, Biomolecular Research Institute, 343 Royale Parade, Parkville, 3052 (Australia), Research in Immunology, No. 1, vol. 145, 1994, pp. 33-35.

Di Stefano, et al., Antiparkinson Prodrugs, Molecules, Jan. 16, 2008, vol. 13, pp. 46-68.

Lederman et al., A single amino acid substitution in a common african allele of the CD4 molecule ablates binding of the monoclonal antibody, OKT4, Molecur Immunology, vol. 28, No. 11, pp. 1171-1181, 1991.

European Application No. 08731097.5 Extended Search Report dated Jun. 15, 2011.

Casolaro et al. Redox-active Polymers: Sythesis and Exchange Reaction of Amino Compounds Containing a Cyclic Disulfide. Polymer (1994). 35(2): pp. 360-366.

Fujimoto et al. Synthesis of a Polymer Containing the Cyclic Disulfide (1, 2-Dithiolane) Structure. Die Makromolekulare Chemie (1974). 175: pp. 3597-3602.

Sieczkowska et al. Sythesis and Characterization of Photolabile Aminoterpolymers for Covalent Attachment onto Gold Substrates. Designed Monomers and Polymers (2005). 8(6): pp. 629-644.

Sun et al. Ultrathin Self-Assembled Polymeric Films on Solid Surfaces. I. Synthesis and Characterization of Acrylate Copolymers Containing Alkyl Disulfide Side Chains. Journal of Polymer Science: Part A: Polymer Chemistry. (1993). 31: pp. 1729-1740.

Sun et al. Ultrathin Self-Assembled Polymeric Films on Solid Surfaces. III. Influence of Acrylate Dithioalkyl Side Chain Length on Polymeric Monolayer Formation of Gold. J. Vac. Sci. Technol. A (1994). 12(4): pp. 2499-2506.

Japanese Application No. 2009-551871 Official Action dated Dec. 21, 2011.

Rice et al. Inhibition of multiple phases of human immunodeficiency virus type 1 replication by a dithiane compound that attacks the conserved zinc fingers of retroviral nucleocapsid proteins. Antimicrob Agents Chemother. (1997). 41 (2): pp. 419-426.

Kalyuzhny et al. Ligand effects on optical properties of CdSe nanocrystals. Journal of Physical Chemistry B. (2005). 109(15): pp. 7012-7021. Abstract.

Kieller et al. The Five-membered Disulfide Ring System. III. Antineoplastic Potentialities. Acta Biochimica Polonica (1964). 11(2-3): pp. 279-291.

Lee et al. Nereistoxin and Cartap Neurotoxicity Attributable to Direct Block of the Insect Nicotinic Receptor/Channel. Journal of Agricultrual and Food Chemistry. (2003). 51(9): pp. 2646-2652. Abstract.

Povalyaeva et al. Synthesis and Properties of N-substituted 4-amino-1,2, dithiolanes and Related Compounds. Zhurnal Organicheskoi Khimii. (2004). 20(4): pp. 849-860.

Thomas et al. Campthotecin: Current Perspectives. Bioorg Med Chem. (2004): 12: pp. 1585-1604. Abstract.

U.S. Appl. No. 12/995,125 Restriction Requirement dated Jun. 7, 2012.

U.S. Appl. No. 13/114,539 Restriction Requirement dated May 25, 2012.

* cited by examiner

ANTIOXIDANT POLYMERS CONTAINING [1,2]-DITHIOLANE MOIETIES AND USES THEREOF

This application is the National Phase of International Application PCT/US08/55465, filed Feb. 29, 2008, which designated the U.S. and that International Application was published under PCT Article 21(2) in English. This application also includes a claim of priority under 35 U.S.C. §119(e) to U.S. provisional patent application Nos. 60/892,360, filed Mar. 1, 2007, 60/892,370, filed Mar. 1, 2007, 60/892,376, filed Mar. 1, 2007, and 60/892,383, filed Mar. 1, 2007.

FIELD OF INVENTION

The present invention relates to dithiolane derivatives and antioxidant polymers containing dithiolane moieties that are capable of acting as scavengers of free radicals, metals and reactive oxygen species (ROS) and/or are capable of allowing the regeneration of endogenous antioxidants or entities which trap the ROS.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Molecules containing a dithiolane moiety are widely investigated due to their antioxidant properties. α-Lipoic acid (thioctic acid, 1,2-dithiolane-3-pentanoic acid), which has a dithiolane ring in its molecule, is a widely distributed natural substance which was originally discovered as a growth factor. Physiologically, it acts as a coenzyme of the oxidative decarboxylation of α-keto carboxylic acid (e.g., pyruvates) and as an antioxidant, and it is able to regenerate vitamin C, vitamin E, glutathione and coenzyme Q10. In pathological conditions, lipoic acid is applied in the treatment of diabetic polyneuropathy, liver cirrhosis and metal intoxications.

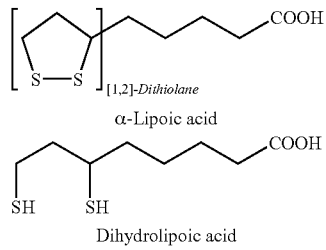

Lipoic acid and dihydrolipoic acid are capable of trapping a number of radicals both in a lipid and in an aqueous environment. Lipoic acid and dihydrolipoic acid act as antioxidants not only by direct radical trapping and/or metal chelation but also by recycling other antioxidants (e.g., vitamin C, vitamin E) and by reducing glutathione, which in turn recycles vitamin E. The two thiol groups present in the [1,2]-dithiolane ring system confer upon it a unique antioxidant potential. The disulfides with a cyclic five-member ring such as lipoic acid have been found to be more effective in reductive and/or nucleophilic attack than open-chain derivatives such as cystine or glutathione.

The antioxidant potential of a compound may be evaluated based on the properties such as (1) specificity of free radical scavenging, (2) interaction with other antioxidants, (3) metal-chelating activity, (4) effects on gene expression, (5) absorption and bioavailability, (6) location (in aqueous or membrane domains, or both), and (7) ability to repair oxidative damage (Packer et al., FREE RADICAL BIOLOGY & MEDICINE. 19(2):227-250, 1995). According to the above criteria, the [1,2]-dithiolane containing lipoic acid/dihydrolipoic acid redox system has been regarded as a universal antioxidant.

There have been many attempts to develop lipoic acid derivatives or complexes having antioxidant activity. U.S. Pat. Nos. 6,090,842; 6,013,663; 6,117,899; 6,127,394; 6,150,358; 6,204,288, 6,235,772; 6,288,106; 6,353,011; 6,369,098; 6,387,945; 6,605,637; 6,887,891; 6,900,338; and 6,936,715 are some examples.

In many other U.S. patents, the natural and synthetic lipoic acid derivatives and their metabolites are disclosed for use in preventing skin aging and in the treatment of free radical mediated diseases, including inflammatory, proliferative, neurodegenerative, metabolic and infectious diseases.

Inhibitory Activity on NO-Synthase and Trapping the Reactive Oxygen Species (ROS)

Various conditions or disease conditions have demonstrated a potential role of nitric oxide (NO) and the ROS's and the metabolism of glutathione in their physiopathology. Conditions or disease conditions where nitrogen monoxide and the metabolism of glutathione as well as the redox status of thiol groups are involved include but are not limited to: cardiovascular and cerebrovascular disorders (e.g., atherosclerosis, migraine, arterial hypertension, septic shock, ischemic or hemorrhagic cardiac or cerebral infarctions, ischemias and thromboses); disorders of the central or peripheral nervous system (e.g., neurodegenerative nervous system); neurodegenerative diseases including cerebral infarctions, sub-arachnoid hemorrhaging, aging, senile dementias (e.g., Alzheimer's disease), Huntington's chorea, Parkinson's disease, prion disease (e.g., Creutzfeld Jacob disease), amyotrophic lateral sclerosis, pain, cerebral and spinal cord traumas, addiction to opiates, alcohol and addictive substances, erective and reproductive disorders, cognitive disorders, encephalopathies, encephalopathies of viral or toxic origin, depression, anxiety, schizophrenia, epilepsy, sleeping disorders, eating disorders (e.g., anorexia, bulimia); disorders of the skeletal muscle and neuromuscular joints (e.g., myopathy, myositis), cutaneous diseases; proliferative and inflammatory diseases (e.g., atherosclerosis), pulmonary hypertension, respiratory distress, glomerulonephritis, cataracts, portal hypertension, psoriasis and rheumatoid arthritis, fibroses, amyloidoses, inflammations of the gastro-intestinal system (e.g., colitis, Crohn's disease) or of the pulmonary system and airways (e.g., asthma, sinusitis, rhinitis) as well as contact or delayed hypersensitivities; organ transplantation; auto-immune and viral diseases (e.g., lupus, AIDS, parasitic and viral infections), diabetes and its complications (e.g., retinopathies, nephropathies and polyneuropathies, multiple sclerosis, myopathies); cancer; autosomal genetic diseases (e.g., Unverricht-Lundborg disease); neurological diseases associated with intoxications (e.g., cadmium poisoning, inhalation of n-hexane, pesticides, herbicides), associated with treatments (e.g., radiotherapy) or disorders of genetic origin (e.g., Wilson's disease); and impotence linked to diabetes.

These conditions and disease conditions are characterized by an excessive production or a dysfunction of nitrogen monoxide and/or the metabolism of glutathione and of the redox status of the thiol groups (Duncan and Heales, *Nitric Oxide And Neurological Disorders*, MOLECULAR ASPECTS OF MEDICINE. 26:67-96, 2005; Kerwin et al., *Nitric Oxide: A New Paradigm For Second Messengers*, J. MED. CHEM. 38:4343-4362, 1995; Packer et al., FREE RADICAL BIOLOGY & MEDICINE. 19:227-250, 1995). U.S. Pat. Nos. 6,605,637, 6,887,891, and 6,936,715 disclose that lipoic acid derivatives inhibit the activity of NO-synthase enzymes producing nitrogen monoxide NO and regenerate endogenous antioxidants which trap the ROS and which intervene in a more general fashion in the redox status of thiol groups. U.S. Pat. Nos. 5,693,664, 5,948,810, and 6,884,420 disclose the use of racemic α-lipoic acid or their metabolites, salts, amides or esters for the synthesis of drugs for the treatment of diabetes mellitus of types I and II. U.S. Pat. No. 5,925,668 discloses a method of treating free radical mediated diseases, and/or reducing the symptoms associated with such diseases whereby the compounds with antioxidant activity contain 1,2-dithiolane, reduced or oxidized forms. U.S. Pat. No. 6,251,935 discloses methods for the prevention or treatment of migraine comprising the administration of an active ingredient selected from the group consisting of racemic alpha-lipoic acid, enantiomers and pharmaceutically acceptable salts, amides, esters or thioesters thereof. U.S. Pat. Nos. 6,472,432 and 6,586,472 disclose the treatment of a chronic inflammatory disorder, rosacea, by application of a composition containing lipoic acid and/or lipoic acid derivatives. There is also strong evidence that the neuroprotective effects of lipoic acid and dihydrolipoic acid are mediated by antioxidant and free radical scavenging mechanisms (Packer et al., FREE RADICAL BIOLOGY & MEDICINE. 22:359-378, 1997).

Topical Application and Cosmetic Preparation

Ultraviolet light can produce reactive oxygen species (ROS) that damage the skin leading to the premature aging of the skin. ROS are a collection of reactive free radicals produced from the oxygen molecules, including singlet oxygen, the superoxide radical, hydrogen peroxide, and the hydroxyl radical, as well as the reaction products produced by these free radicals. These ROS react with other molecules and generate a cascade of harmful free radical reactions in the skin.

U.S. Pat. Nos. 5,709,868 and 6,752,999 disclose methods for the prevention and/or treatment of skin damage, particularly inflammation and aging whereby a composition containing lipoic acid/or lipoic acid derivatives are topically applied to affected skin areas. U.S. Pat. Nos. 5,965,618 and 6,955,816 disclose compositions and methods for the treatment and inhibition of scar tissue based on topical application of compositions containing lipoic acid and/or lipoic acid derivatives to scars and to injured skin sites. U.S. Pat. No. 6,365,623 discloses the treatment of active acne and acneiform scars by topical application of a composition containing lipoic acid and/or a lipoic acid derivative.

Cancer Therapy

U.S. Pat. Nos. 5,035,878 and 5,294,430 disclose that dithiocarbamates, which have antioxidant properties, can reverse the damage to the blood-forming function of the bone marrow (myelesuppression) caused by treatment with antineoplastic agents. U.S. Pat. Nos. 6,284,786, 6,448,287, and 6,951,887 disclose methods of cancer therapy using lipoic acid as a therapeutic agent administered in combination with ascorbic acid. U.S. Pat. No. 7,071,158 discloses that antioxidants increase the cytotoxicity of antineoplastic agents to abnormally proliferating cells and decrease the toxicity of antineoplastic agents to normal cells.

However, many of the currently available oral formulations have a low bioavailability due to incomplete absorption and first-pass metabolism. Rapid degradation of antioxidants in the body fluid and elimination of antioxidants from the body further decreases the beneficial effects of antioxidants. Further, some antioxidants may be limited by their stoichiometric quantities; for example it has been postulated that antioxidant potency of vitamins such as C and E is limited because they work as scavengers of existing excess reactive species. (Johanse et al. *Oxidative stress and the use of antioxidants in diabetes: Linking basic science to clinical practice*, CARDIOVASCULAR DIABETOLOGY. 4:5, 2005) Thus, there is a need in the art to overcome one or more of these limitations. There is also a need for useful compounds for the treatment of conditions or disease conditions wherein the potential role of NO and the ROS's and the metabolism of glutathione has been demonstrated in their physiopathology. The inventive [1,2]-dithiolane derivatives, oligomers and/or polymers thereof described herein may be useful for such treatments. The inventive [1,2]-dithiolane derivatives and oligomers and/or polymers thereof may be useful for to treat or delay the onset of conditions and disease conditions caused by oxidative damage (e.g., skin aging, wrinkle formation), for the protection of skin from damage caused by ultraviolet radiation and dessication, and for cancer therapy. The inventive polymers that are sensitive to an acidic environment enable the rate of erosion to be associated with the rate of release of a therapeutic agent, which may be controlled by their molecular structures.

BRIEF DESCRIPTION OF THE FIGURE

Exemplary embodiments are illustrated in referenced FIGURE. It is intended that the embodiments and FIGURE disclosed herein are to be considered illustrative rather than restrictive.

DESCRIPTION OF THE INVENTION

Figure 1A:
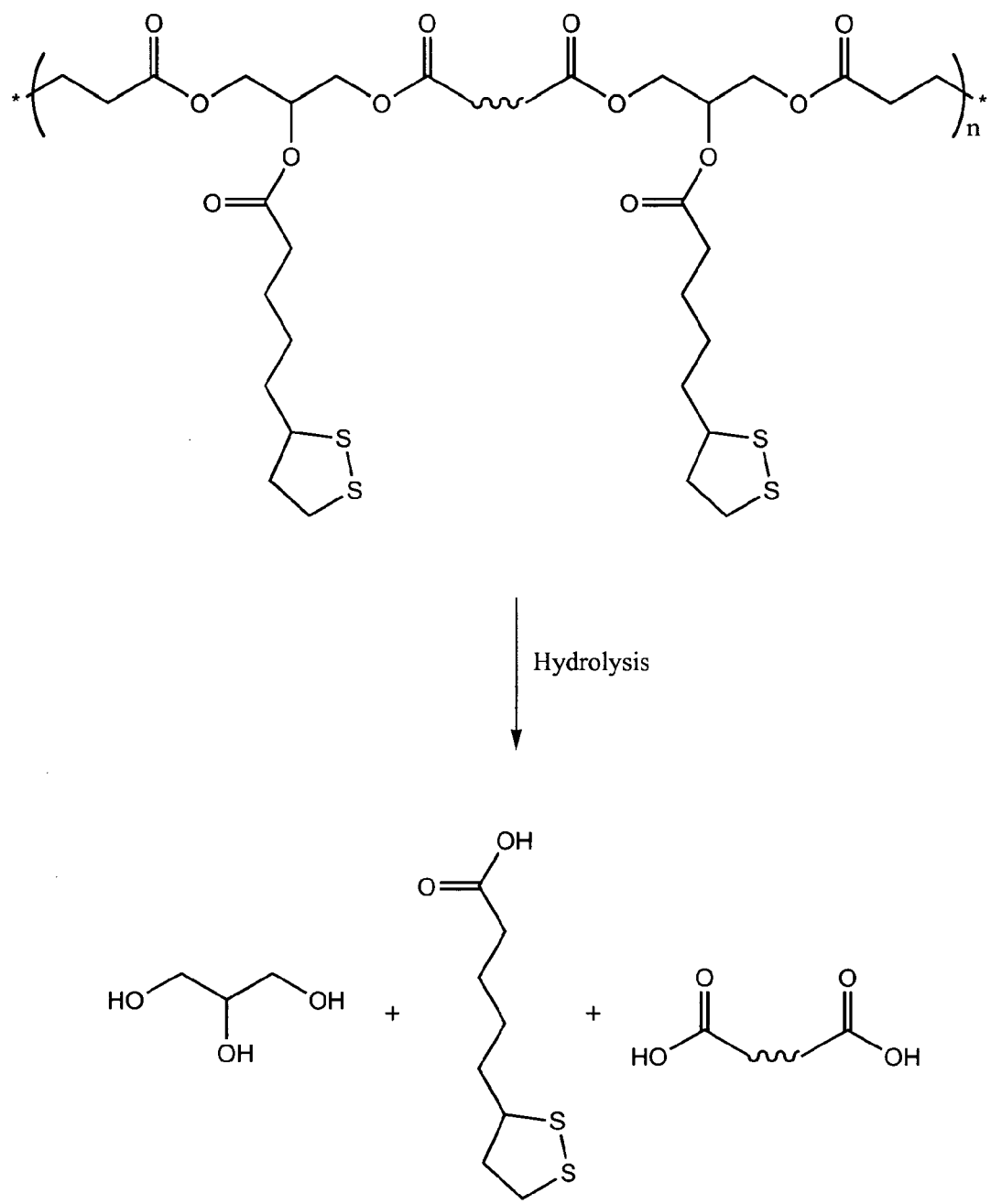
FIG. 1A and FIG. 1B depict hydrolytic degradation of polymers in accordance with various embodiments of the present invention.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

The contents of U.S. Provisional Application Ser. Nos. 60/892,360 60/892,370, 60/892,376, and 60/892,383, all filed on Mar. 1, 2007, are herein incorporated by reference in their entirety as though fully set forth.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Conditions" and "disease conditions," as used herein may include, but are in no way limited to conditions or disease conditions wherein the potential role of NO, ROS's or the metabolism of glutathione have been demonstrated in their physiopathology, conditions or disease conditions caused by oxidative damage, and any form of neoplastic cell growth and proliferation, whether malignant or benign, pre-cancerous and cancerous cells and tissues.

"Pharmaceutical" and "drug," as used herein, refer to any substance used internally or externally as a medicine for the treatment, cure or prevention of a disease or disorder, even if the treatment, cure or prevention of the disease or disorder is ultimately unsuccessful.

"Polymeric antioxidant" as used herein refers to a polymer that contains a [1,2]-dithiolane moiety as a monomeric repeating unit or a polymer that contains a [1,2]-dithiolane moiety that is covalently attached to the polymer backbone, and reduces the oxidation of an oxidizable compound under physiological condition.

"Antineoplastic agents," as used herein, refer to any substance that decreases abnormal cell proliferation.

"Therapeutically effective amount" as used herein refers to that amount which is capable of achieving beneficial results in a patient with a condition or a disease condition in which treatment is sought. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease even if the treatment is ultimately unsuccessful.

"Acetal" as used herein refers to a diether in which both ether oxygen atoms are bound to the same carbon.

Various embodiments of the present invention provide for antioxidant polymers that contain [1,2]-dithiolane moieties. In one embodiment, the antioxidant polymers of the present invention are capable of acting as scavengers of free radicals. In another embodiment, the antioxidant polymers of the present invention are capable of serving as a vehicle for the delivery of pharmaceutical and biological therapies.

In one embodiment, the present invention provides for an antioxidant [1,2]-dithiolane derivative. In another embodiment, the present invention provides for an oligomer comprising two or more antioxidant [1,2]-dithiolane derivative. In another embodiment, the present invention provides for a polymer comprising antioxidant [1,2]-dithiolane derivatives. The [1,2]-dithiolane derivative, oligomer thereof or polymer thereof may be biodegradable.

Additional embodiments of the present invention provide for methods of synthesizing the antioxidant polymers of the present invention.

Further embodiments of the present invention provide for methods of using the antioxidant polymers of the present invention. In one embodiment, the antioxidant polymers are used for treating conditions or disease conditions that are caused by oxidative stress or other free radical mediated diseases or disease conditions.

In a particular embodiment, the antioxidant polymer is used to treat skin inflammation or aging mediated by free radicals. The method comprises providing a composition comprising a [1,2]-dithiolane derivative, an oligomer thereof, a polymer thereof, or combinations thereof, and administering to skin areas in need of treatment a therapeutically effective amount of the composition. In one embodiment, the composition further comprises a pharmaceutically acceptable or dermatologically acceptable carrier.

In another embodiment, the antioxidant polymers are used in the preparation of antioxidant particulate delivery vehicles for therapeutic agents. In a particular embodiment, the antioxidant polymers are used as a gene delivery vehicle to carry and deliver genetic material to a subject. The genetic material may be DNA or RNA. The antioxidant polymers may also be used as a carrier for peptides or proteins; for example, for use in vaccination therapies.

In another embodiment, the antioxidant polymer may be used as a carrier of a therapeutic agent. In one embodiment, the therapeutic agent is a chemotherapeutic agent that is useful for cancer treatment.

Another embodiment of the present invention provides for a method to enhance the cytotoxicity of an antineoplastic drug for treatment of a disorder of abnormal cell proliferation. The method comprises providing a composition comprising a [1,2]-dithiolane derivative, an oligomer thereof, a polymer thereof or combinations thereof; administering a therapeutically effective amount of the antineoplastic drug to a subject in need of the treatment; and administering a therapeutically effective amount of the composition. In one embodiment, the antineoplastic drug is encapsulated within the composition. Antineoplastic drugs are known to one skilled in the art. Examples include but are not limited to, paclitaxel, camptothecin, oxaliplatin and temozolomide.

Polymers as Macromolecular Antioxidant

One aspect of this invention relates to the syntheses and uses of compounds containing dithiolane rings as monomers that are polymerized into biodegradable antioxidant polymers. The monomers may be polymerized via biodegradable ester bond or acetal bond, which are susceptible to hydrolytic degradation. Upon variation of the monomers, polymers with varying hydrophobicity may be prepared. Water-soluble polymers may be used as the macromolecular antioxidant component of injectable pharmaceutical formulations. Hydrophobic polymers may be used for the preparation of antioxidant nanoparticles or microparticles that, upon administration, circulate through the body for a prolonged period of time and thus provide controlled, sustained release of the small molecular antioxidants. These antioxidants may be delivered to areas of the body including but not limited to tissue, brain, and cell.

Polymers as Delivery Devices

The biodegradable antioxidant polymers of the present invention may be used as pharmaceutical and/or drug delivery vehicles to deliver small molecules, peptides, oligonucleotides, polynucleotides, proteins, antigens, chemotherapeutics, and the like, to tissues, organs, and cells.

The inventive antioxidant polymers comprise multiple [1,2]-dithiolane groups with universal antioxidant properties. In one embodiment, the polymer is degraded under in vivo conditions over a suitable time period and the encapsulated, embedded and/or covalently attached pharmaceutical and/or drug is released from the particulate polymer carriers to provide a therapeutic effect. The polymer itself is also degraded in vivo to provide its own therapeutic benefits.

Antioxidant Polymers as Antineoplastic Drug

It has been discovered that antioxidants induce cell cycle arrest, and are thus useful to enhance the efficacy of antineoplastic drugs for the treatment of abnormal cell proliferation. It has been also discovered that antioxidants not only increase the cytotoxicity of antineoplastic agents to abnormally proliferating cells, but they also decrease the toxicity of antineoplastic agents to normal cells (see, e.g., U.S. Pat. Nos. 5,035, 878 and 5,294,430).

One of skill in the art will readily appreciate that polymers larger than about 40,000 Daltons accumulate selectively in the tumor site due to the enhanced permeability and retention ("EPR") effect (Maeda et al., J. CONTROLLED RELEASE 65, 271, 2000). Therefore, the present invention also provides methods to decrease the toxicity of an antineoplastic agent administered for the treatment of abnormally proliferating cells and/or to decrease the toxicity of antineoplastic agents to normal cells. The methods may comprise administering the inventive antioxidant [1,2]-dithiolane derivatives, oligomers or polymers thereof prior to, with, or following the antineoplastic treatment, as well as methods for administering the inventive antioxidant [1,2]-dithiolane derivatives, oligomers or polymers thereof to a subject in need thereof.

One aspect of this invention relates to the syntheses of antioxidant [1,2]-dithiolane derivatives and uses of these compounds as monomers that are polymerized into biodegradable antioxidant polyacetals and polyesters. Another aspect of this invention relates to the syntheses of antioxidant polymers by covalent attachment of the antioxidant [1,2]-dithiolane derivatives to diverse functional polymers including, but not limited to, polycarboxylic acid, polysaccharides, polyamines, polyols and dendritic polymers.

Polymerization of the Antioxidant [1,2]-dithiolane Derivatives to Polyacetals and Polyesters One embodiment of the present invention is directed to methods of making degradable antioxidant polyacetals and polyesters. Polyacetals are polymers that contain recurring acetal bonds and polyesters are polymers that contain recurring ester bonds. Hydrolytically degradable polymers containing acetal bonds have been reported (Tomlinson et al., MACROMOLECULES. 35:473-480, 2002).

Polyacetals and polyesters of the present invention may comprise a recurring unit; for example, represented by the following formulas:

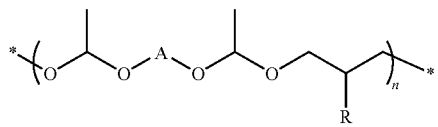

Formula 1

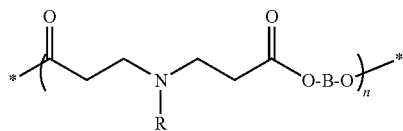

Formula 2 wherein A and B are selected from the group consisting of branched and unbranched alkyl, aryl, cycloaliphatic and aralkyl group, and is saturated or unsaturated, and may optionally contain hetero atoms, and R is selected from the antioxidant [1,2]-dithiolane derivatives described herein.

Figure 1B:
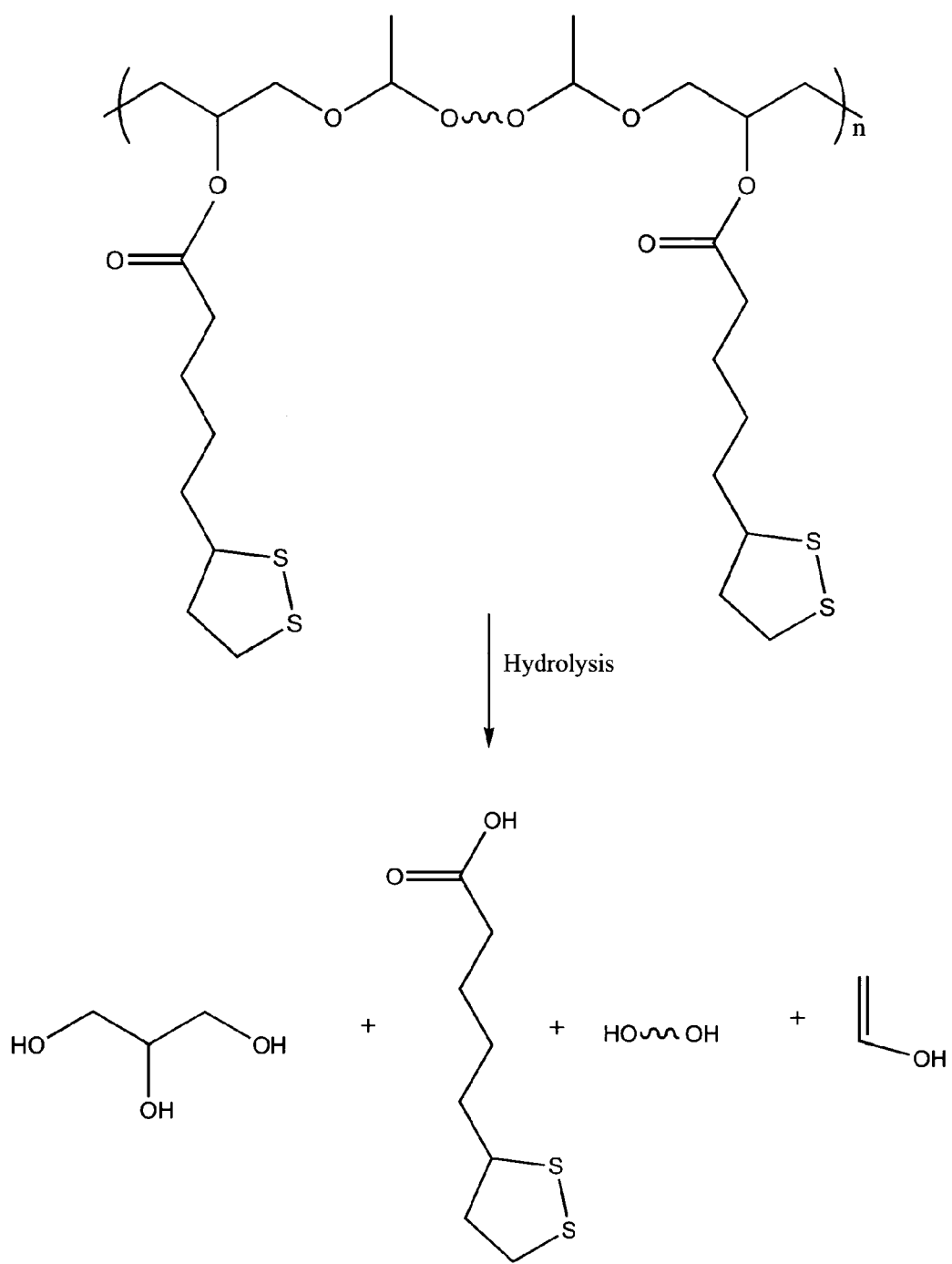

The monomers may be polymerized via biodegradable ester bond or acetal bond, which are susceptible to hydrolytic degradation (see FIGS. 1A and 1B). Upon variation of the monomers, polymers with varying hydrophobicity may be prepared. Water-soluble polymers may be used as the macromolecular antioxidant component of injectable pharmaceutical formulations. Hydrophobic polymers may be used for the preparation of antioxidant nanoparticles or microparticles that, upon administration, circulate through the body for a prolonged period of time and thus provide controlled, sustained release of the small molecular antioxidants. These antioxidants may be delivered to areas of the body including but not limited to tissue, brain, and cell.

[1,2]-Dithiolane Derivatives

In the present invention, various types of monomeric [1,2]-dithiolane derivatives are designed for the preparation of the antioxidant polyacetals and polyesters as follows:

Type I—Structures of 1,2-dithiolane(diols)

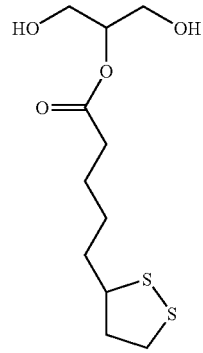

Formula 3

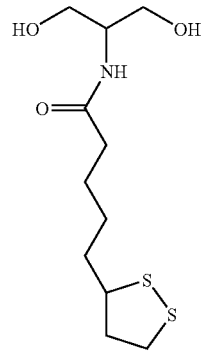

Formula 4

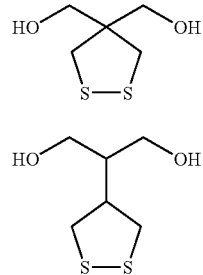

Formula 5

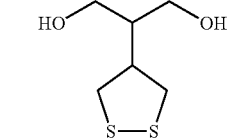

Formula 6

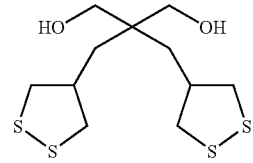

Formula 7

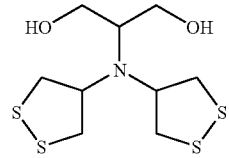

Formula 8

Formula 9

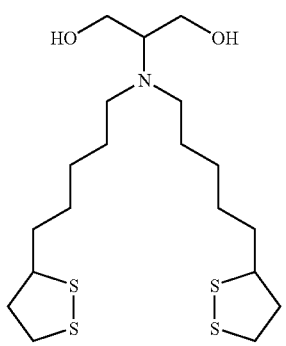

Formula 10

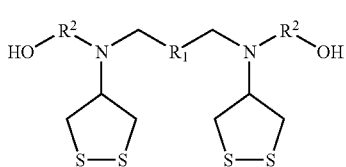

Type II—Structures of 4-(amino)-1,2-dithiolane

Formula 11

Formula 12

Formula 13

Formula 14

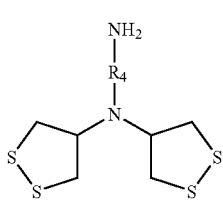

Formula 15

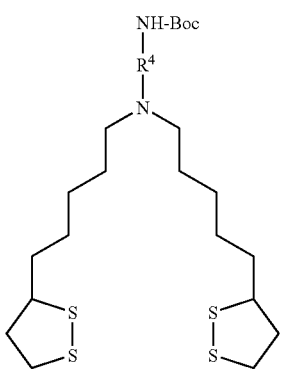

Formula 16

Formula 17

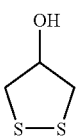

Formula 18

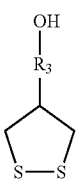

wherein $R_1$, $R_2$, $R_3$ and $R_4$ are each independently selected from the group consisting of a branched and unbranched alkyl, aryl, cycloaliphatic and aralkyl group, is saturated or unsaturated, and may optionally contain hetero atoms.

The monomeric [1,2]-dithiolane derivatives are also prepared by the conjugation of a Type I dithiolane derivative with an acryloyl chloride as follows:

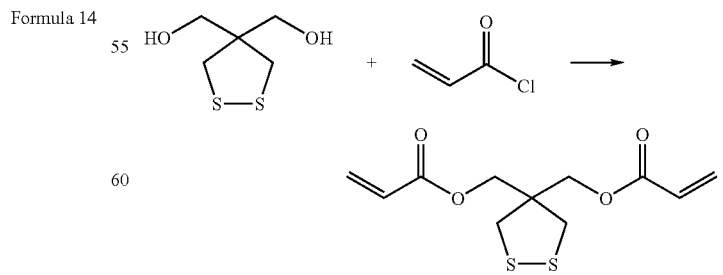

Examples of the combined monomers include compounds with the following formulas.

Type III—Structures of 1,2-dithiolane-bis(acrylate ester)

Formula 19
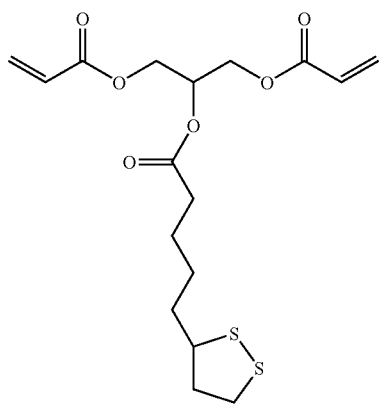

Formula 20
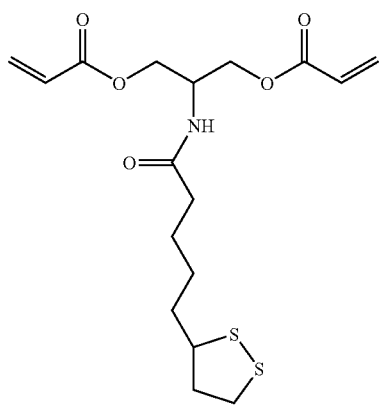

Formula 21
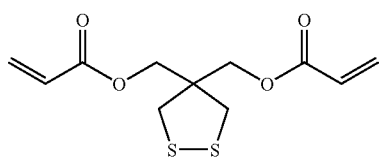

Formula 22
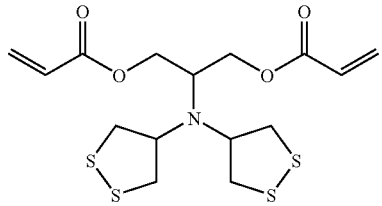

Formula 23
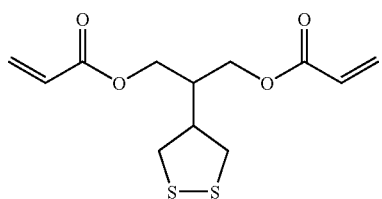

Formula 24
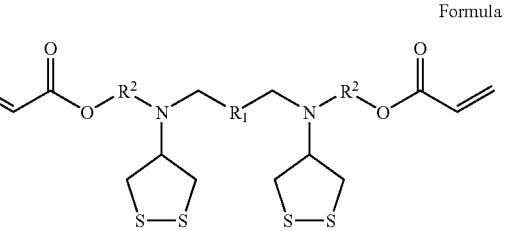

Formula 25
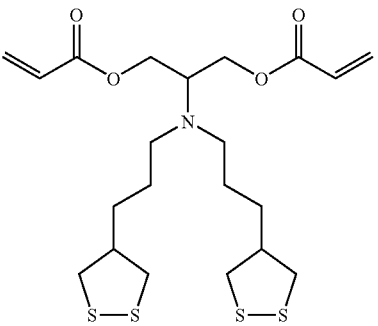

Formula 26
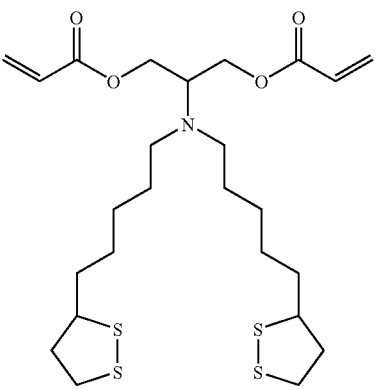

In addition to the monomeric [1,2]-dithiolane derivatives described above, the commercially available divinyl ether of Type I and II and bis(acrylate ester) may be used for which one or more [1,2]-dithiolane derivatives may be conjugated thereon. The acetals and divinyl ether serves as the polymer backbone.

Divinyl Ether Type I

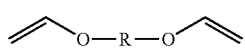

wherein the R group may be a hydrocarbon group; for example, an alkyl, aryl, cycloaliphatic or aralkyl group; and may be saturated or unsaturated. The R group may contain hetero atoms (e.g., nitrogen, oxygen, sulfur, etc.).

Divinyl Ether Type II

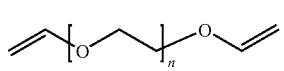

wherein n may be from 2 to 100.

Bis(acrylate ester)s

wherein B may be selected from the group consisting of a branched or unbranched alkyl, aryl, cycloaliphatic and aralkyl group, is saturated or unsaturated, and optionally contains hetero atoms.

Bis(acrylate ester) may be prepared using organic reactions well known to those of ordinary skill in the art as follows:

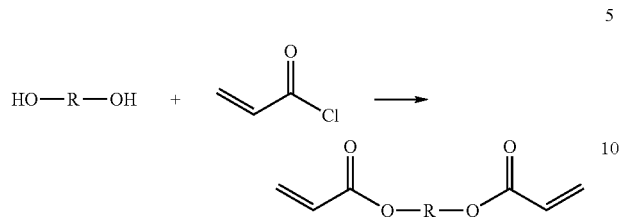

wherein R may be any of a wide variety of substituents; for example, R may be selected from the group consisting of a branched or unbranched alkyl, aryl, cycloaliphatic and aralkyl group, is saturated or unsaturated, and optionally contains hetero atoms.

Diols that are useful in the present inventive polymers include, but are not limited to commercially available one as follows:

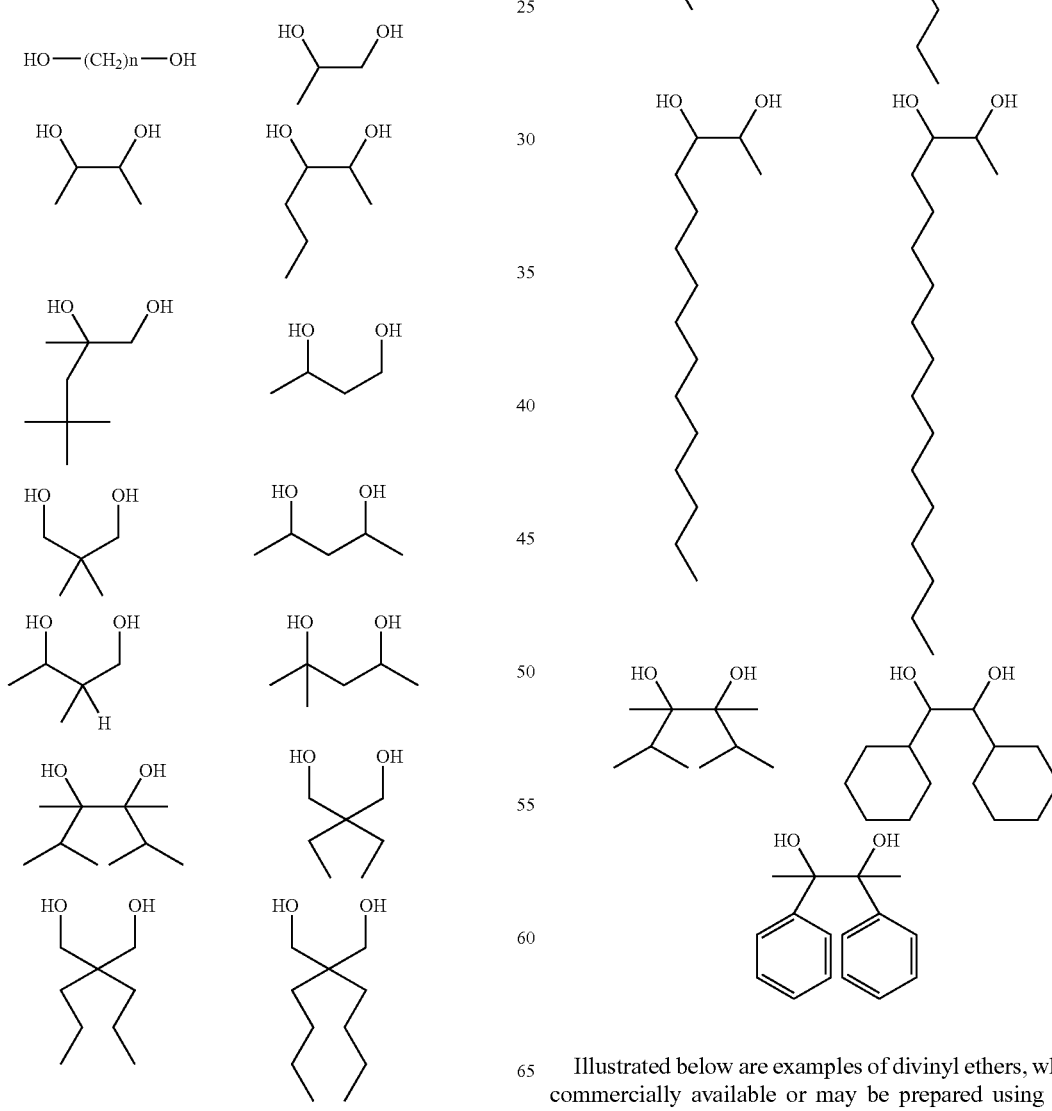

Illustrated below are examples of divinyl ethers, which are commercially available or may be prepared using organic reactions well known to those of ordinary skill in the art.

Divinyl ethers that are useful in the present inventive polymers include, but are not limited to commercially available ones as follows:

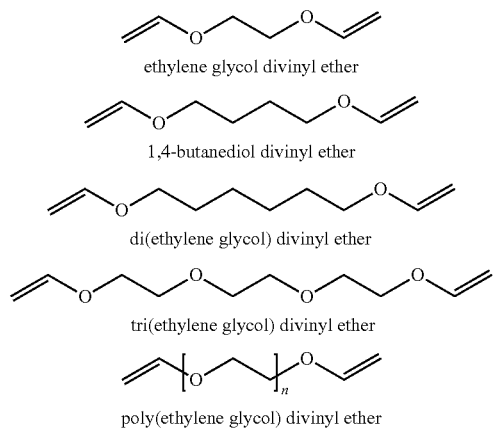

ethylene glycol divinyl ether 1,4-butanediol divinyl ether di(ethylene glycol) divinyl ether tri(ethylene glycol) divinyl ether poly(ethylene glycol) divinyl ether Bis(acrylate ester) that are useful in the present inventive polymers include, but are not limited to, commercially available diacrylates as follows:

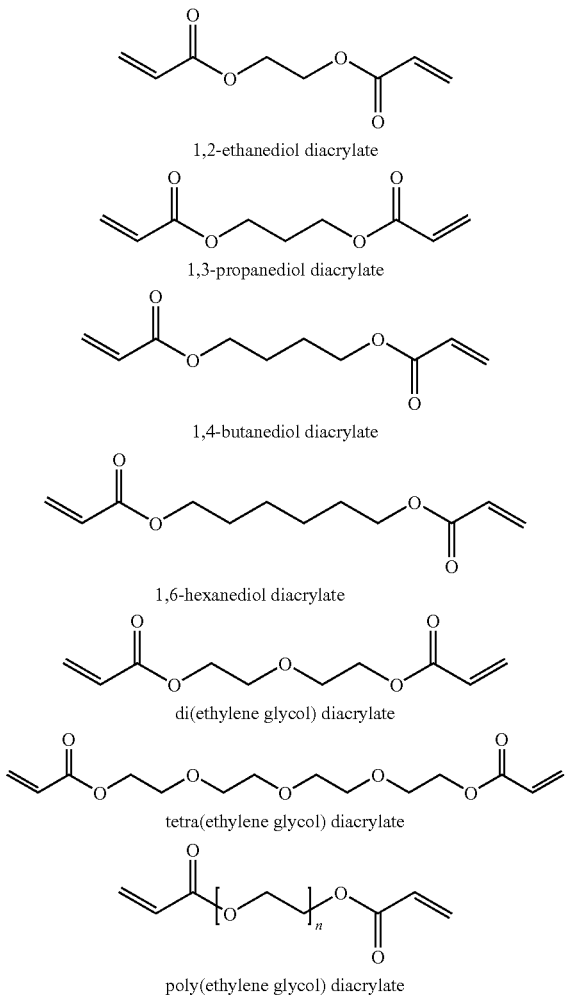

1,2-ethanediol diacrylate 1,3-propanediol diacrylate 1,4-butanediol diacrylate 1,6-hexanediol diacrylate di(ethylene glycol) diacrylate tetra(ethylene glycol) diacrylate poly(ethylene glycol) diacrylate

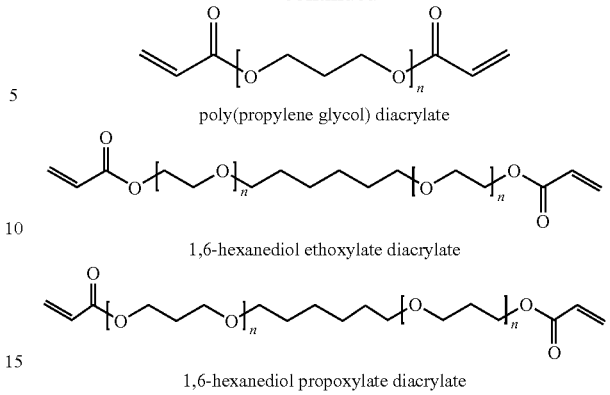

poly(propylene glycol) diacrylate 1,6-hexanediol ethoxylate diacrylate 1,6-hexanediol propoxylate diacrylate

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. One skilled in the art will also readily recognize that the reaction schemes shown herein are simplified and stoichiometric proportions will be readily determined without undue experimentation. The inventive polymers may also be prepared by any method known in the art.

Example 1

Polymer-Type I

In one embodiment, the Type I dithiolane repeating units polymerize with a divinyl ether to produce polymers as follows:

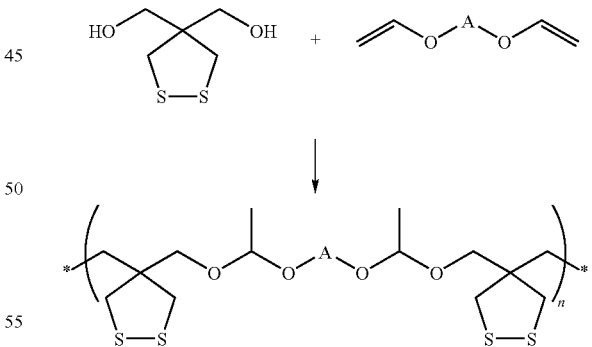

Synthesis of Polymer—Representative Polymerization in Tetrahydrofuran

A Type I [1,2]-Dithiolane monomeric unit (5 mmol, 1.0 equiv) and divinyl ether (5.2 mmol, 1.04 equiv) are mixed in tetrahydrofuran (THF) (20 mL) with molecular sieves (1.0 g, 3 Å, 10-20 mesh beads, Fluka) at room temperature. The reaction mixture is stirred for 20 min and p-toluenesulfonic acid monohydrate (TSA, 0.15 mmol, 0.03 equiv) is added.

The mixture is stirred for two days at room temperature and aqueous NaHCO$_3$ (8% w/v, 2.0 ml) is added to the reaction mixture. The organic phase is extracted with ethylacetate (3×20 mL), dried over sodium sulfate and the volume of the solvent is reduced (~20 mL) by rotary evaporation at room temperature. The organic solution is added dropwise into stirred hexane, the polyacetal is collected and placed into a fresh solution of hexane and stirred for an additional 10 min. The polyacetal is again collected and then dried in a vacuum at room temperature for 4 hours to give the polymer.

Examples of polymers in these embodiments include but are not limited to the following:

Formula 27

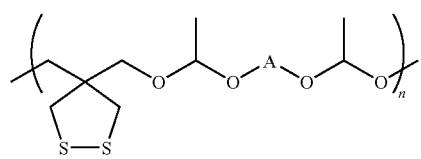

Formula 28

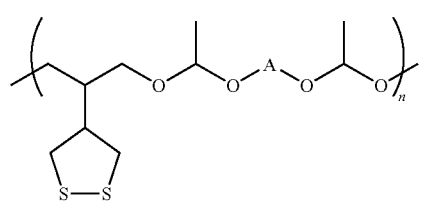

Formula 29

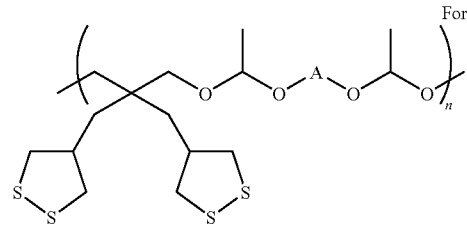

Formula 31

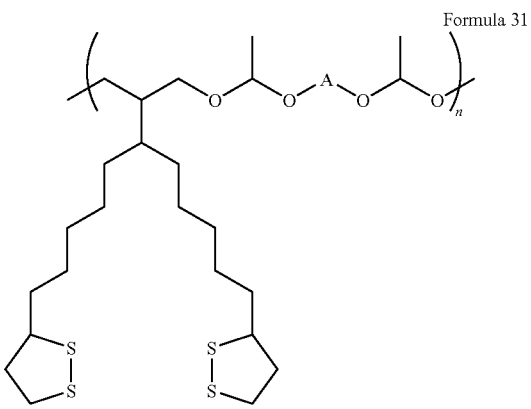

wherein A is selected from the group consisting of branched or unbranched alkyl, aryl, cycloaliphatic and aralkyl group, is saturated or unsaturated, and may optionally contain hetero atoms.

In particular embodiments A is selected from the group consisting of —CH$_2$CH$_2$—, —CH$_2$CH$_2$CH$_2$CH$_2$—, —CH$_2$CH$_2$CH$_2$CH$_2$CH$_2$CH$_2$—, —CH$_2$CH$_2$OCH$_2$CH$_2$—, and —CH$_2$CH$_2$OCH$_2$CH$_2$OCH$_2$CH$_2$—.

Example 2

Polymer-Type II

In another embodiment, a Type II dithiolane repeating unit polymerizes with a bis(acrylate ester) to produce polymers as follows:

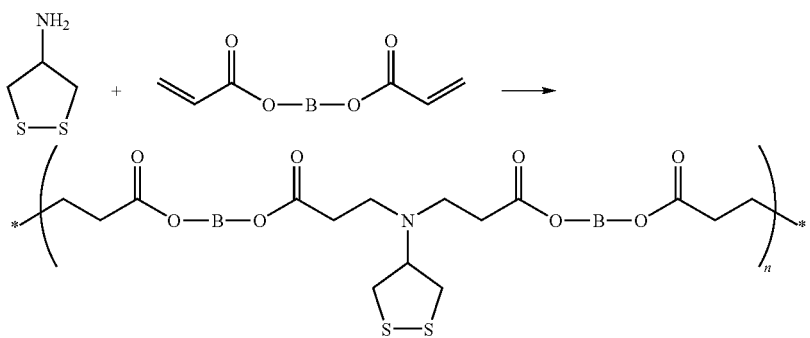

-continued

Formula 30

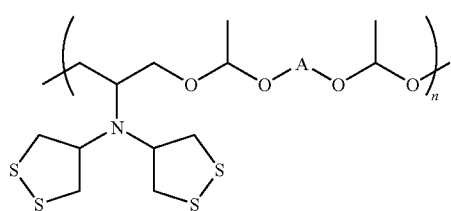

Synthesis of Polymer—Representative Polymerization in Methanol

The polymer is synthesized by Michael addition of the amines to diacryl esters. In an exemplary experiment, diacrylate (40 mmol, 1 equiv) and [1,2]-dithiolane amine (40 mmol, 1 equiv) are dissolved in anhydrous methanol (100 ml). The reaction mixture is stirred for two days at room temperature. The reaction mixture is added dropwise into stirred hexane or diethyl ether. The polyacetal is collected and dried in a vacuum at room temperature for 4 hours to give the polymer.

Examples of the polymers in these embodiments include but are not limited to the following:

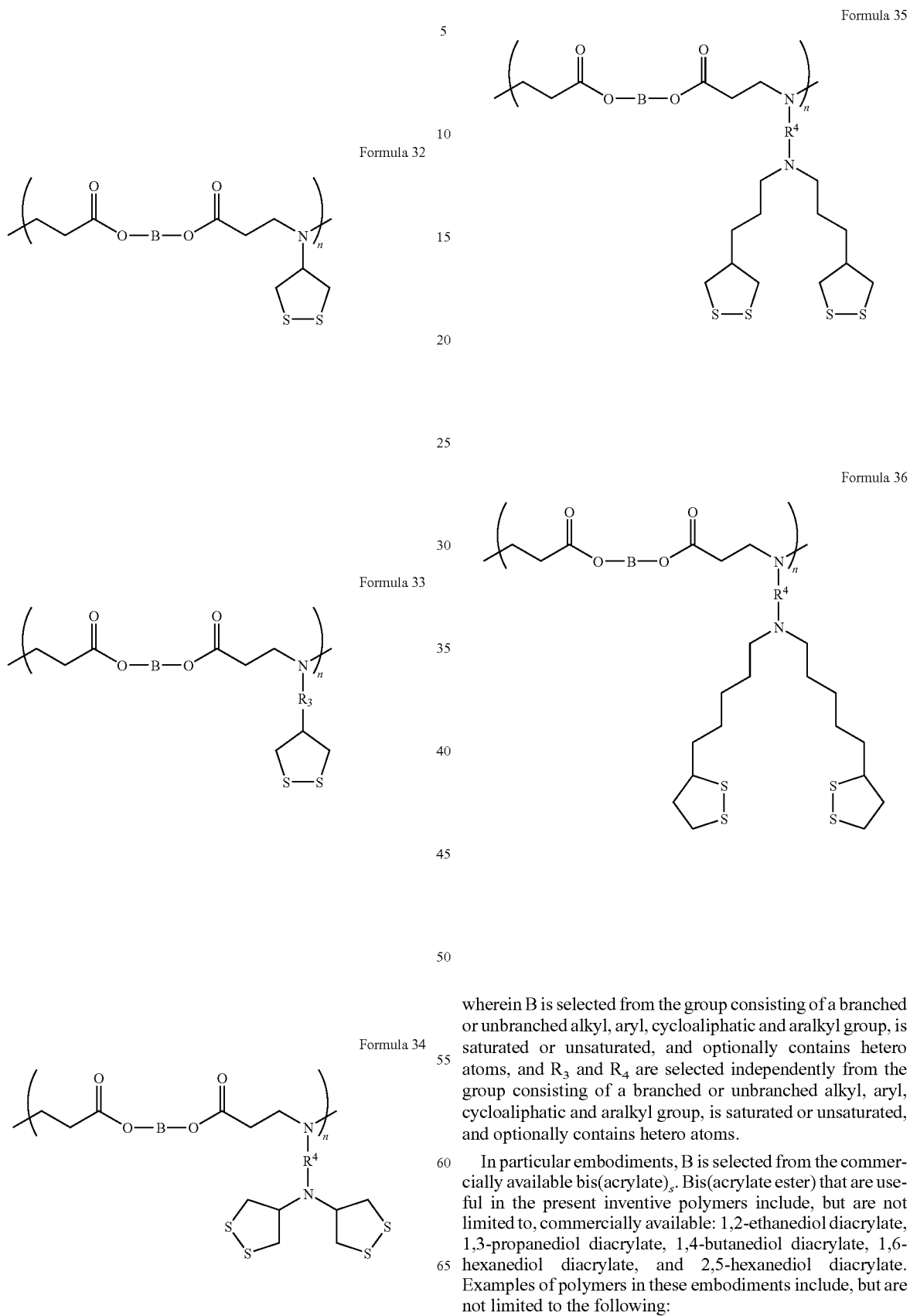

wherein B is selected from the group consisting of a branched or unbranched alkyl, aryl, cycloaliphatic and aralkyl group, is saturated or unsaturated, and optionally contains hetero atoms, and $R_3$ and $R_4$ are selected independently from the group consisting of a branched or unbranched alkyl, aryl, cycloaliphatic and aralkyl group, is saturated or unsaturated, and optionally contains hetero atoms.

In particular embodiments, B is selected from the commercially available bis(acrylate)$_s$. Bis(acrylate ester) that are useful in the present inventive polymers include, but are not limited to, commercially available: 1,2-ethanediol diacrylate, 1,3-propanediol diacrylate, 1,4-butanediol diacrylate, 1,6-hexanediol diacrylate, and 2,5-hexanediol diacrylate. Examples of polymers in these embodiments include, but are not limited to the following:

Formula 37

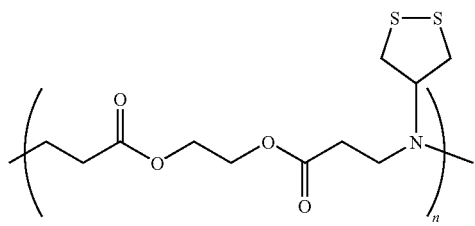

Formula 38

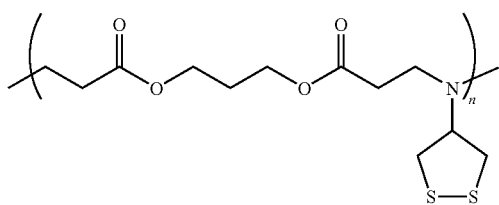

Formula 39

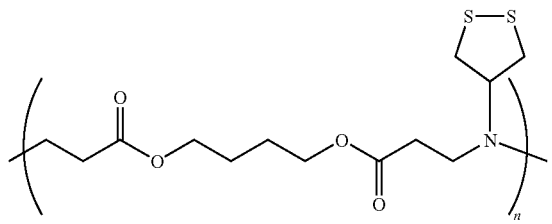

Formula 40

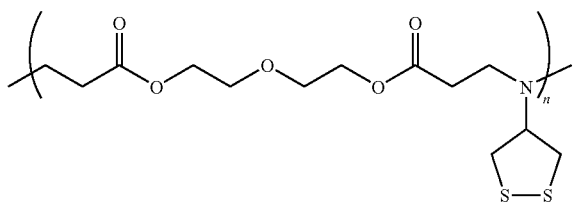

Formula 41

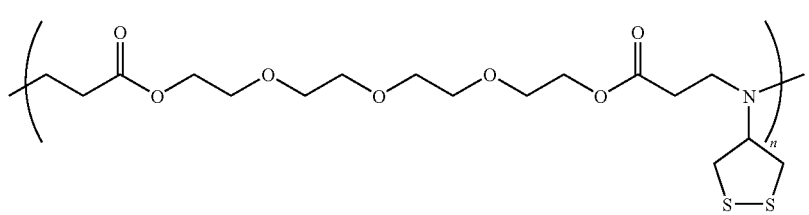

Example 3

Polymer Type III

In one embodiment, the inventive polymers are prepared by conjugation of two monomers, both of which contain dithiolane. The Type 2 dithiolane monomer contains a primary amine and the dithiolane monomer contains a bis(acrylate ester). The polymers are prepared by the conjugate addition of a primary amine to a bis(acrylate ester). The reaction scheme is shown below.

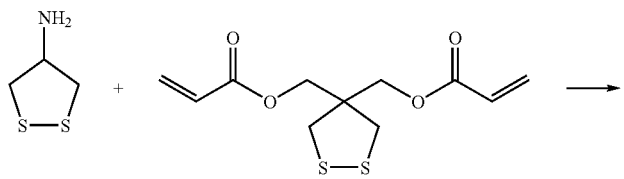

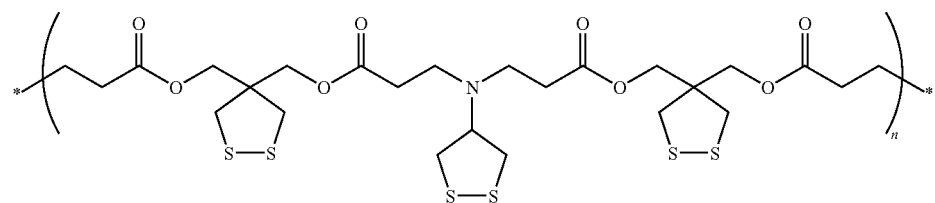

Synthesis of Polymer—Representative Polymerization in Methanol

In an exemplary experiment, [1,2]-dithiolane diacrylate (40 mmol, 1 equiv) and [1,2]-dithiolane amine (40 mmol, 1 equiv) are dissolved in anhydrous methanol (100 ml). The reaction mixture is stirred for two days at room temperature. The reaction mixture is added dropwise into stirred hexane or diethyl ether. The polyacetal is collected and dried in a vacuum at room temperature for 4 hours to give the polymer.

Examples of polymers in these embodiments include, but are not limited to the following:

Formula 42

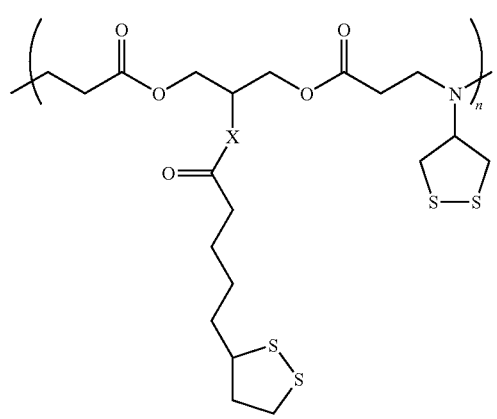

Formula 43

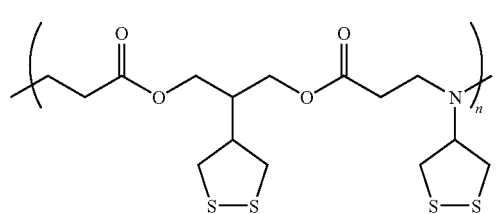

Formula 44

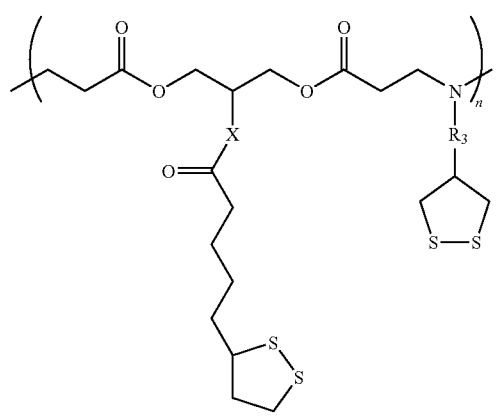

Formula 45

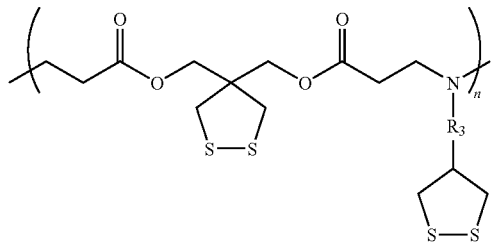

Formula 46

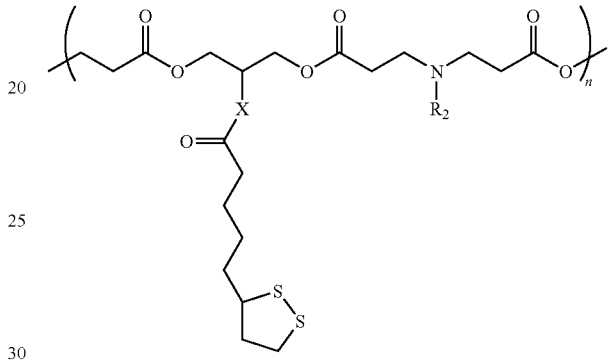

Formula 47

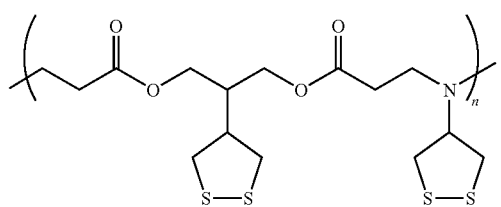

Formula 48

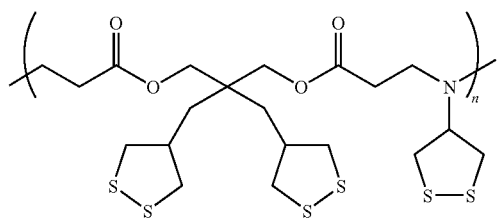

Formula 49

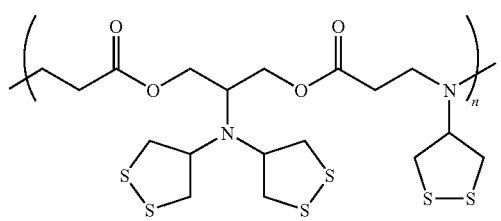

Formula 50
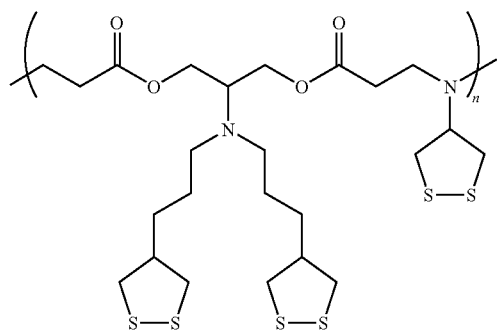
Formula 51
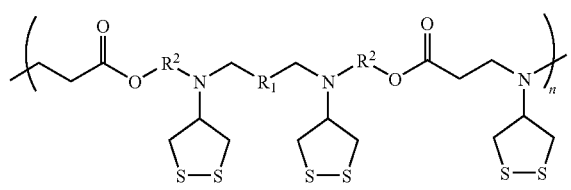
Formula 52
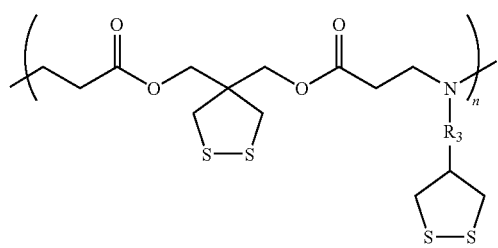
Formula 53
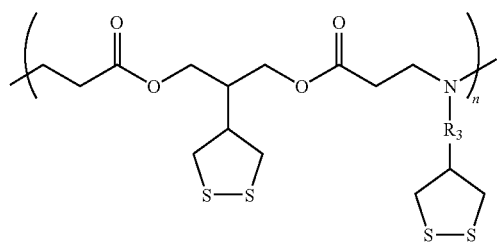
Formula 54
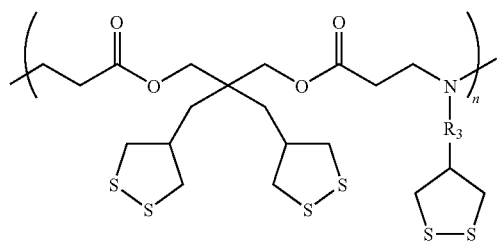
Formula 55
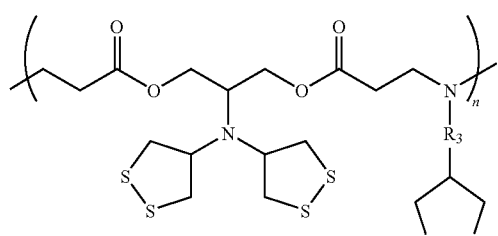
Formula 56
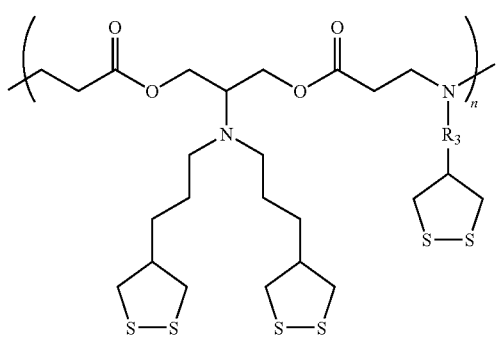
Formula 57
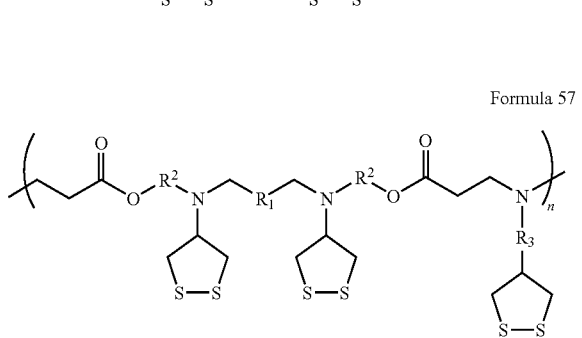
Formula 58
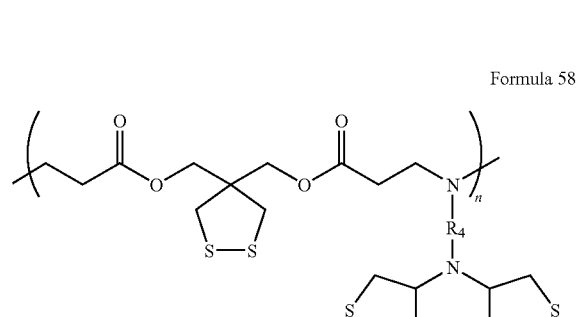
Formula 59
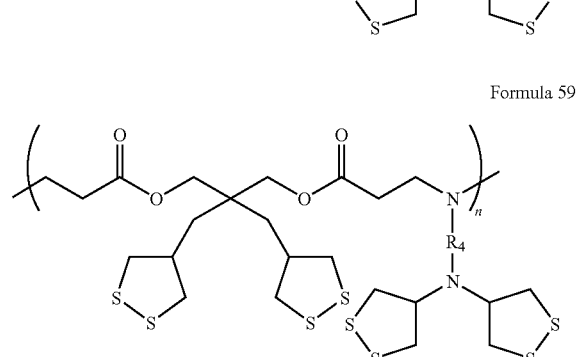
Formula 60
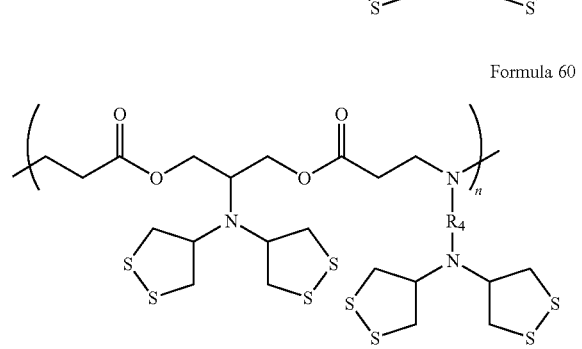

Formula 61
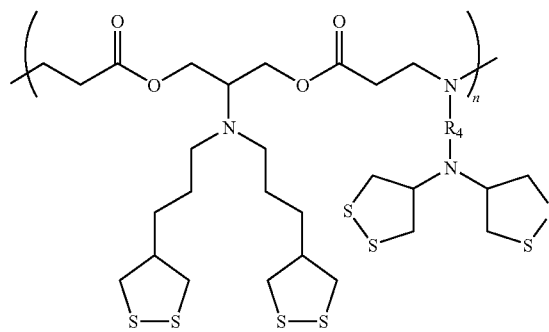
Formula 62
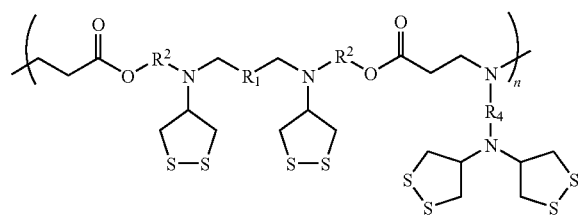
Formula 63
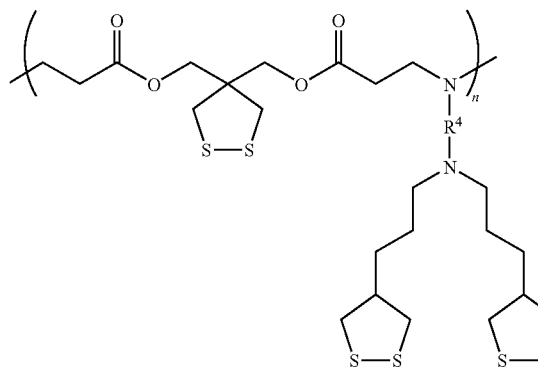
Formula 64
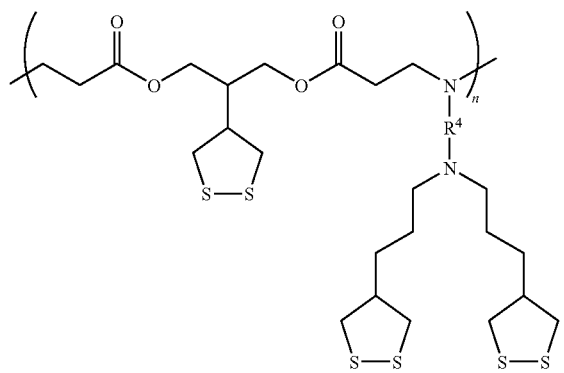
Formula 65
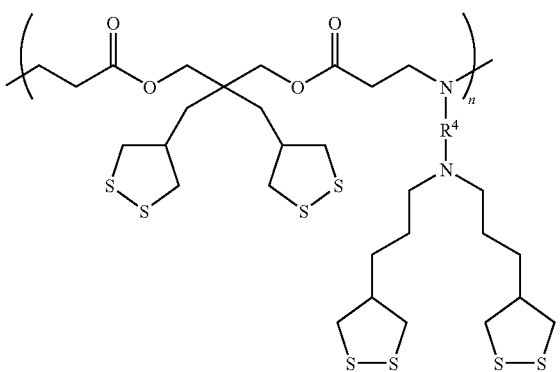
Formula 66
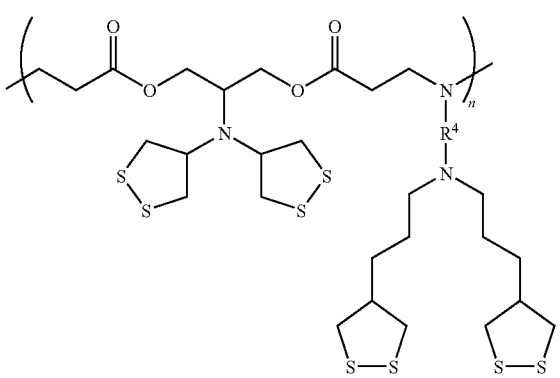
Formula 67
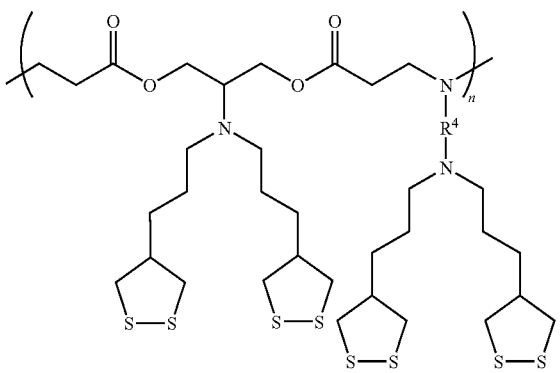
Formula 68
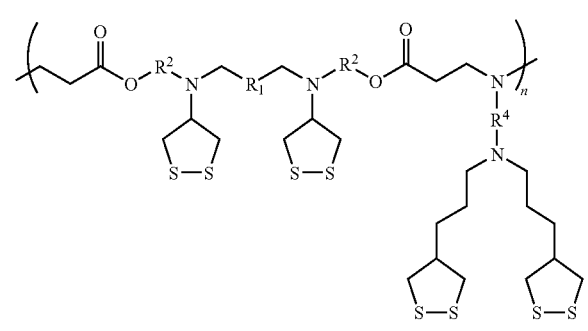

wherein X is selected from the group consisting of a branched or unbranched alkyl, aryl, cycloaliphatic and aralkyl group, is saturated or unsaturated, and optionally contains hetero atoms, and $R_1$, $R_2$, $R_3$ and $R_4$ and $R_5$ are each independently selected from the group consisting of a branched or unbranched alkyl, aryl, cycloaliphatic and aralkyl group, is saturated or unsaturated, and optionally contains hetero atoms.

Example 4

Polymer Type-IV

In another embodiment, the inventive polymers are prepared by the addition of primary amines to a dithiolane monomer. The reaction scheme is shown below.

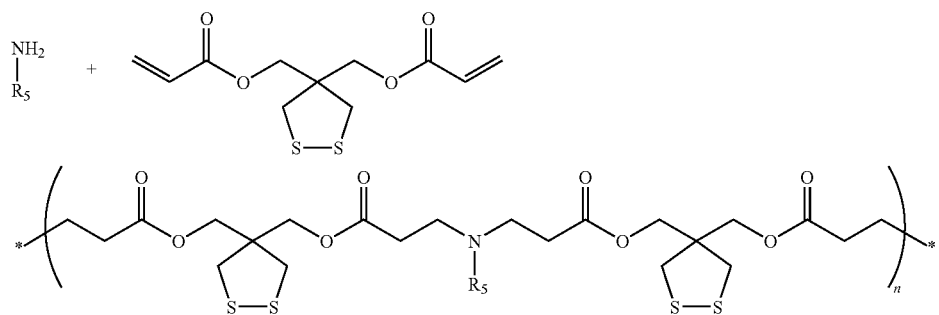

Synthesis of Polymer—Representative Polymerization in Methanol

In a manner similar to that described above, [1,2]-dithiolane diacrylate (40 mmol, 1 equiv) and primary amine (40 mmol, 1 equiv) are dissolved in anhydrous methanol (100 ml). The reaction mixture is stirred for two days at room temperature. The reaction mixture is added dropwise into stirred hexane or diethyl ether. The polyacetal is collected and dried in a vacuum at room temperature for 4 hours to give the polymer.

Examples of polymers in these embodiments include, but are not limited to the following:

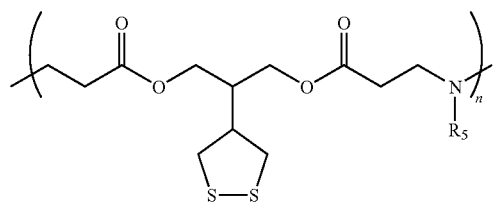

Formula 69

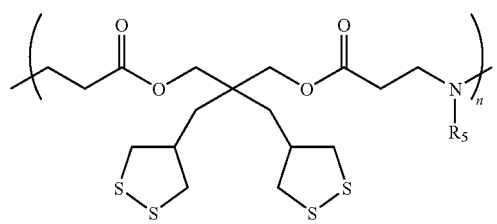

Formula 70

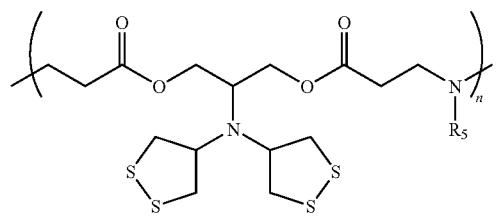

Formula 71

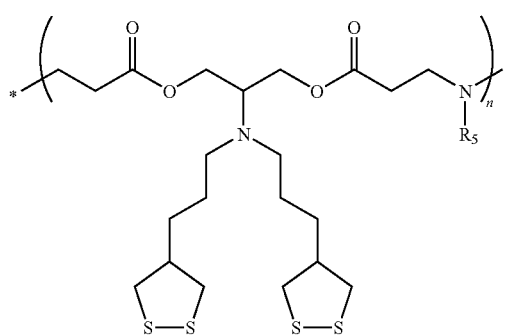

Formula 72

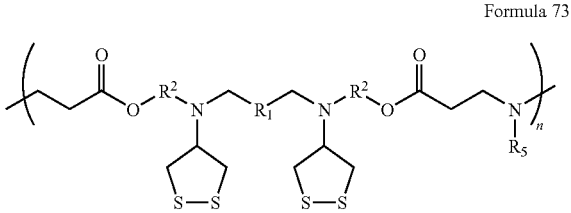

Formula 73 wherein $R_1$, $R_2$, $R_4$ and $R_5$ are each independently selected from the group consisting of a branched or unbranched alkyl, aryl, cycloaliphatic and aralkyl group, is saturated or unsaturated, and optionally contains hetero atoms.

In alternative embodiments, $R_5$ is selected from the commercially available primary amines. Examples of polymers in these embodiments include, but are not limited to the following:

Formula 74

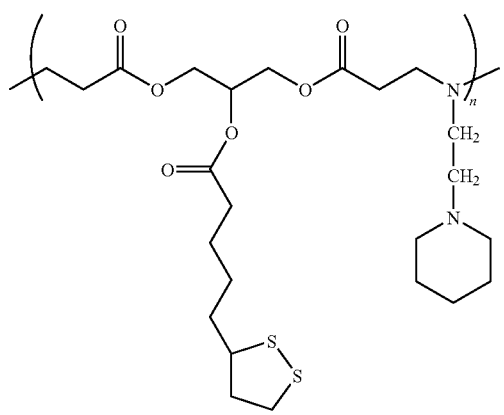

Formula 75

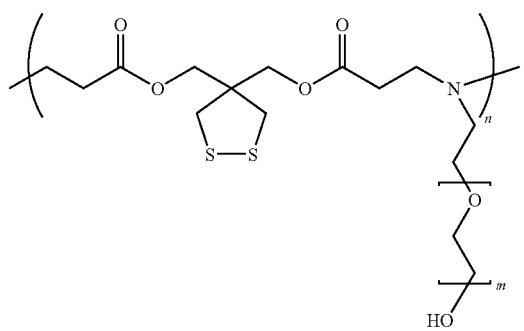

Formula 76 wherein m is an integer of at least 2.

Example 5

Polymer-Type V

In another embodiment, the inventive polymers are prepared by the addition of a diamine to a dithiolane monomer. The reaction scheme is shown below.

$H_2N-X-NH_2$ +

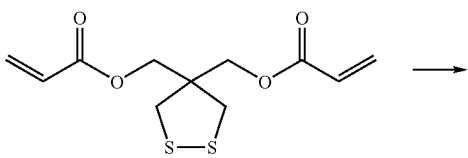

Synthesis of Polymer—Representative Polymerization in Methanol

In a manner similar to that described above, [1,2]-dithiolane diacrylate (40 mmol, 1 equiv) and diamine (40 mmol, 1 equiv) are dissolved in anhydrous methanol (100 ml). The reaction mixture is stirred for two days at room temperature. The reaction mixture is added dropwise into stirred hexane or diethyl ether. The polyacetal is collected and dried in a vacuum at room temperature for 4 hours to give the polymer.

Examples of polymers in these embodiments include, but are not limited to the following:

Formula 77

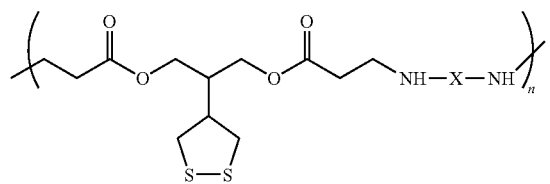

Formula 78

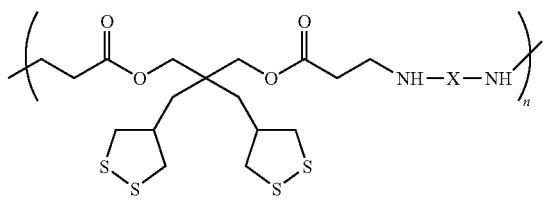

Formula 79
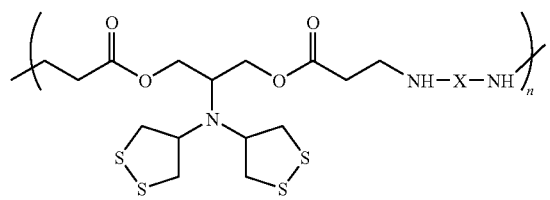
Formula 80
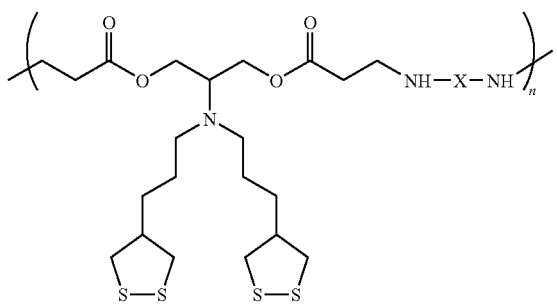
Formula 81
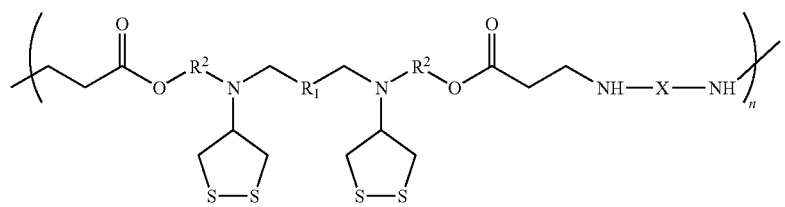
In particular embodiments, the diamine is selected from commercially available primary amines. Examples of polymers in these embodiments include but are not limited to the following:
Formula 82
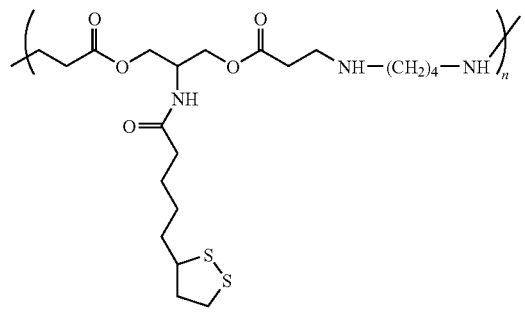
Formula 83
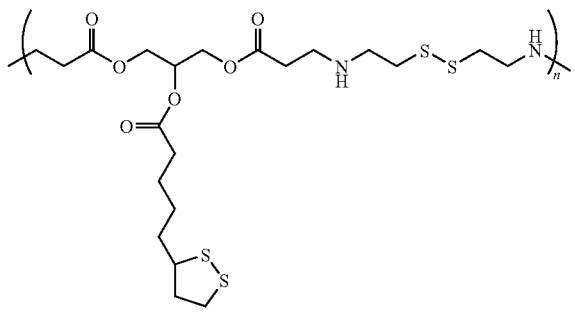
Formula 84
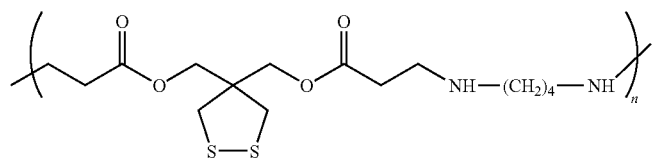

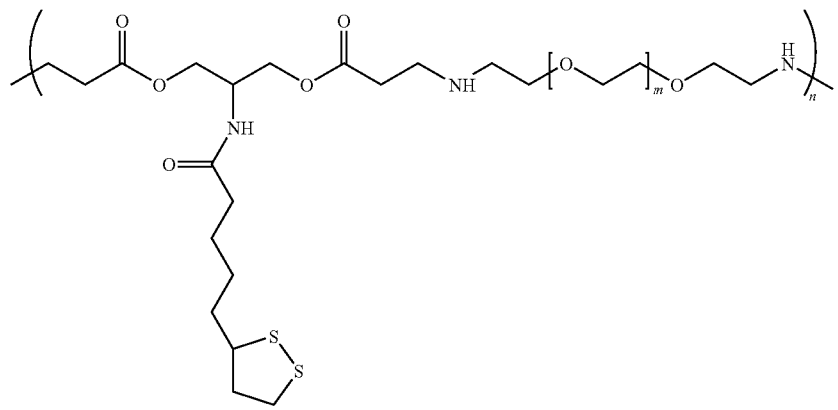

Formula 85

Example 6

Polymer-Type VI

In another embodiment, the inventive polymers are prepared by the addition of a bis(secondary amine) to a dithiolane monomer. The reaction scheme is shown below.

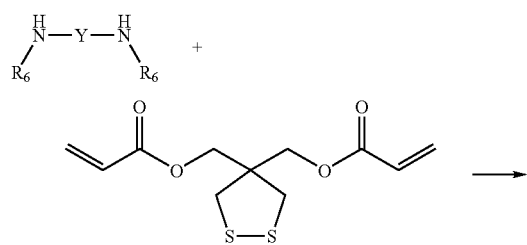

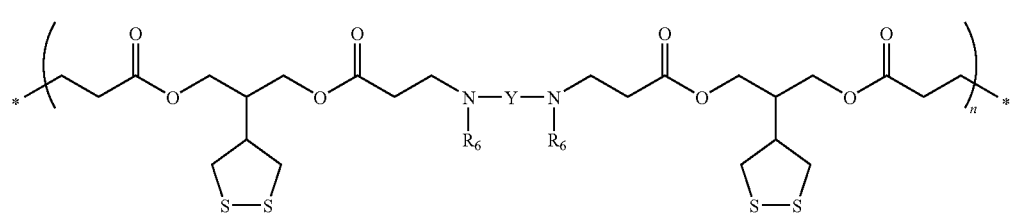

Synthesis of Polymer—Representative Polymerization in Methanol

In a manner similar to that described in above, [1,2]-dithiolane diacrylate (40 mmol, 1 equiv) and N,N'-dimethylethylenediamine (40 mmol, 1 equiv) are dissolved in anhydrous methanol (100 ml). The reaction mixture is stirred for two days at room temperature. The reaction mixture is added dropwise into stirred hexane or diethyl ether. The polyacetal is collected and dried in a vacuum at room temperature for 4 hours to give the polymer.

Examples of polymers in these embodiments include but are not limited to the following:

Formula 86

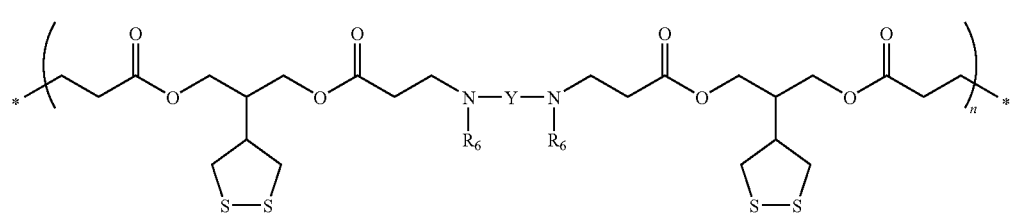

Formula 87

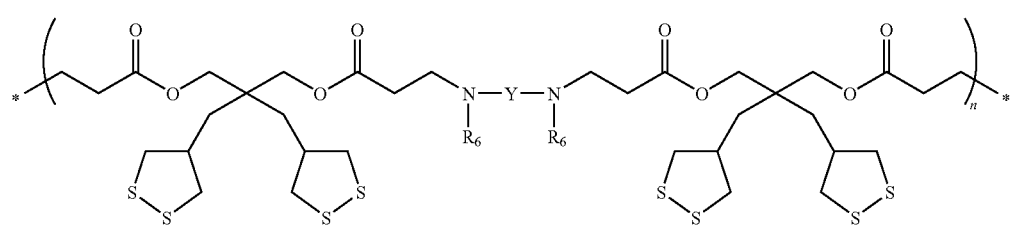

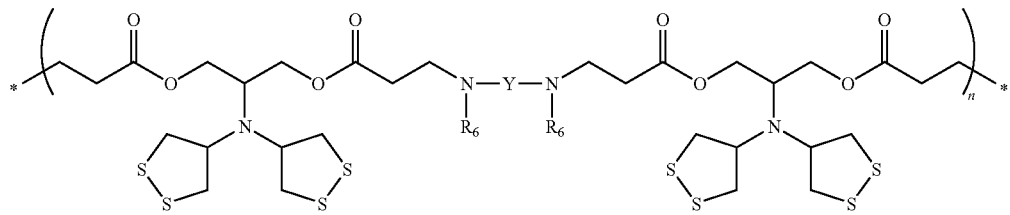
Formula 88
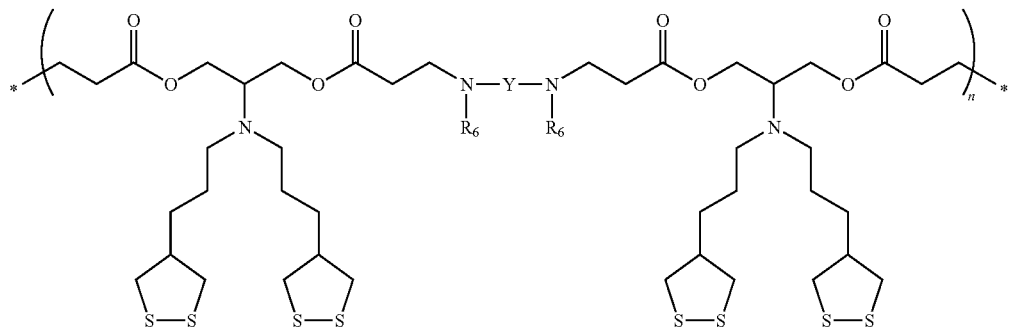
Formula 89
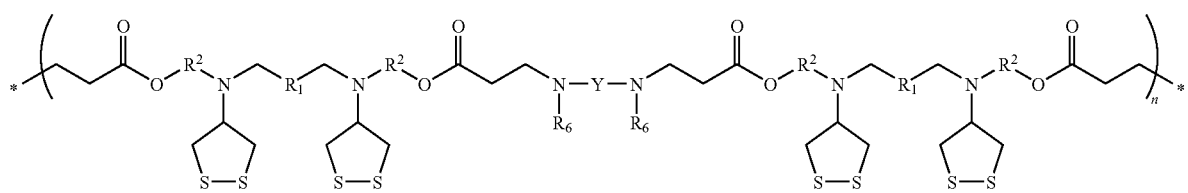
Formula 90
Formula 91
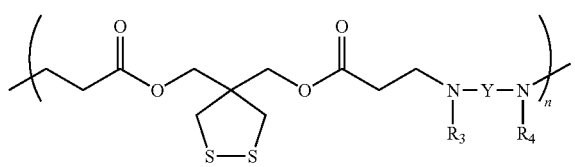
Formula 92
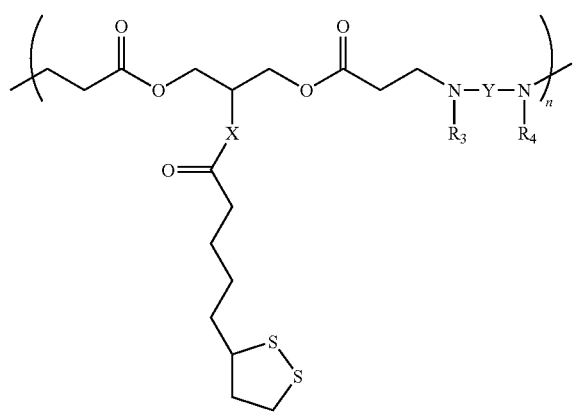

In particular embodiments, the bis(secondary amine) is selected from commercially available primary amines. Examples of polymers in these embodiments include but are not limited to the following:

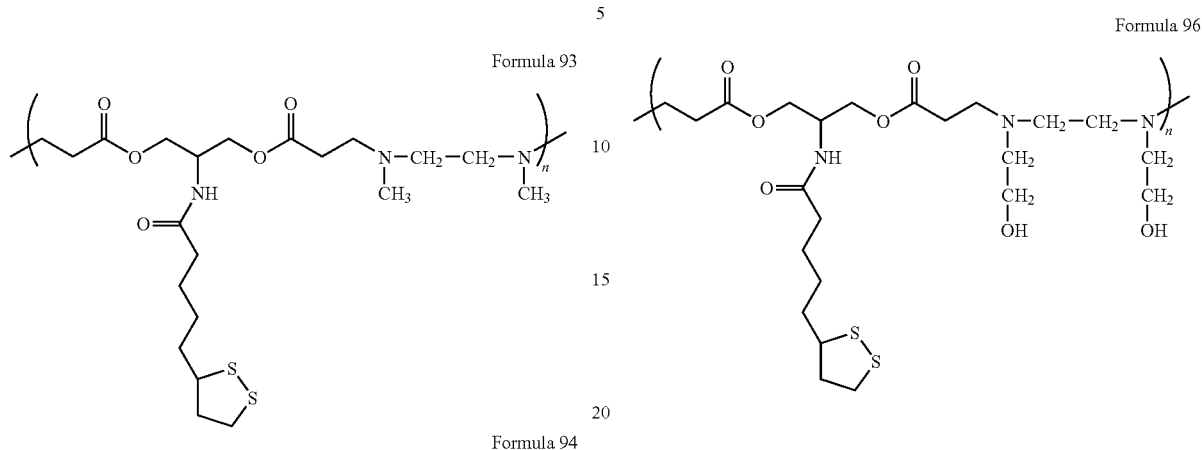

Formula 93

Formula 94

Formula 95

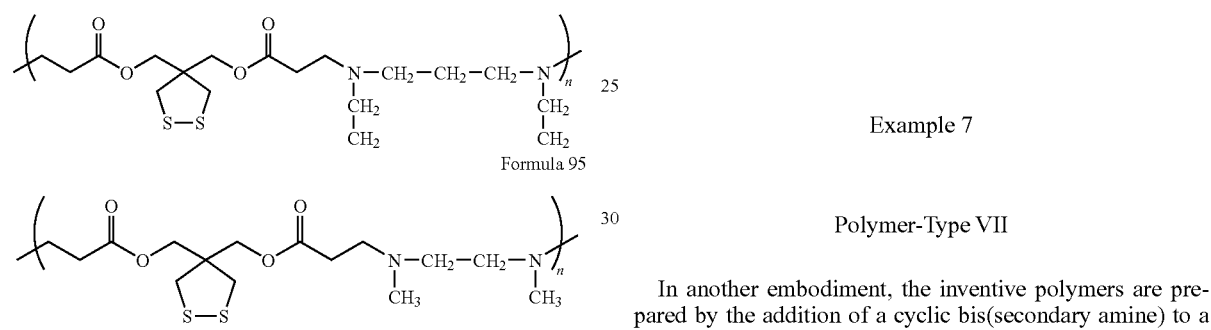

Formula 96

Example 7

Polymer-Type VII

In another embodiment, the inventive polymers are prepared by the addition of a cyclic bis(secondary amine) to a dithiolane monomer. The reaction scheme is shown below.

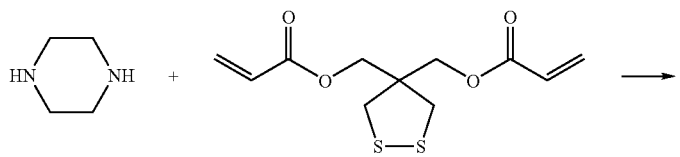

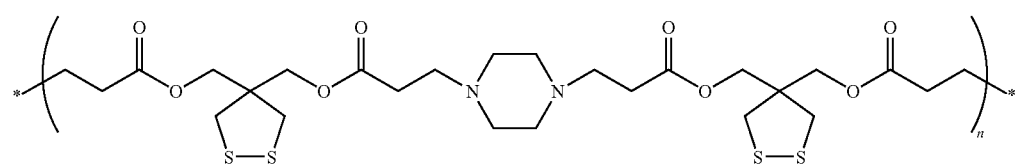

Synthesis of Polymer—Representative Polymerization in Methanol

In a manner similar to that described above, [1,2]-dithiolane diacrylate (40 mmol, 1 equiv) and piperazine (40 mmol, 1 equiv) are dissolved in anhydrous methanol (100 ml). The reaction mixture is stirred for two days at room temperature. The reaction mixture is added dropwise into stirred hexane or diethyl ether. The polyacetal is collected and dried in a vacuum at room temperature for 4 hours to give the polymer. Examples of polymers in these embodiments include but are not limited to:

Formula 97

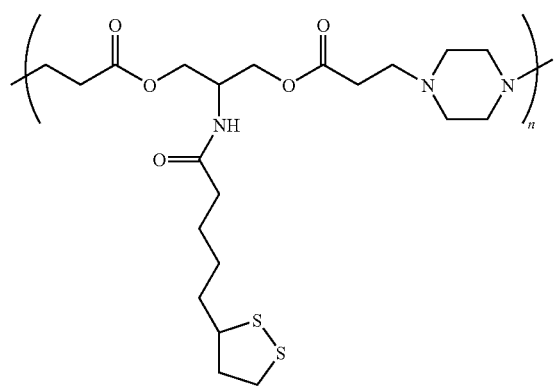

Formula 99

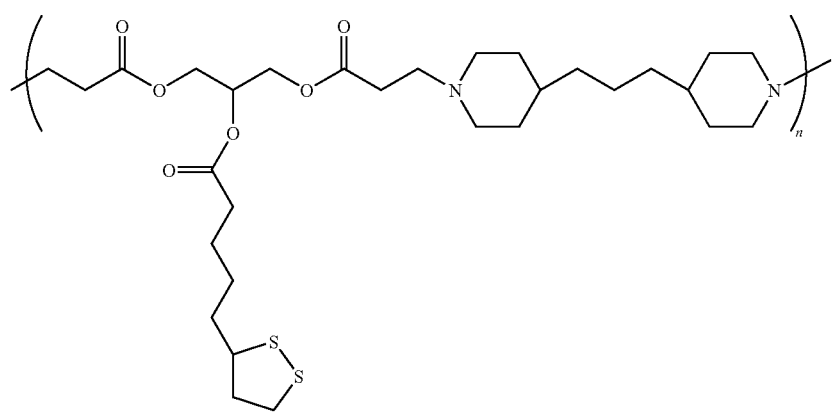

Formula 100

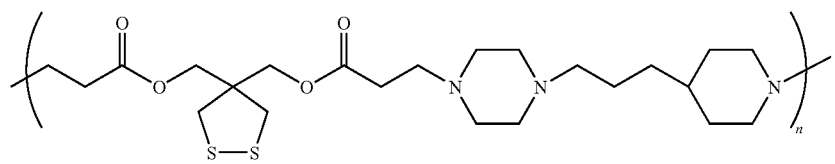

Preparation of the Antioxidant Polymers by Covalent Attachment of the Antioxidant [1,2]-dithiolane Derivatives to Diverse Polymers In another aspect, the antioxidant polymers are prepared by covalent attachment of the antioxidant [1,2]-dithiolane derivatives to functional polymers.

The attachment of the antioxidant [1,2]-dithiolane derivatives to the polymers via an amide or ester bond may be performed by any appropriate method known in the art. In one embodiment, the starting polymer contains pending carboxylic acid side groups and the [1,2]-dithiolane derivatives are covalently bonded to the polymer via biodegradable ester or amide bond. The [1,2]-dithiolane derivatives include but are not limited to the following:

Formula 11

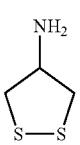

Formula 98

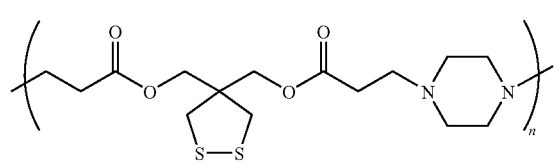

-continued

Formula 12

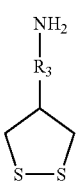

-continued

Formula 13
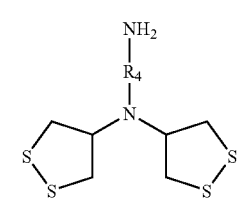

Formula 14
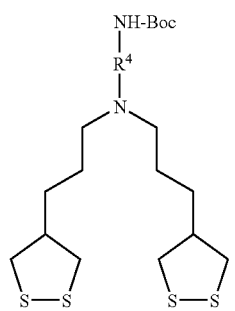

Formula 15
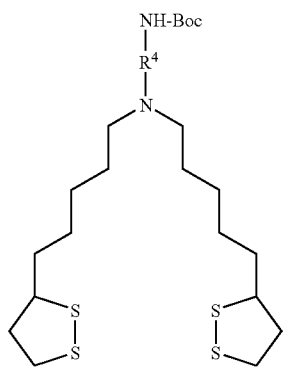

Formula 16
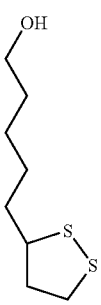

Formula 17
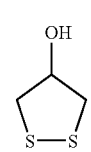

Formula 18
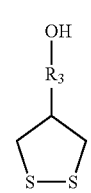

wherein the $R_3$ and $R_4$ groups may be hydrocarbon groups; for example, an alkyl, aryl, cycloaliphatic or aralkyl group; and may be saturated or unsaturated. The $R_3$ and $R_4$ groups may contain hetero atoms (e.g., nitrogen, oxygen, sulfur, etc.).

The starting polymers may be of natural or synthesitc origin, and homopolymers or block copolymers or dendrimers with carboxylic acid terminated dendrimers. For lipolol synthesis, Journal of Pharmaceutical Sciences, 85, 1996, 496-504 may provide guidance to one of skill in the art. For the synthesis of monohydroxy dithiolane derivatives, European Journal of Medicine Chemistry 38, 2003, 1-11 may provide guidance to one of skill in the art.

The polycarboxylic acids include, but are not limited to:

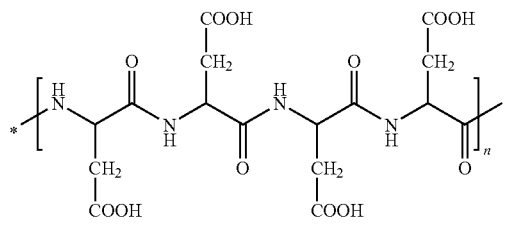
Poly(α-aspartic acid)

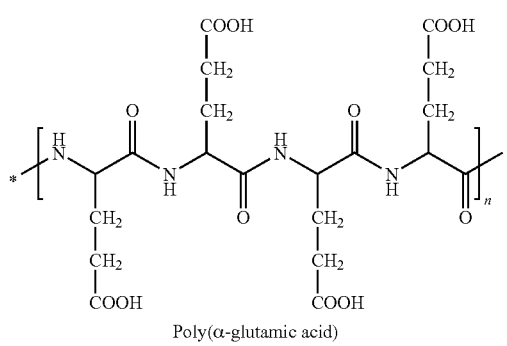
Poly(α-glutamic acid)

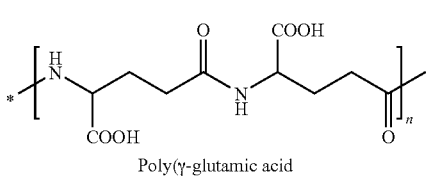
Poly(γ-glutamic acid)

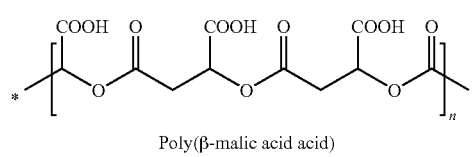
Poly(β-malic acid acid)

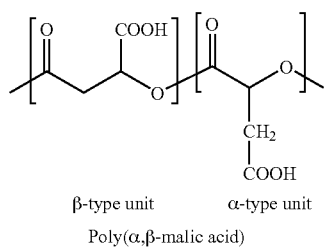
β-type unit   α-type unit
Poly(α,β-malic acid)

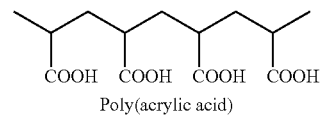
Poly(acrylic acid)

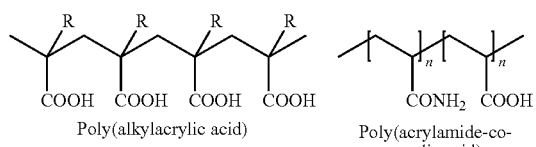
Poly(alkylacrylic acid)     Poly(acrylamide-co-acrylic acid)
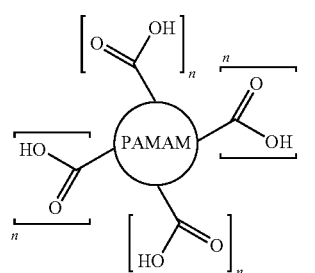
Poly(amido amine) (PAMAM)dendrimer, carboxylic acid terminated
Examples of the inventive antioxidant polymers include but are not limited to the following:
Formula 101
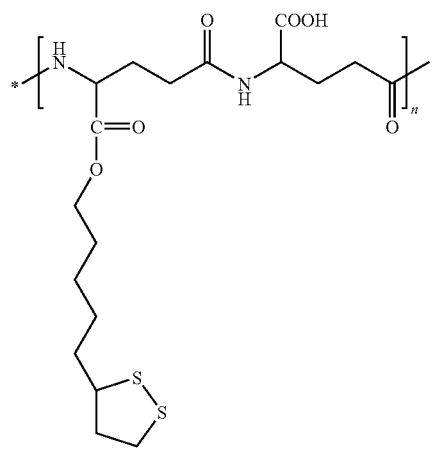
Formula 102
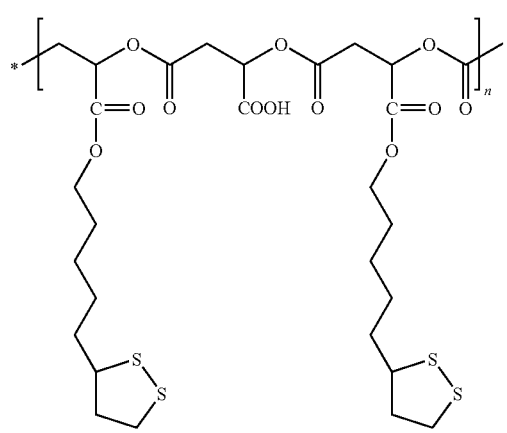
Formula 103
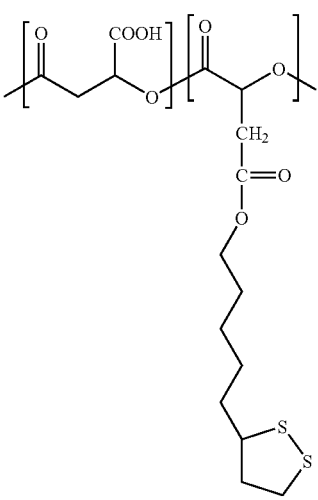
Formula 104
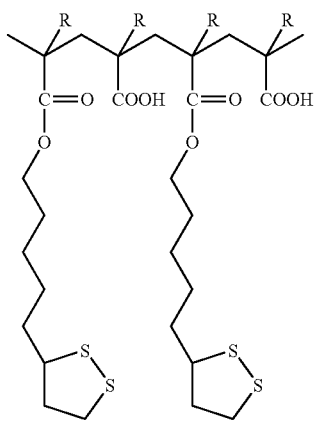
Formula 105
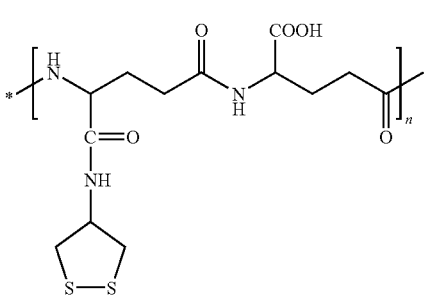
Formula 106
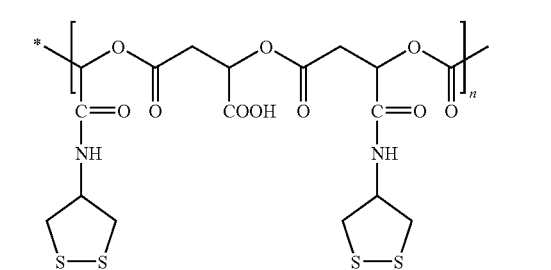

Formula 107
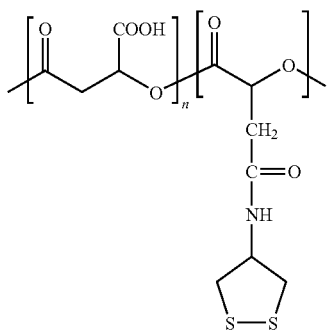

Formula 108
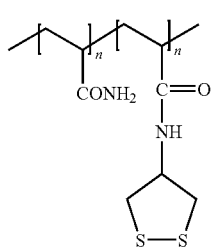

Formula 109
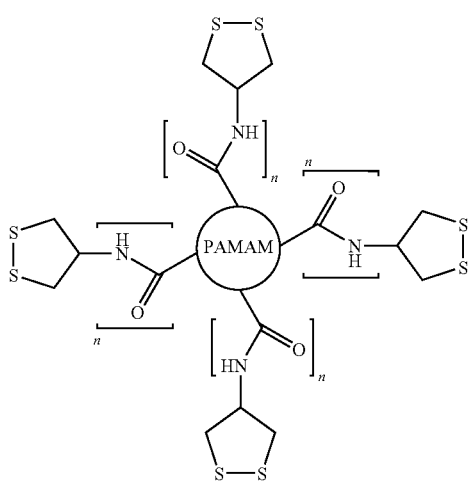

Formula 110
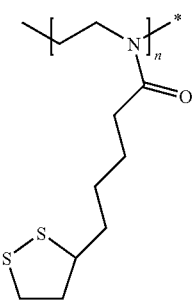

Formula 111
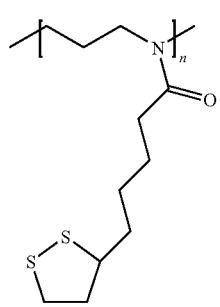

Formula 112
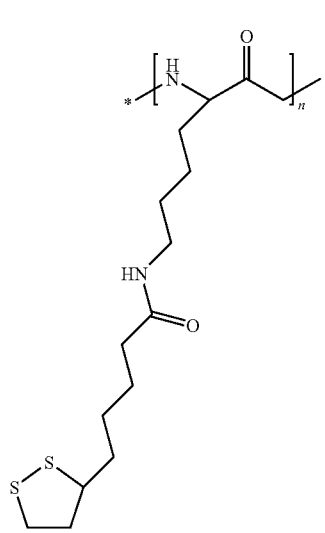

Formula 113
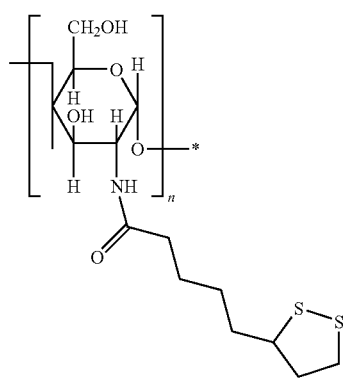

In another embodiment, the starting polymer contains pending primary amine or secondary amine groups and the 1,2-dithiolane-3-pentanoic acid (thioctic acid, α-lipoic acid) is covalently bonded to the polymer via, amide bond. The starting polymers may be of natural or synthesitc origin, and homopolymers or block copolymers or dendrimers. The starting polyamines include, but not limited to: poly(ethyleneimine), poly(propylenimine), polylysine, chitosan, primary amine terminated dendrimers including, but not limited to, poly(amido amide)(PAMAM) dendrimers, poly(propylenimine) dendrimer, octaamine dendrimers, and hexadecaamine dendrimer.

Examples of the inventive antioxidant polymers include but are not limited to the following formulas:

-continued

Formula 114

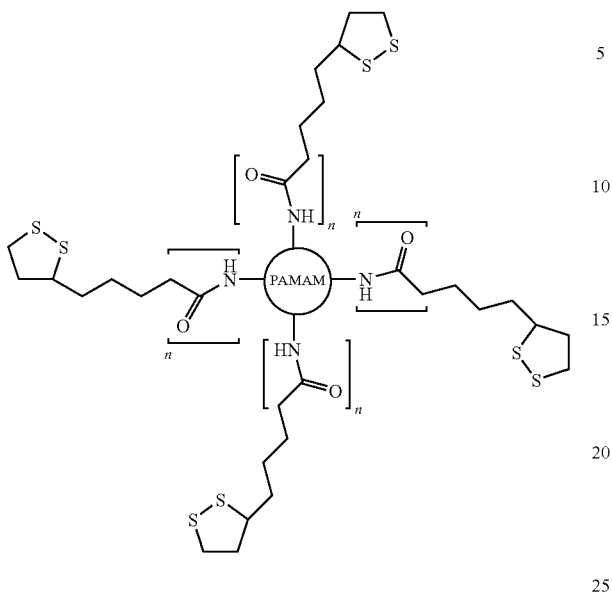

Dendrimers are hyperbranched polymers in which the atoms are arranged in many branches and subbranches along a central backbone of carbon atoms. (See e.g., Zeng, F and Zimmerman, S. C, Chem. Rev. 1997, 97, 1681-1712 Matthews et al., Prog. Polym. Sci., 23, 1-56, 1998)

In another embodiment, the starting polymer contains pending hydroxyl groups and the 1,2-dithiolane-3-pentanoic acid (thioctic acid, α-lipoic acid) is covalently bonded to the polymer via, ester bond. The starting polymers may be of natural or synthesitc origin, and homopolymers or block copolymers, polysaccharides including, but not limited to, pullulan, amylose, mannan, amylopectin, dextran and cyclodextrin, and hydroxyl terminated dendrimers. The polyols include, but not limited to:

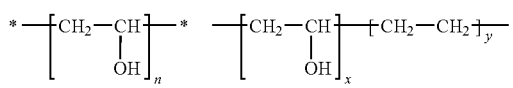

Poly(vinyl alcohol)    Poly(vinyl alcohol-co-ethylene) ethylene

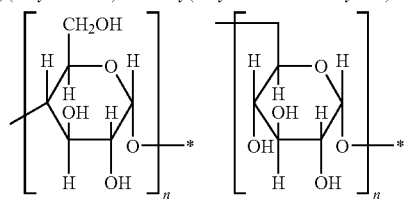

Pullulan    Dextran

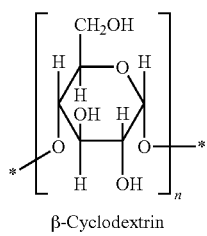

β-Cyclodextrin n = 7

Examples of the inventive antioxidant polymers include but are not limited to the following formulas:

Formula 115

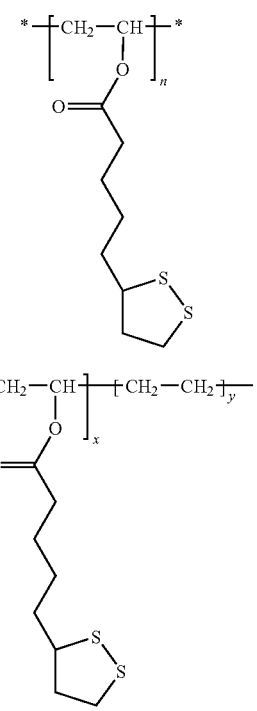

Formula 116

Formula 117

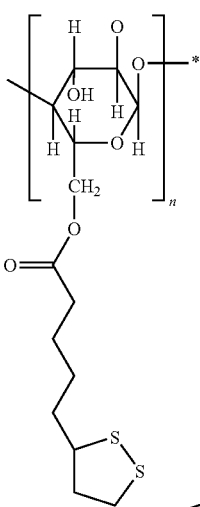

Formula 118

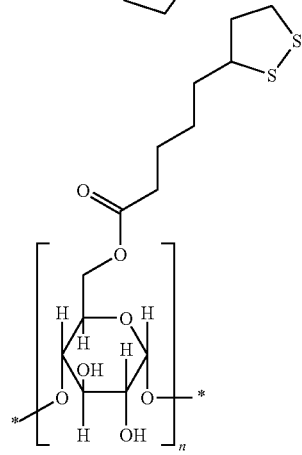

Preparation of Various Compounds

All reactions for the synthesis of 1,2-dithiolane derivatives are monitored by thin layer chromatography (TLC): silicagel plates from Merck 60 F254; compounds are visualized by irritation with UV light and/or by treatment with a solution of 1.5 g of KMnO$_4$, 10 g K$_2$CO$_3$, and 1.25 mL 10% NaOH in 200 mL of H$_2$O, followed by gentle heating. Compounds with amine functional group are visualized by ninhydrin test.

Example 8

Preparation of 1,2-Dithiolane(diol)

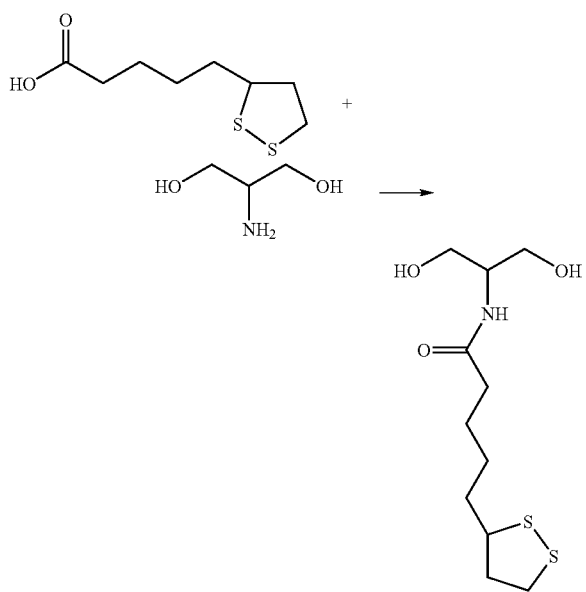

α-Lipoic acid (15 mmol) and serinol (15 mmol) are dissolved in 100 mL dichloromethane, followed by the addition of 1-hydroxybenzotriazole (HOBt, 20 mmol) and TEA (30 mmol). The reaction mixture is cooled to 0° C. and 1-ethyl-3-(3-dimethylaminopropyl) carbodiimide hydrochloride (EDC.HCl, 20 mmol) is added portionwise. The mixture is stirred for 5 h at room temperature. The reaction mixture is washed with deionized water (3×200 mL), dried with MgSO$_4$ and the solvent is evaporated under vacuum. The crude product was purified by silicagel column chromatography (250 mL) eluting with CHCl$_3$:MeOH (45:5).

Example 9

Preparation of 1,2-Dithiolane(diol)

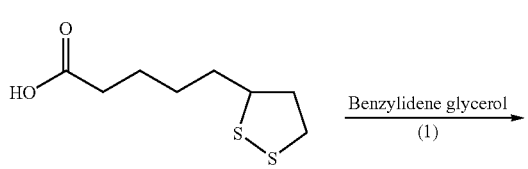

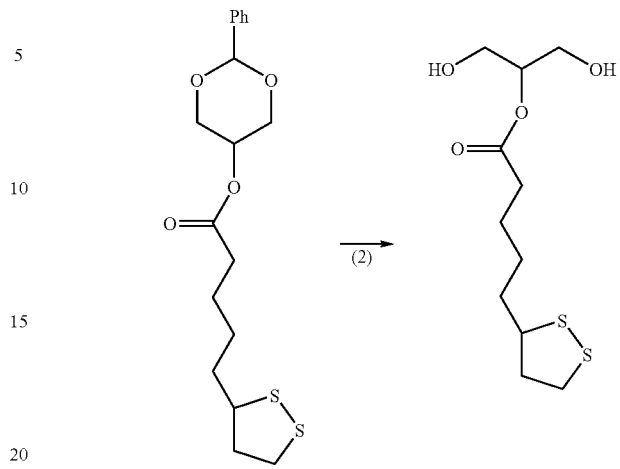

Step 1: Synthesis of Lipoic Acid Benzylidene Glycerol Ester

α-Lipoic acid (15 mmol) and 1,3-O-benzylideneglycerol (15 mmol) are dissolved in 100 mL dichloromethane, followed by the addition of 4-(dimethylamino) pyridine (DMAP, 20 mmol). The reaction mixture is stirred for 10 min at room temperature and EDC. HCl (20 mmol) was added portionwise. The mixture is stirred for 5 h at room temperature. The reaction mixture is washed with deionized water (3×200 mL), dried with MgSO$_4$ and the solvent was evaporated under vacuum. The crude product is purified by silicagel column chromatography (250 mL) eluting with CHCl$_3$: MeOH (95:1).

Step 2: Synthesis of Lipoic Acid Glycerol Ester

α-Lipoic acid benzylidene glycerol ester (10 mmol) is dissolved in 20 ml of methanol containing 0.6 ml of conc. HCl and refluxed for 4 hours. 250 ml of water is added, the pH is adjusted to 6 with solid NaOH, and methanol is evaporated under vacuum. NaCl was added to ~10% and the product is extracted with dichloromethane (3×100 mL). The combined dichloromethane extracts are dried over Na$_2$SO$_4$, filtered and evaporated. The residue is dried under vacuum and the product is purified by chromatography on a silica gel column eluted with ethyl acetate.

Example 10

Preparation of 1,2-Dithiolane(diol)

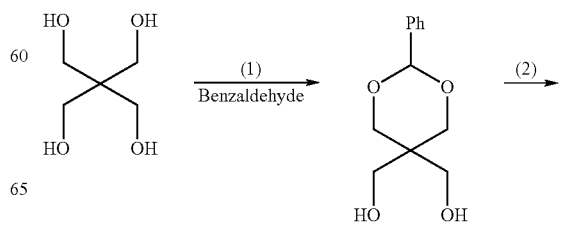

-continued

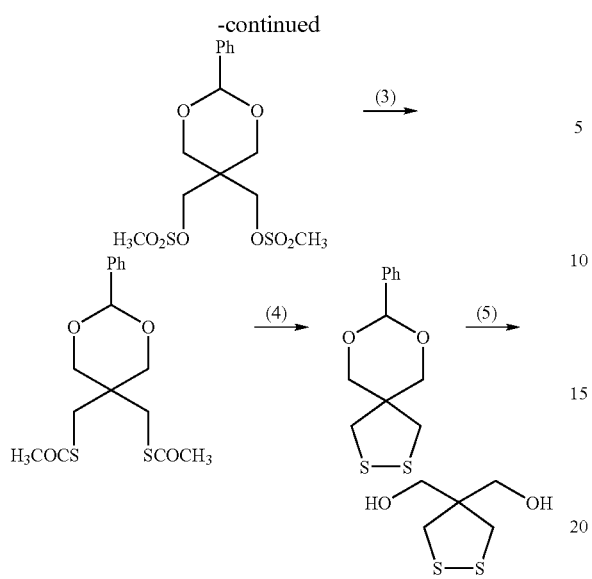

Step 1: Pentaerythritol monobenzaldehyde was synthesized according the procedure as described in the literature (See e.g., *Organic Syntheses, Coll. Vol.* 4, p. 679; Vol. 38, p. 65)

Step 2: Synthesis of bis-(methanesulfonic acid ester) of monobenzalpentaerythritol Methanesulfonyl chloride (20.7 g, 0.18 mol) was added at 5° C. to a stirred solution of monobenzalpentaerythritol (0.028 mol) and triethylamine (56 ml) in dichloromethane (115 ml). The mixture was stirred at 5° C. for 5 h and at 20° C. for 20 h. Dichloromethane (200 ml) was added and the mixture was washed with an aqueous solution of sodium hydrogen carbonate, dried with $Na_2SO_4$ and concentrated to dryness under vacuum. Chromatography of the residue on silicagel (1.2 L) eluting with hexane/ethyl acetate (50:50) gives bis-(methanesulfonic acid ester) of monobenzalpentaerythritol.

Step 3: Synthesis of Dimercaptoacetyl of Monobenzalpentaerythritol (Under Argon Atmosphere)

Bis-(methanesulfonic acid ester) of monobenzalpentaerythritol (0.015 mol) was dissolved in dimethylformamide (50 ml). Potassium thioacetate (0.06 mol) in 50 mL of DMF was added dropwise. The reaction mixture was stirred overnight at room temperature and then concentrated under vacuum, poured into brine (300 mL) and extracted with ethyl acetate (3×200 mL). The organic layer was washed with water (3×300 mL), dried over sodium sulfate and evaporated under vacuum. Chromatography of the residue on silicagel eluting with a mixture of hexane and ethyl acetate (50:50) gives 1,2-dithiolane of monobenzalpentaerythritol.

Step 4: Synthesis of 1,2-dithiolane of Monobenzalpentaerythritol

A solution of dimercaptoacetyl monobenzalpentaerythritol (4.1 mmol) in EtOH (20 ml) is treated with 10 ml of aqueous 1 N NaOH at room temperature for 1 h. The mixture is diluted with $CH_2Cl_2$ (100 ml) and then an aqueous solution of 0.1 M iodine (4.5 mmol) is added dropwise. The reaction mixture was stirred for 2 hours at room temperature and 1 mmol of $Na_2S_2O_3$ (1 M aqueous solution) was added to the reaction mixture. The organic phase was separated, washed with water (3(200 mL), dried with magnesium sulfate, and evaporated at room temperature. The crude product is chromatographed on silica gel (200 mL) using a solvent mixture of hexane and ethyl acetate (40:20) as eluent to give 1,2-dithiolane of monobenzalpentaerythritol.

Step 5: Synthesis of 1,2-dithiolane pentaerythritol 1,2-Dithiolane of monobenzalpentaerythritol (10 mmol) was dissolved in 20 ml of methanol containing 0.6 ml of conc. HCl and refluxed for 4 hours. 250 ml of water was added, the pH was adjusted to 6 with solid NaOH, and methanol was evaporated under vacuum. NaCl was added to ~10% and the product was extracted with dichloromethane (3×100 mL). The combined dichloromethane extracts were dried over $Na_2SO_4$, filtered and evaporated. The residue was dried under vacuum and the product is purified by chromatography on a silica gel column eluted with ethyl acetate.

Example 11

Preparation of 1,2-Dithiolane(diol) of Type III

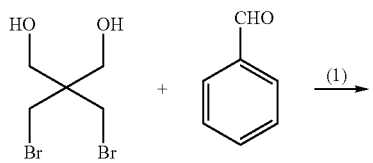

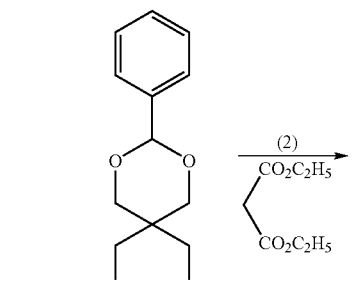

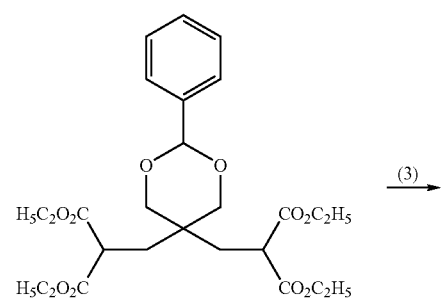

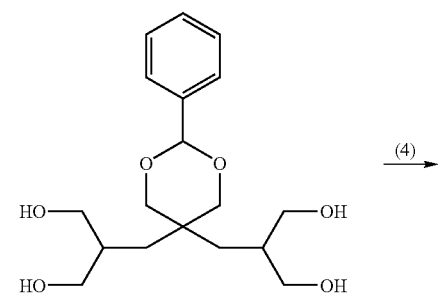

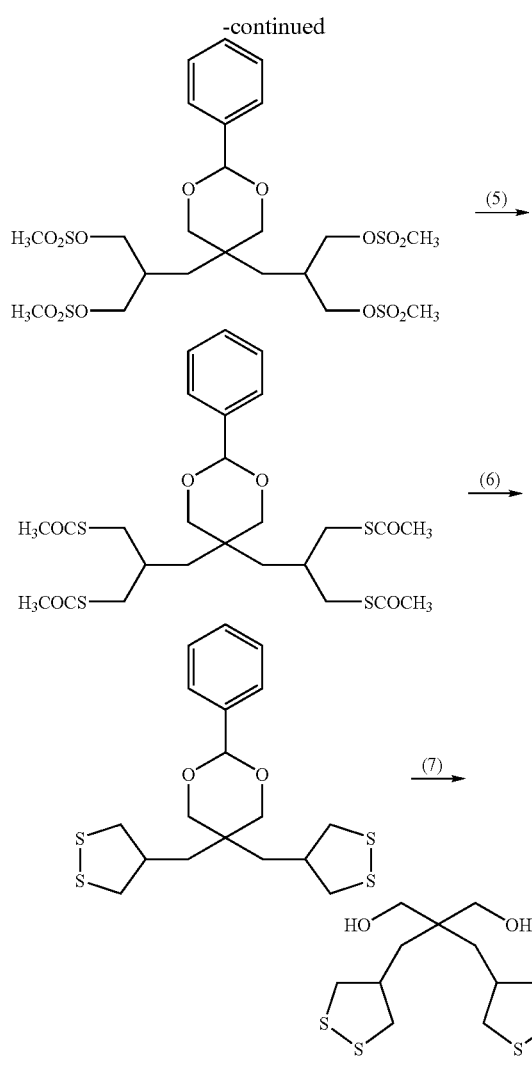

Step 1: Synthesis of Dibromomonobenzalpentaerythritol 2,2-Bis(bromomethyl)-1,3-propanediol (100 mmol), benzaldehyde (100 mmol), and p-toluenesulfonic acid monohydrate (3 mmol) are dissolved in 150 mL of cyclohexane. The stirred mixture is heated with azeotropic removal of water. The solution is allowed to cool to room temperature and then evaporated under vacuum at room temperature. The residue is dissolved in 100 mL of diethyl ether, and washed with saturated aqueous potassium bicarbonate (50 mL), and with water (2×50 mL). The ether layer is dried over magnesium sulfate and filtered. The solvent is evaporated under vacuum at room temperature. The solid crude product is collected by filtration. The crude solid product is triturated with 50 mL of hexanes and the purified product is collected by filtration.

Step 2: Synthesis of Bis-(diethyl malonate) Monobenzalpentaerythritol

Sodium (100 mmol) is added over 20 min to ethanol (100 mL) to give sodium ethoxide. Malonic acid diethyl ester (100 mmol) is added and the mixture is stirred for 10 min and concentrated under vacuum to dryness. The residue is taken up with toluene and the suspension concentrated under vacuum to dryness. The residue is dissolved in dimethylformamide (200 mL), dibromomonobenzalpentaerythritol (0.50 mmol) is added, the mixture stirred for 4 days at 20° C. and concentrated to dryness under vacuum. The residue is dissolved in ether, washed successively with aqueous solutions of sodium hydrogencarbonate and lithium chloride, dried ($Na_2SO_4$) and the solvent is evaporated to dryness. The excess of diethyl malonate is distilled from the residue under reduced pressure to give bis-(diethyl malonate) monobenzalpentaerythritol.

Step 3: Synthesis of bis-(propane-1,3-diol) Monobenzalpentaerythritol

Bis-(diethyl malonate) monobenzalpentaerythritol (100 mmol) dissolved in diethyl ether (100 mL) is added dropwise to a lithium aluminium hydride in diethyl ether (100 mL) suspension. The mixture is stirred for 2 h at reflux temperature and 20 h at 20° C. After cooling at 5° C., water (5 mL), 2 N aqueous solution of sodium hydroxide (10 mL) and water (5 mL) is successively added. The suspension is filtered, the solid is washed with diethylether and the combined filtrates are dried ($Na_2SO_4$) and concentrated under vacuum. The crude product is chromatographed on silica gel using a solvent ethyl acetate as eluent to give the product.

Step 4-Step 7 were performed in a manner similar to that described in the Example for preparation of 1,2-dithiolane pentaerythritol.

Example 12

Preparation of 1,2-Dithiolane(diol) of Type II

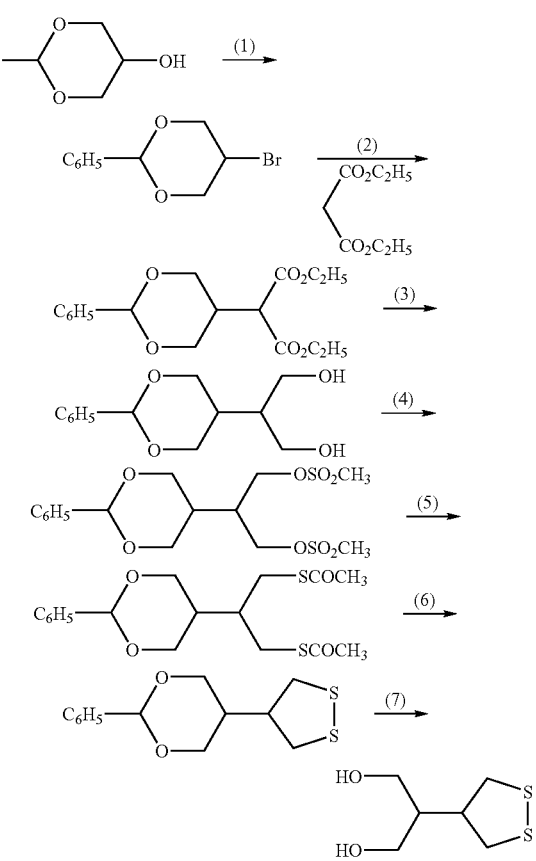

The compounds are prepared in a manner similar to that described above.

Example 13

Preparation of 4-Bromo-[1,2]-Dithiolane (Type I)

(See e.g. Morera et. al. Org. Lett. 4, 1139-1142, 2002)

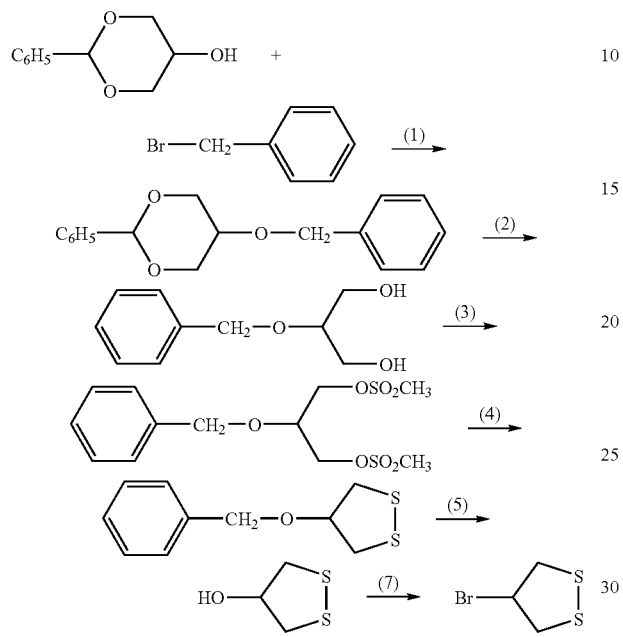

Steps 1 and 2: Synthesis of 2-Benzyloxy-1,3-propanediol

Sodium hydride (1 g, 60% in mineral oil, 42 mmol, 1.67 g) is suspended in freshly distilled THF (100 mL), and the mixture is cooled in an ice/$H_2O$ bath. 1,3-O-Benzylidene glycerol (28 mmol) is added in portions, and the mixture is stirred for 15 min. Benzyl bromide (40 mmol) is added via a syringe, and the reaction is stirred at 0° C. to room temperature overnight. Approximately half of the THF is evaporated under reduced pressure, and 20 mL of $H_2O$ and 60 mL of 10% aqueous HCl are added. The mixture is refluxed for 2 h, cooled to room temperature, and is poured into 10 mL of saturated aqueous $Na_2CO_3$. The solution is extracted with ethyl acetate (3 times with 20 mL). The extracts are dried over $Na_2SO_4$ and evaporated and purified by column chromatography (eluant:from hexane/ethyl acetate (50/50) ethyl acetate 100%).

Step 3: A solution of 2-Benzyloxy-1,3-propanediol (20 mmol) in dry $CH_2Cl_2$ (50 mL) is additioned with dry TEA (90 mmol) and then treated with methanesulfonyl chloride (65 mmol) at 0° C. for 30 min (dropwise added at 0° C.). The reaction mixture is stirred for 2 h at room temperature. The mixture is washed with 50 mM sodium bicarbonate (6-7 times with 300 mL), dried over magnesium sulfate and the solvent is evaporated under reduced pressure. The product is precipitated by adding of hexane and slowly evaporating $CH_2Cl_2$ and the yellowish product is washed with hexane and dried.

Step 4: 2-Benzyloxy-1,3-dimethanesulfonyl propanediol (45 mmol) is dissolved in DMF (180 mL) and sulfur (1.5 g) and sodium sulfide monohydrate (11 g) is added. The reaction mixture is stirred at 85° C. for 4 h and diethylether is added (500 mL). The reaction mixture is washed with brine, dried with sodium sulfate and evaporated under vacuum. The crude product is purified by column chromatography (eluant:hexane/ethyl acetate, 95/5).

Step 5: 4-(Benzyloxy)-[1,2]dithiolane (7.06 mmol) is dissolved in 1,2-dichloroethane (20 mL). A 1 M solution of boron tribromide-methylsulphide complex in dichloromethane (20 mL) is added and the mixture stirred at 20° C. for 2 h, poured in an aqueous solution of sodium hydrogencarbonate and extracted with diethyl ether. The combined organic layers are dried ($Na_2SO_4$) and evaporated at room temperature. The crude product is purified by column chromatography (eluant: 100% $CHCl_3$).

Step 6: Synthesis of 4-Bromo-[1,2]-Dithiolane (See e.g., Saah et al. Journal of Pharmaceutical Sciences 85,496-504, 1996) 4-Hydroxy-[1,2]-Dithiolane (3 mmol) and triphenylphosphine (9 mmol) are dissolved in 15 mL of anhydrous tetrahydrofuran, THF. Zinc bromide (3 mmol) in 10 mL of THF is added followed by diethyl azidodicarboxylate, DEADC (9 mmol) in 5 mL of THF. The mixture is stirred at room temperature under nitrogen atmosphere until 4-Hydroxy-[1,2]-Dithiolane disappears. Methanol (2.0 mL) is then added to the reaction mixture and after 5 min, the mixture is extracted with ether (20 mL), the organic layer is washed with 12 mL of water, saturated $Na_2CO_3$, and brine successively, and the organic solvent is evaporated under vacuum at room temperature. The crude product is purified by silicagel column chromatography (eluant:hexane/ethyl acetate, 95/5).

Example 14

Preparation of α-Bromo-ω-[1,2]-Dithiolane from diols (Type I)

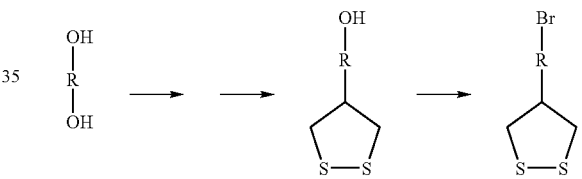

Guillonneau et al. European Journal of Medicinal Chemistry 38, 1-11, 2003 and Morera et. al. Org. Lett. 4, 1139-1142, 2002 provides one skilled in the art guidance to prepare this particular compound.

Example 15

Preparation of [1,2]-dithiolane-3-pentanol(Lipolol)

[1,2]-dithiolane-3-pentanol(lipolol) is prepared in a manner similar to that described in the Example for preparation of 4-bromo-[1,2]-dithiolane.

Example 16

Preparation of 1,2-Dithiolane(diol)

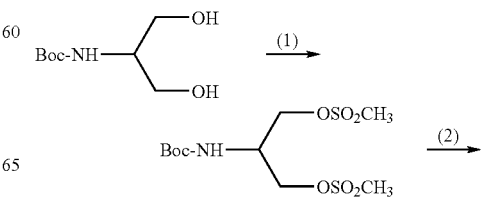

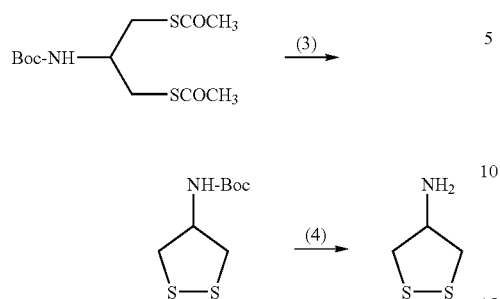

Step 1: Synthesis of bis-(methanesulfonic acid ester) of boc-serinol

Methanesulfonyl chloride (130 mmol) was added at 5° C. to a stirred solution of boc-serinol (40 mol) and triethylamine (25 ml) in dichloromethane (100 ml). The mixture was stirred at 5° C. for 5 h and at 20° C. for 20 h. Dichloromethane (200 ml) was added and the mixture was washed with an aqueous solution of sodium hydrogen carbonate (50 mM), dried ($Na_2SO_4$) and concentrated to dryness under vacuum. Chromatography of the residue on silicagel (1.2 L) eluting with hexane/ethyl:acetate (50:50) gave bis-(methanesulfonic acid ester) of boc-serinol.

Step 3: Synthesis of dimercaptoacetyl of boc-serinol

Bis-(methanesulfonic acid ester) of boc-serinol (0.015 mol) was dissolved in dimethylformamide (50 ml). Potassium thioacetate (0.06 mol) in 50 mL of DMF was added dropwise. The reaction mixture was stirred overnight at room temperature and then concentrated under vacuum, poured into brine (300 mL) and extracted with ethyl acetate (3×200 mL). The organic layer was washed with water (3×300 mL), dried over sodium sulfate and evaporated under vacuum. Chromatography of the residue on silicagel eluting with a mixture of hexane and ethyl acetate (50:50) gave 1,2-dithiolane of boc-serinol.

Step 4: Synthesis of 1,2-dithiolane of boc-serinol

A solution of dimercaptoacetyl boc-serinol (4.1 mmol) in EtOH (20 ml) was treated with 10 ml of aqueous 1 N NaOH at room temperature for 1 h. The mixture was diluted with $CH_2Cl_2$ (100 ml) and then an aqueous solution of 0.1 M iodine (4.5 mmol) is added dropwise. The reaction mixture was stirred for 2 hours at room temperature and 1 mmol of $Na_2S_2O_3$ (1 M aqueous solution) was added to the reaction mixture. The organic phase was separated, washed with water (3×200 mL), dried with magnesium sulfate, and evaporated at room temperature. The crude product was chromatographed on silica gel (200 mL) using a solvent mixture of hexane and ethyl acetate (40:20) as eluent to give 1,2-dithiolane of boc-serinol.

Step 5: Synthesis of 1,2-dithiolane serionol 1,2-Dithiolane of boc-serinol (1 mmol) was dissolved in 2.5 ml of dichloromethane and 2.5 mL of TFA was added at 0° C. The reaction mixture was stirred for 30 min at 0° C. and evaporated under vacuum. The remaining TFA was removed azotropically with ether and toluene and dried under high vacuum at room temperature. The crude product was purified by chromatography on a silica gel column eluted with $CHCl_3$: MeOH (45:5).

Example 17

Preparation of α-Amino-col-ω-[1,2]-dithiolan-4-yl-alkane

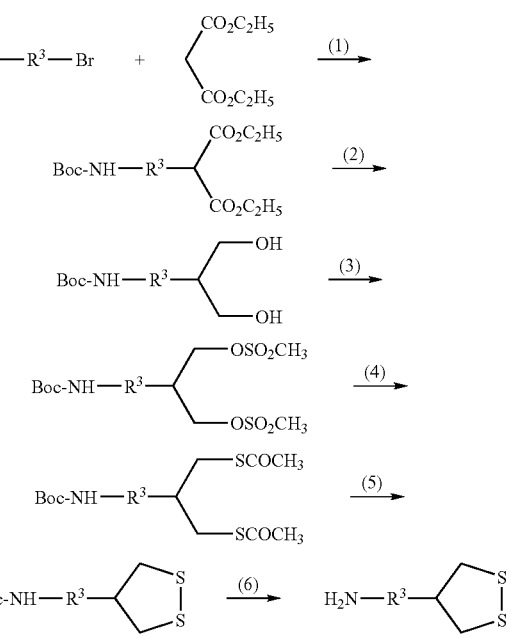

Step 1: Sodium (11 g, 0.48 mol) is added over 20 min to ethanol (400 mL) to give sodium ethoxide. Malonic acid diethyl ester (80 g, 0.5 mol) is added and the mixture is stirred for 10 min and concentrated under vacuum to dryness. The residue is taken up with toluene and the suspension concentrated under vacuum to dryness. The residue is dissolved in dimethylformamide (1 L), (boc-amino)alkyl bromide (0.48 mol) is added, the mixture is stirred for 4 days at 20° C. and concentrated to dryness under vacuum. The residue is dissolved in ether, washed successively with aqueous solutions of sodium hydrogencarbonate and lithium chloride, dried ($Na_2SO_4$), concentrated and distilled under reduced pressure. The crude product is then purified by silicagel column chromatography.

Step 3: Synthesis of bis-(propane-1,3-diol) monobenzalpentaerythritol

Bis-(diethyl malonate) (100 mmol) dissolved in diethyl ether (100 mL) is added dropwise to a lithium aluminium hydride in diethyl ether (100 mL) suspension. The mixture is stirred for 2 h at reflux temperature and 20 h at 20° C. After cooling at 5° C., water (5 mL), 2 N aqueous solution of sodium hydroxide (10 mL) and water (5 mL) is successively added. The suspension is filtered, the solid is washed with diethylether and the combined filtrates are dried ($Na_2SO_4$) and concentrated under vacuum. The crude product is chromatographed on silica gel using a solvent ethyl acetate as eluent to give the product.

Step 4-Step 6 are performed in a manner similar to that described in the Example for preparation of 1,2-dithiolane serinol.

Example 18

Preparation of Diamino-N,N-di[4-(1,2-dithiolane)]alkane from 4-bromo-[1,2]-dithiolane

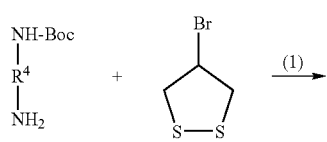

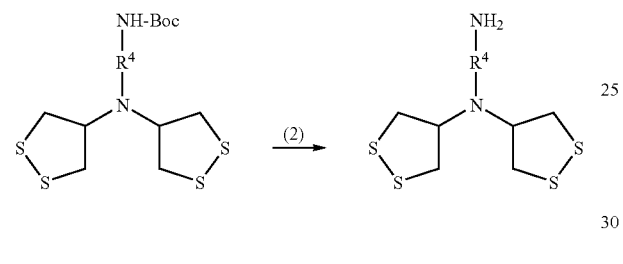

To a solution of mono-boc-diamino alkane (5 mmol) in acetonitrile (20 ml), 4-bromo-[1,2]-dithiolane (10 mmol) is added at room temperature. The mixture is warmed to 50° C., stirred for 2 h, and further stirred for 2 days at room temperature, and then poured into water. After extraction with $CH_2Cl_2$, the organic extracts are dried over $Na_2SO_4$. The solvent is evaporated and the crude product is purified by column chromatography on silica gel (eluant: ethyl acetate). The deprotection and purification of the product are performed in a manner similar to that described in the Example for preparation of 1,2-dithiolane serinol.

Example 19

Preparation of diamino-N,N-di[(1,2-dithiolane)]pentyl from 4-bromo-[1,2]-dithiolane

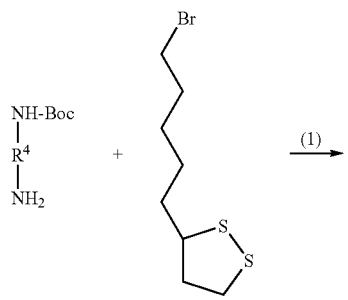

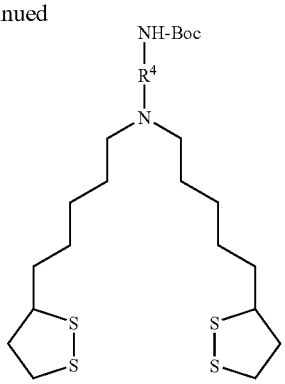

The preparation is performed in a manner similar to that described above.

Example 20

Preparation of a 1,2-Dithiolane

To a solution of serinol (5 mmol) in acetonitrile (20 ml), 4-bromo-[1,2]-dithiolane (10 mmol) is added at room temperature. The mixture is warmed to 50° C., stirred for 2 h, and further stirred for 2 days at room temperature, and then poured into water. After extraction with $CH_2Cl_2$, the organic extracts are dried over $Na_2SO_4$. The solvent is evaporated and the crude product is purified by column chromatography on silica gel (eluant:ethyl acetate).

Example 21

Preparation of a 1,2-Dithiolane

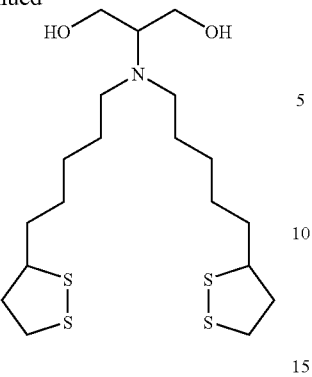

The compound is prepared in a manner similar to that described above.

Example 22

Preparation of a 1,2-Dithiolane

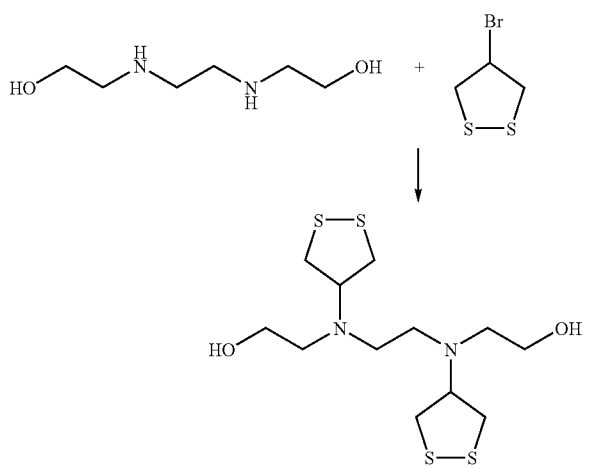

The compound is prepared in a manner similar to that described above.

Example 23

Preparation of 1,2-Dithiolane(bis-acrylatel)

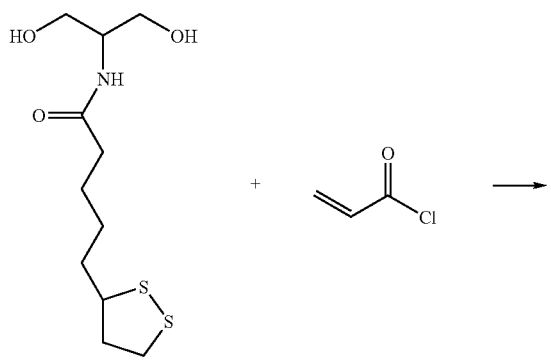

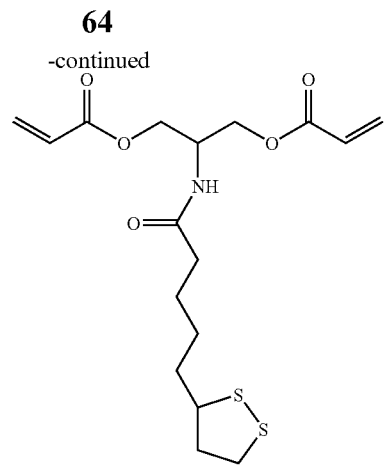

To a solution of Lipoic acid/Serinol (3.6 mmol) in 15 mL of anhydrous $CH_2Cl_2$ potassium carbonate (18 mmol) is added, and the mixture is cooled to 0° C. Subsequently, acryloyl chloride (18 mmol) is added dropwise within 15 min. After the mixture is stirred for 1 h at 0° C. and 48 h at room temperature, the reaction mixture is washed with deionized water (3×50 mL), dried with $MgSO_4$ and the volume is reduced under vacuum (5 mL). The crude product is purified by silicagel column chromatography (100 mL) eluting with $CHCl_3$:MeOH (95:1).

Example 24

Synthesis of Polymer

The inventive polymers may be prepared by any method known in the art. Preferably the polymers are prepared from commercially available starting materials. In another embodiment, the polymers are prepared from easily and/or inexpensively prepared starting materials.

The synthesized polymer may be purified by any technique known in the art including precipitation, crystallization, chromatography, etc.

Example 25

Preparation of the Particles

The inventive nano- and microparticles may be prepared using any method known in the art including spray drying, single and double emulsion solvent evaporation, solvent extraction, and other methods well known to those of ordinary skill in the art.

The surface charge of particles prepared with the inventive polymers may be controlled by the amount of the tertiary amine containing segment.

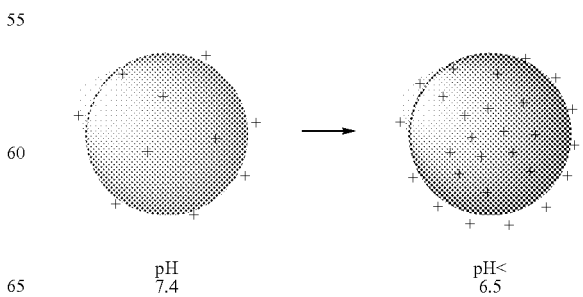

The interaction of the positively charged particles with the endolysosomal membrane may be enhanced resulting in membrane disrupture and release of the particles into the cytoplasm.

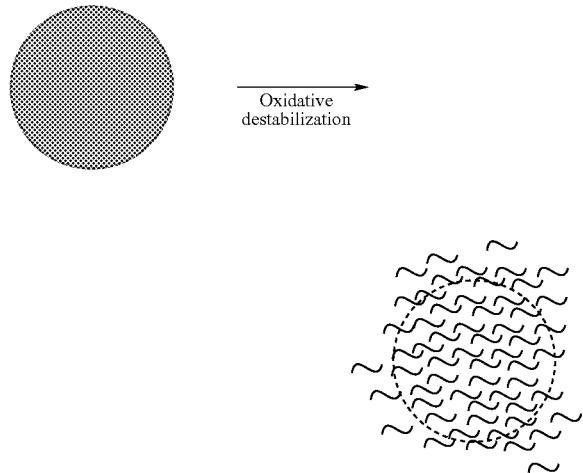

The oxidation of the dithiolane sulfer atoms to thiosulfinate will make the dithiolane containing polymers less hydrophobic, thus making them more water soluble, leading to the destabilization of the particles. The loaded drugs/therapeutics will be then released in a controlled manner in the environment of oxidative stress.

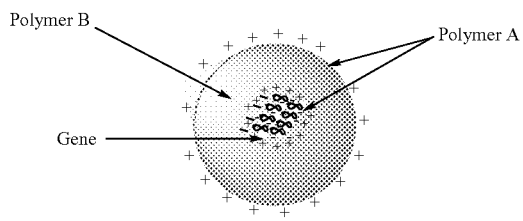

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A compound selected from the group consisting of:
a compound having

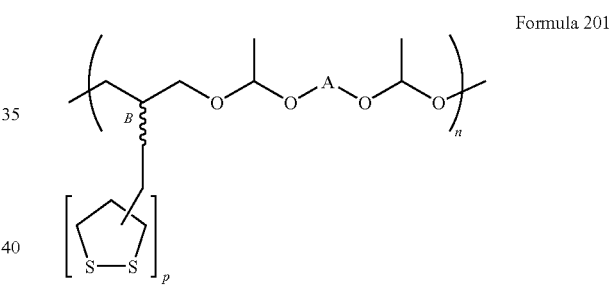

Formula 201 wherein n is an integer of at least 2, P is an integer between 1 and 2, and A and B are each independently selected from the group consisting of a branched or unbranched alkyl, aryl, cycloaliphatic and aralkyl group, is saturated or unsaturated, and optionally comprises hetero atoms;

a compound having

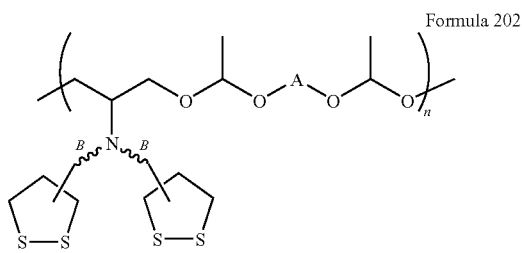

Formula 202 wherein n is an integer of at least 2, and A and B are each independently selected from the group consisting of a branched or unbranched alkyl, aryl, cycloaliphatic and aralkyl group, is saturated or unsaturated, and optionally comprises hetero atoms;

a compound having

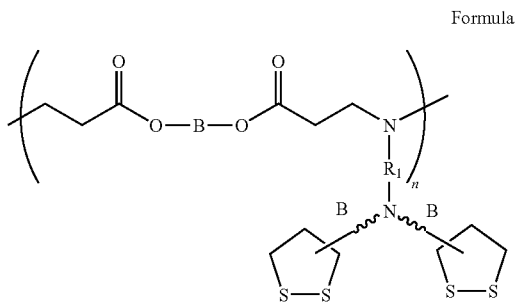

Formula 203 wherein n is an integer of at least 2, $R_1$ is selected from the group consisting of a branched or unbranched alkyl, aryl, cycloaliphatic and aralkyl group, is saturated or unsaturated, and optionally comprises hetero atoms, and B is selected from the group consisting of a branched or unbranched alkyl, aryl, cycloaliphatic and aralkyl group, is saturated or unsaturated, and optionally comprises hetero atoms;

a compound having

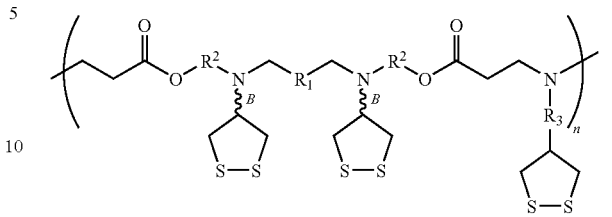

Formula 204 wherein n is an integer of at least 2, $R_1$, $R_2$ and $R_3$ are each independently selected from the group consisting of a branched or unbranched alkyl, aryl, cycloaliphatic and aralkyl group, is saturated or unsaturated, and optionally comprises hetero atoms, and B is selected from the group consisting of a branched or unbranched alkyl, aryl, cycloaliphatic and aralkyl group, is saturated or unsaturated, and optionally comprises hetero atoms;

a compound having

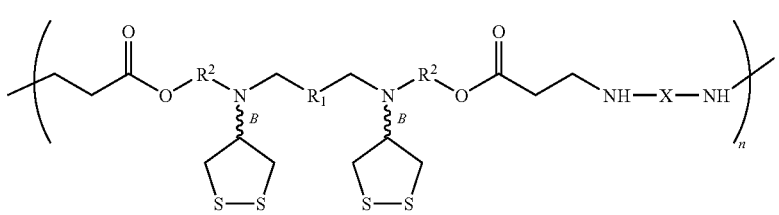

Formula 205 wherein n is an integer of at least 2, and $R_1$, $R_2$, B and X are each independently selected from the group consisting of a branched or unbranched alkyl, aryl, cycloaliphatic and aralkyl group, is saturated or unsaturated, and optionally comprises hetero atoms;

a compound having

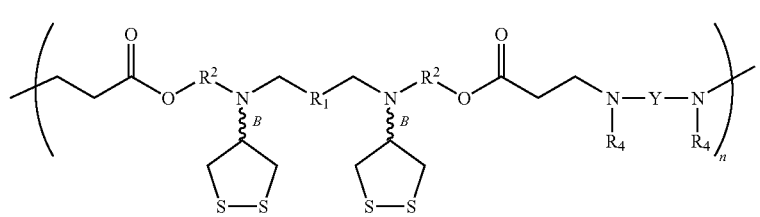

Formula 206 wherein n is an integer of at least 2, $R_1$, $R_2$, B and Y are each independently selected from the group consisting of a branched or unbranched alkyl, aryl, cycloaliphatic and aralkyl group, is saturated or unsaturated, and optionally comprises hetero atoms, and $R_4$ is selected from the group consisting of hydrogen and a branched and unbranched alkyl, aryl, cycloaliphatic or aralkyl group, is saturated or unsaturated, and optionally comprises hetero atoms;

a compound having

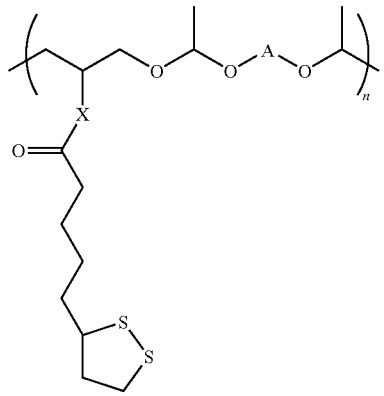
Formula 207 wherein n is an integer of at least 2, X is selected from the group consisting of —O— and —NH—, and A is selected from the group consisting of —(CH$_2$)$_a$—, and —CH$_2$CH$_2$(OCH$_2$CH$_2$)$_b$—, wherein a is an integer of 2 to 18, and b is an integer of 1 to 100;

a compound having

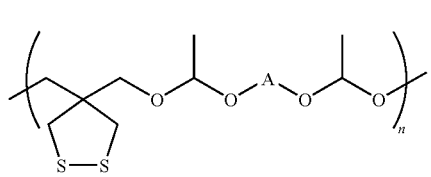
Formula 208 wherein n is an integer of at least 2,

A is selected from the group consisting of —(CH$_2$)$_a$—, and —CH$_2$CH$_2$(OCH$_2$CH$_2$)$_b$—, wherein a is an integer of 2 to 18, and b is an integer from 1 to 100;

a compound having

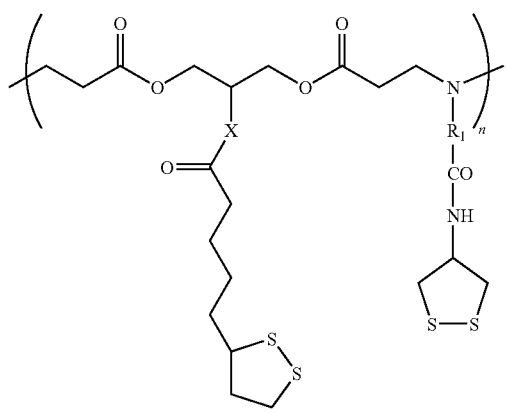
Formula 216 wherein n is an integer of at least 2, R$_1$ is an alkyl group of 1 to 6 carbon atoms, and X is selected from the group consisting of —O— and —NH—;

a compound having

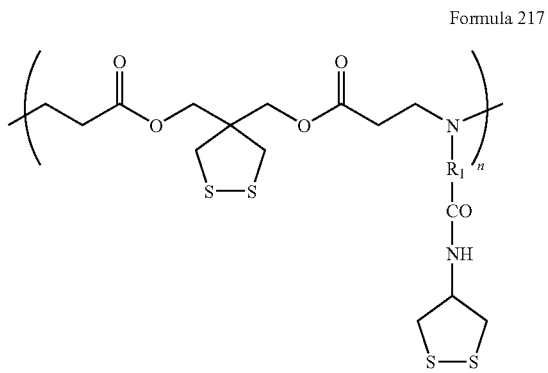
Formula 217 wherein n is an integer of at least 2, and R$_1$ is an alkyl group of 1 to 6 carbon atoms;

a compound having

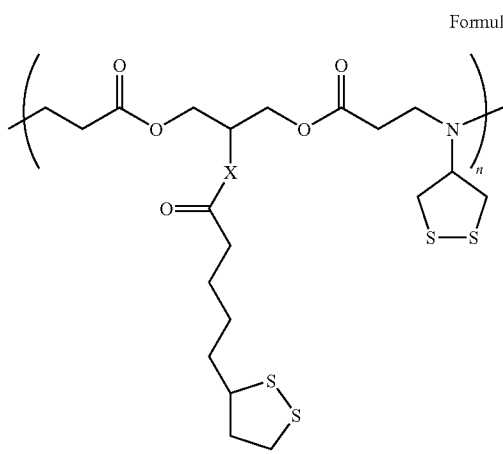
Formula 225 wherein n is an integer between 3 to 100, and X is selected from the group consisting of —O— and —NH—;

a compound having

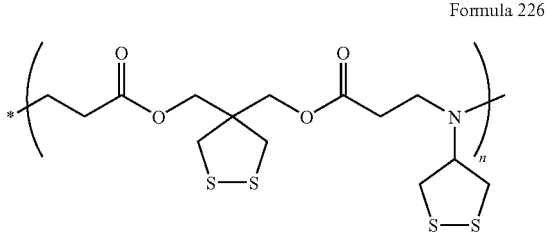
Formula 226 wherein n is an integer between 3 to 100;

a compound having

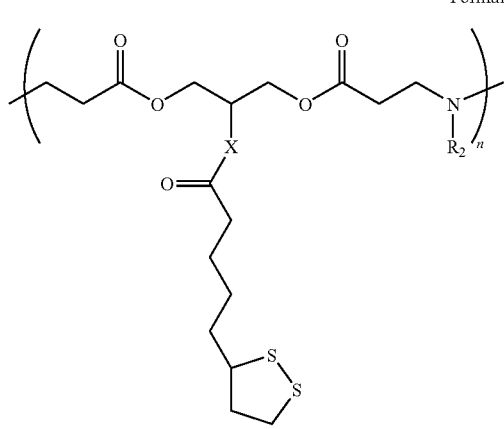

Formula 227 wherein n is an integer of at least 2, X is selected from the group consisting of —O— and —NH—, and $R_2$ is selected from the group consisting of a branched or unbranched alkyl, aryl, cycloaliphatic and aralkyl group, is saturated or unsaturated, and optionally comprises hetero atoms;

a compound having

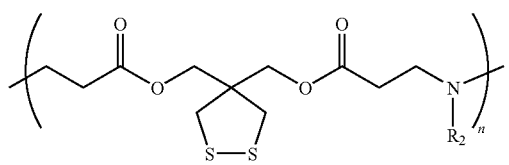

Formula 228 wherein n is an integer of at least 2, and $R_2$ is selected from the group consisting of a branched or unbranched alkyl, aryl, cycloaliphatic and aralkyl group, is saturated or unsaturated, and optionally comprises hetero atoms;

a compound having

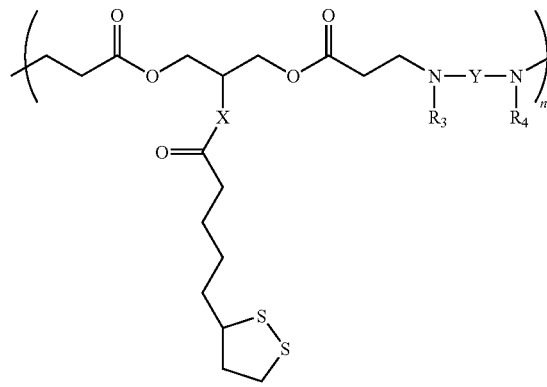

Formula 229 wherein n is an integer of at least 2, X is selected from the group consisting of —O— and —NH—, Y is selected from the group consisting of a branched or unbranched alkyl, aryl, cycloaliphatic and aralkyl group, is saturated or unsaturated, and optionally comprises hetero atoms, and $R_3$ and $R_4$ are each independently selected from the group consisting of hydrogen, and a branched or unbranched alkyl, aryl, cycloaliphatic or aralkyl group, is saturated or unsaturated, and optionally comprises hetero atoms;

a compound having

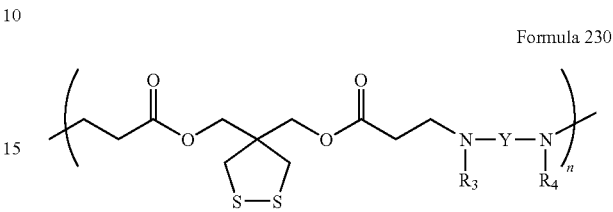

Formula 230 wherein n is an integer of at least 2, Y is selected from the group consisting of a branched or unbranched alkyl, aryl, cycloaliphatic and aralkyl group, is saturated or unsaturated, and optionally comprises hetero atoms, and $R_3$ and $R_4$ are each independently selected from the group consisting of hydrogen and a branched or unbranched alkyl, aryl, cycloaliphatic or aralkyl group, is saturated or unsaturated, and optionally comprises hetero atoms;

a compound having

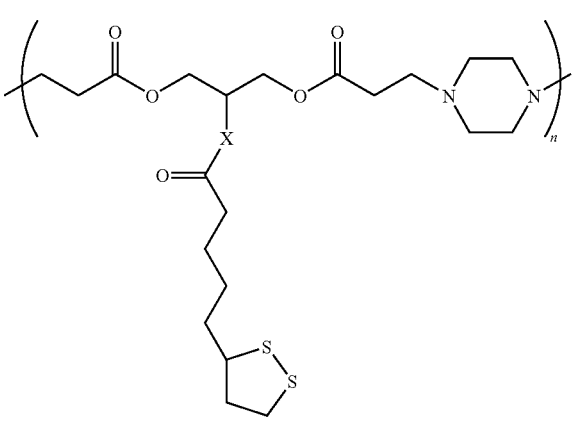

Formula 231 wherein n is an integer of at least 2, and X is selected from the group consisting of —O— and —NH—;

a compound having

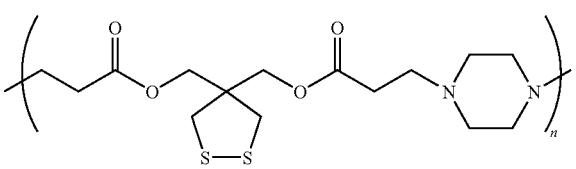

Formula 232 wherein n is an integer of at least 2; and
a compound having

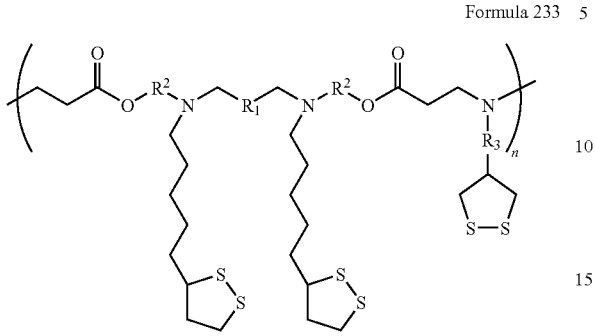

Formula 233 wherein n is an integer of at least 2, $R_1$, $R_2$ and $R_3$ are each independently selected from the group consisting of a branched or unbranched alkyl, aryl, cycloaliphatic and aralkyl group, is saturated or unsaturated, and optionally comprises hetero atoms.

2. The compound of claim 1 having Formula 207, wherein A is —$(CH_2)_2$— and n is an integer between 3 to 100.

3. The compound of claim 1 having Formula 207, wherein A is —$(CH_2)_4$— and n is an integer between 3 to 100.

4. The compound of claim 1 having Formula 207, wherein A is —$CH_2CH_2OCH_2CH_2$— and n is an integer between 3 to 100.

5. The compound of claim 1 having Formula 207, wherein A is —$CH_2CH_2(OCH_2CH_2)_2$— and n is an integer between 3 to 100.

6. The compound of claim 1 having Formula 208, wherein A is —$(CH_2)_2$— and n is an integer between 3 to 100.

7. The compound of claim 1 having Formula 208, wherein A is —$(CH_2)_4$— and n is an integer between 3 to 100.

8. The compound of claim 1 having Formula 208, wherein A is —$CH_2CH_2OCH_2CH_2$— and n is an integer between 3 to 100.

9. The compound of claim 1 having Formula 208, wherein A is —$CH_2CH_2(OCH_2CH_2)_2$— and n is an integer between 3 to 100.

10. A compound having

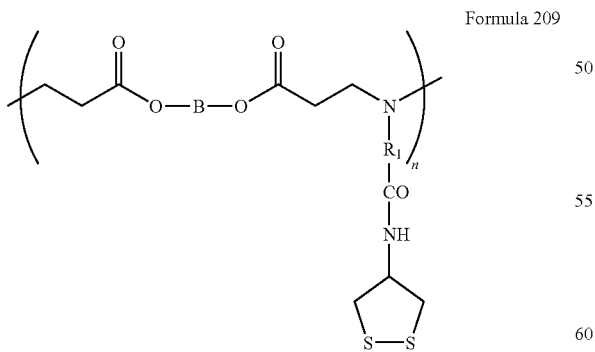

Formula 209 wherein n is an integer of at least 2, B is selected from the group consisting of a branched or unbranched alkyl, aryl, cycloaliphatic and aralkyl group, is saturated or unsaturated, and optionally comprises hetero atoms, and $R_1$ is an alkyl group of 1 to 6 carbon atoms.

11. The compound of claim 10, having a formula selected from the group consisting of:

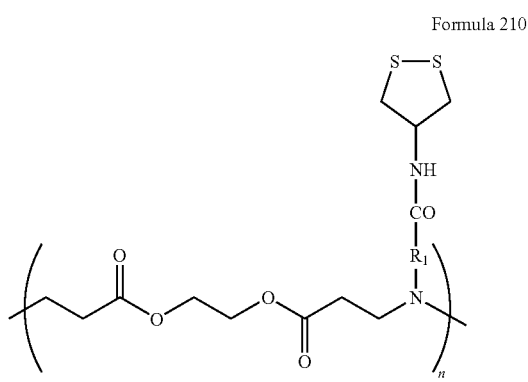

Formula 210 wherein n is an integer between 3 to 100;

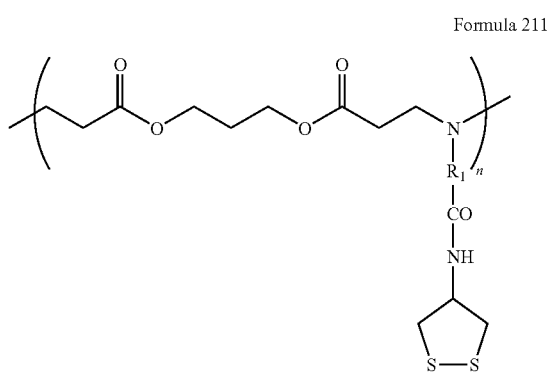

Formula 211 wherein n is an integer between 3 to 100;

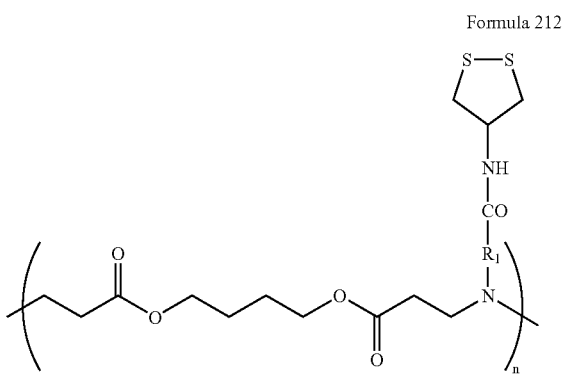

Formula 212 wherein n is an integer between 3 to 100;

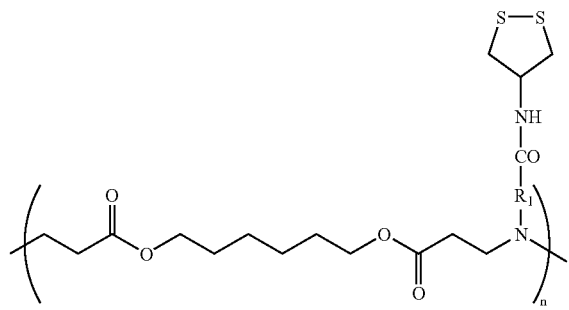

Formula 213

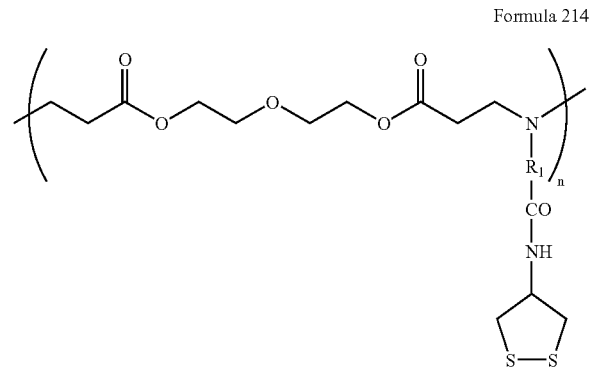

Formula 214 wherein n is an integer between 3 to 100;

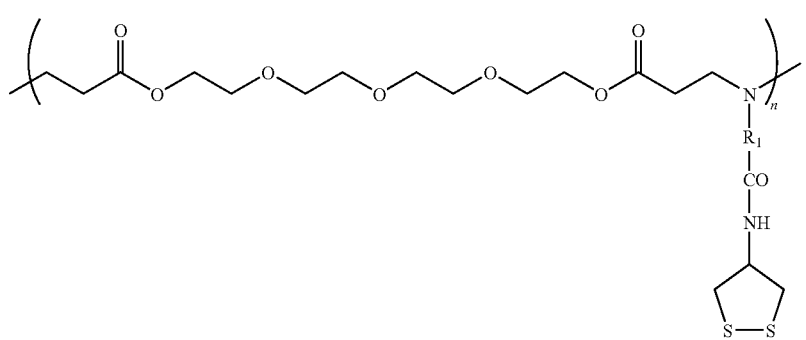

Formula 215 wherein n is an integer between 3 to 100.

12. The compound of claim 10, wherein B is a poly(ethylene glycol) divinyl ether with a molecular weight of about 200 to about 5,000 Daltons.

13. The compound of claim 10, wherein B is a poly(ethylene glycol) with a molecular weight of about 200 to about 5,000 Daltons, and n is an integer between 3 to 100.

14. The compound of claim 10, wherein B is poly(propylene glycol) with a molecular weight of about 200 to about 5,000 Daltons, and n is an integer between 3 to 100.

15. A compound having

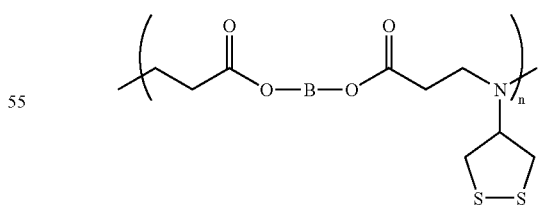

Formula 218 wherein n is an integer of at least 2, and

B is selected from the group consisting of a branched or unbranched alkyl, aryl, cycloaliphatic and aralkyl group, is saturated or unsaturated, and optionally comprises hetero atoms.

16. The compound of claim 15 having a formula selected from the group consisting of:

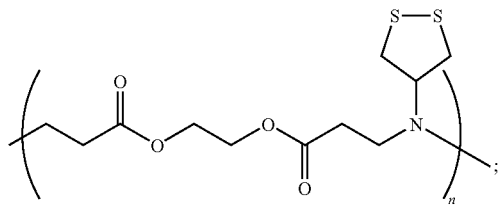
Formula 219

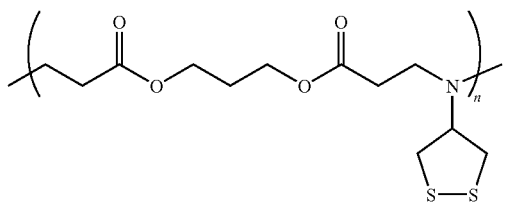
Formula 220

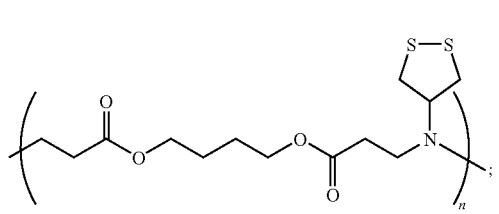
Formula 221

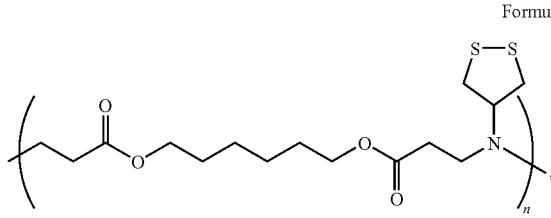
Formula 222

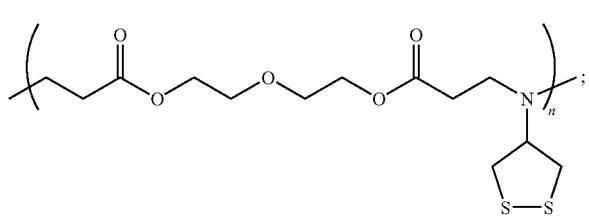
Formula 223

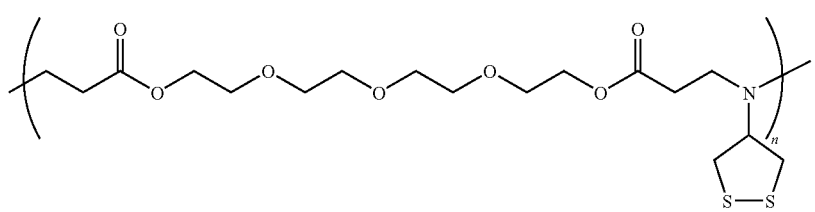
Formula 224 wherein n is an integer between 3 to 100.

17. The compound of claim 15, wherein B is poly(ethylene glycol) with a molecular weight of about 200 to about 5,000 Daltons, and n is an integer between 3 to 100.

18. The compound of claim 15, wherein B is a poly(propylene glycol) with a molecular weight of about 200 to about 5,000 Daltons, and n is an integer between 3 to 100.

19. The compound of claim 1 having Formula 227, wherein $R_2$ is an alkyl group of 2-18 carbon atoms.

20. The compound of claim 1 having Formula 227, wherein $R_2$ is a poly(ethylene glycol) with a molecular weight of about 200 to about 5,000 Daltons, and n is an integer between 3 to 100.

21. The compound of claim 1 having Formula 228, wherein $R_2$ is an alkyl group of 2-18 carbon atoms.

22. The compound of claim 1 having Formula 228, wherein $R_2$ is a poly(ethylene glycol) with a molecular weight of up to 5,000 Daltons, and n is an integer between 3 to 100.

23. The compound of claim 1 having Formula 229, wherein Y is an alkyl group of 2-18 carbon atoms, $R_3$ and $R_4$ are hydrogen, and n is an integer between 3 to 100.

24. The compound of claim 1 having Formula 229, wherein Y is an alkyl group of 2-18 carbon atoms, $R_3$ and $R_4$ are methyl groups, and n is an integer between 3 to 100.

25. The compound of claim 1 having Formula 229, wherein Y is an alkyl group of 2-18 carbon atoms, $R_3$ and $R_4$ are ethyl groups, and n is an integer between 3 to 100.

26. The compound of claim 1 having Formula 229, wherein Y is an alkyl group of 2-18 carbon atoms, $R_3$ and $R_4$ are hydroxyethyl groups, and n is an integer between 3 to 100.

27. The compound of claim 1 having Formula 229, wherein and $R_3$ and $R_4$ are hydrogen atoms, Y is a poly(ethylene glycol) with a molecular weight of up to 5,000 Daltons, and n is an integer between 3 to 100.

28. The compound of claim 1 having Formula 230, wherein Y is an alkyl group of 2-18 carbon atoms, $R_3$ and $R_4$ are hydrogens, and n is an integer between 3 to 100.

29. The compound of claim 1 having Formula 230, wherein Y is an alkyl group of 2-18 carbon atoms, $R_3$ and $R_4$ are methyl groups, and n is an integer between 3 to 100.

30. The compound of claim 1 having Formula 230, wherein Y is an alkyl group of 2-18 carbon atoms, $R_3$ and $R_4$ are ethyl groups, and n is an integer between 3 to 100.

31. The compound of claim 1 having Formula 230, wherein Y is an alkyl group of 2-18 carbon atoms, $R_3$ and $R_4$ are hydroxyethyl groups, and n is an integer between 3 to 100.

32. The compound of claim 1 having Formula 230, wherein $R_3$ and $R_4$ are hydrogen atoms, Y is a poly(ethylene glycol) with a molecular weight in the range of up to 5,000 Daltons, and n is an integer between 3 to 100.

33. The compound of claim 1 having Formula 231 or Formula 232, wherein n is an integer between 3 to 100.

34. A compound comprising polyvinyl alcohol-(α-lipoic acid) conjugate having

35. A compound selected from the group consisting of:
a compound having

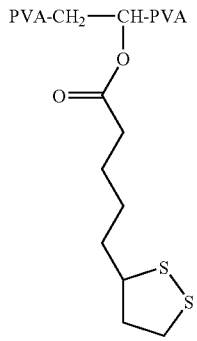

Formula 234

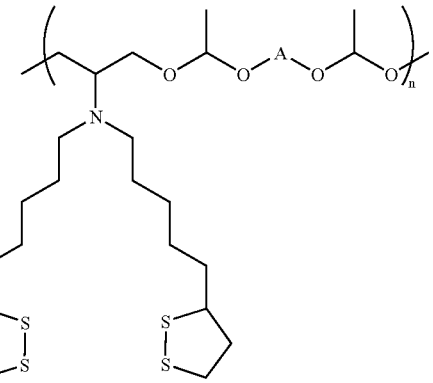

Formula 235 wherein PVA is polyvinyl alcohol polymer and α-lipoic acid and is linked via an ester bond to the hydroxyl group of a monomeric unit of PVA.

wherein n is an integer of at least 2, and A is selected from the group consisting of a branched or unbranched alkyl, aryl, cycloaliphatic and aralkyl group, is saturated or unsaturated, and optionally comprises hetero atoms;
a compound having

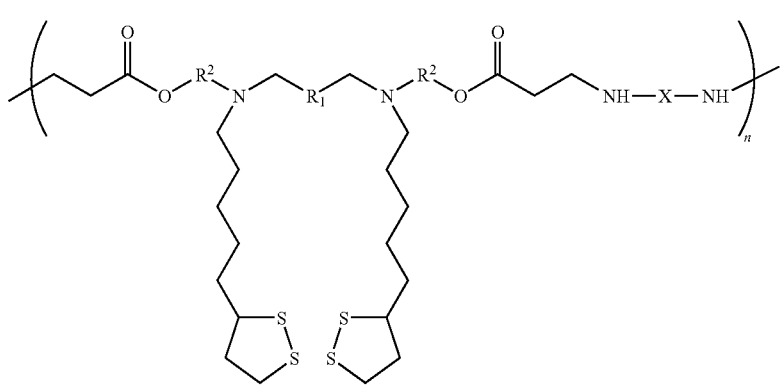

Formula 236 wherein n is an integer of at least 2, $R_1$ and $R_2$ are each independently selected from the group consisting of a branched or unbranched alkyl, aryl, cycloaliphatic and aralkyl group, is saturated or unsaturated, and optionally comprises hetero atoms, and X is selected from the group consisting of a branched or unbranched alkyl, aryl, cycloaliphatic and aralkyl group, is saturated or unsaturated, and optionally comprises hetero atoms; and
a compound having

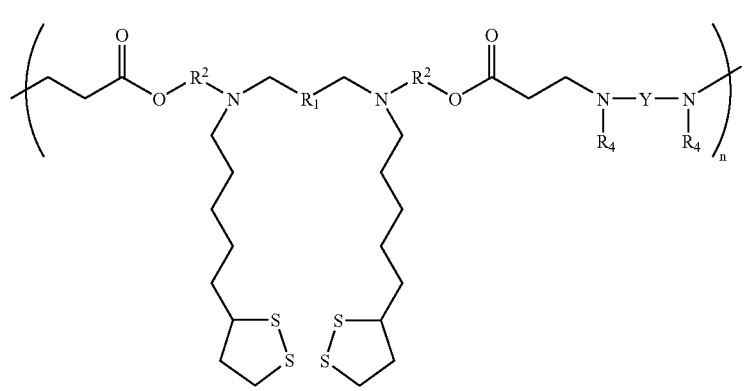

Formula 237 wherein n is an integer of at least 2, $R_1$ and $R_2$ are each independently selected from the group consisting of a branched or unbranched alkyl, aryl, cycloaliphatic and aralkyl group, is saturated or unsaturated, and optionally comprises hetero atoms, $R_4$ is selected from the group consisting of hydrogen and a branched and unbranched alkyl, aryl, cycloaliphatic or aralkyl group, is saturated or unsaturated, and optionally comprises hetero atoms, and Y is selected from the group consisting of a branched or unbranched alkyl, aryl, cycloaliphatic and aralkyl group, is saturated or unsaturated, and may optionally comprise hetero atoms.

36. A compound comprising a poly-α-aspartic acid-(1,2-dithiolane Derivative) conjugate having

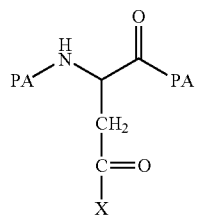

Formula 238 wherein PA is a poly-α-aspartic acid polymer and

X is a 1,2-dithiolane derivative selected from the group consisting of

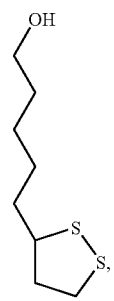

Formula A

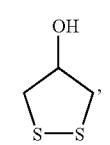

Formula B

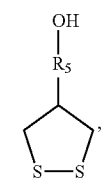

Formula C

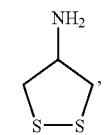

Formula D

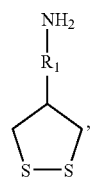

Formula E

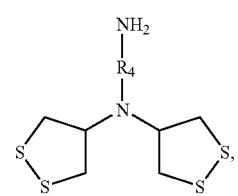

Formula F

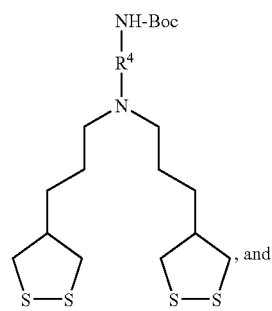

Formula G

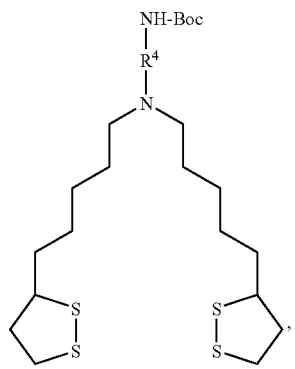

, and

Formula H

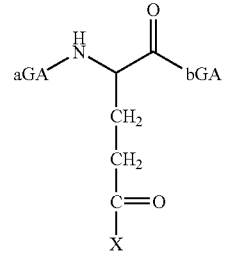

wherein $R_1$, $R_4$ and $R_5$ are each independently selected from the group consisting of a branched or unbranched alkyl, aryl, cycloaliphatic and aralkyl group, is saturated or unsaturated, and optionally comprises hetero atoms.

37. The compound of claim 36, wherein $R_5$ is an alkyl group of 2-18 carbon atoms.

38. The compound of claim 36, wherein the polymer has a molecular weight of about 750 to about 100,000 Daltons.

39. The compound of claim 36, wherein the weight % ratio of the 1,2-dithiolane derivative to the PA is at least 10%.

40. A compound comprising a poly-α-glutamic acid-(1,2-dithiolane derivative) conjugate having Formula 239 wherein aGA is a poly-α-glutamic acid polymer, and
X is a 1,2-dithiolane derivative selected from the group consisting of

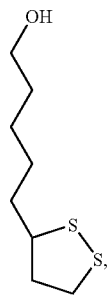
Formula A

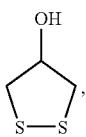
Formula B

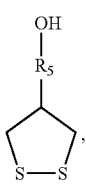
Formula C

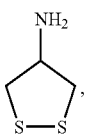
Formula D

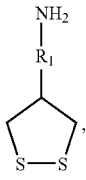
Formula E

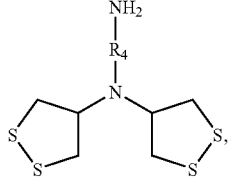
Formula F

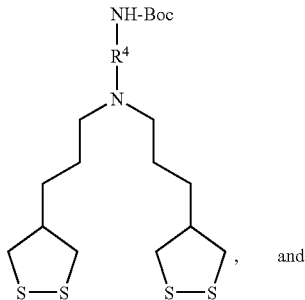
Formula G, and

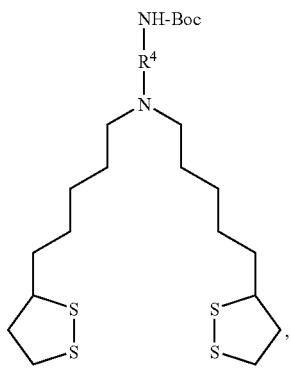
Formula H wherein $R_1$, $R_4$, and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the aGA.

41. The compound of claim 40, wherein the polymer has a molecular weight of about 750 to about 100,000 Daltons.

42. The compound of claim 40, wherein the weight % ratio of the 1,2-dithiolane derivative to the aGA is at least 10%.

43. A compound comprising a poly-γ-glutamic acid-(1,2-dithiolane derivative) conjugate having

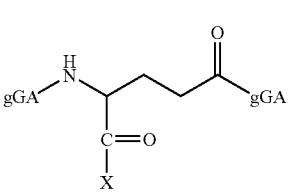
Formula 240 wherein gGA is a poly-γ-glutamic acid polymer, and
X is a 1,2-dithiolane derivative selected from the group consisting of

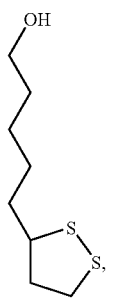
Formula A

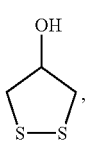
Formula B

-continued

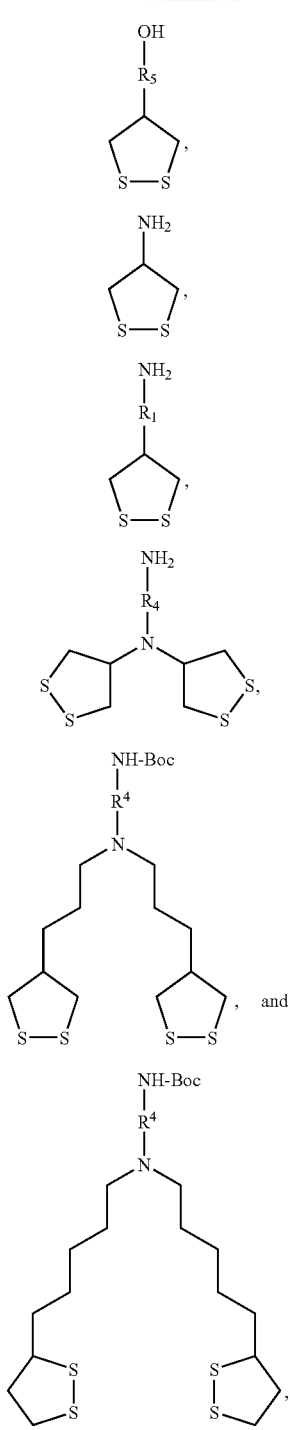

wherein $R_1$, $R_4$, and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the gGA.

44. The compound of claim 43, wherein the polymer has a molecular weight in the range of about 750 to about 100,000 Daltons.

45. The compound of claim 43, wherein the weight % ratio of the 1,2-dithiolane derivative to the gGA is at least 10%.

46. A compound comprising a poly-β-malic acid acid-(1,2-dithiolane derivative) conjugate having

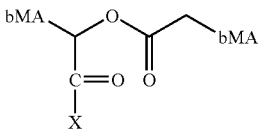

Formula 241 wherein bMA is a poly-β-malic acid acid polymer, and X is a 1,2-dithiolane derivative selected from the group consisting of Formula A

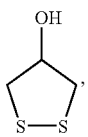

Formula B

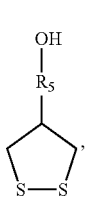

Formula C

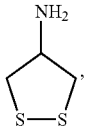

Formula D

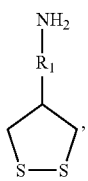

Formula E

Formula F

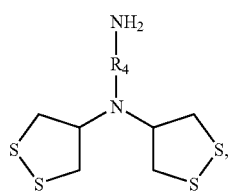

-continued

Formula G

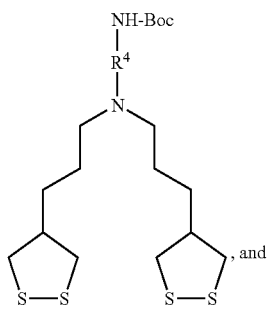, and

Formula H

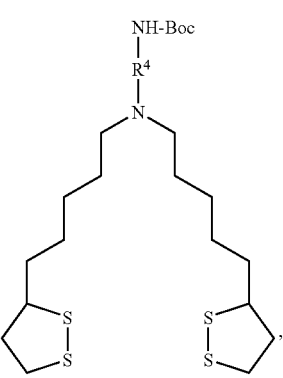, wherein $R_1$, $R_4$, and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the bMA.

47. The compound of claim 46, wherein the polymer has a molecular weight in the range of about 750 to about 100,000 Daltons.

48. The compound of claim 46, wherein the weight % ratio of the 1,2-dithiolane derivative to the bMA is at least 10%.

49. A compound comprising a polyacrylic acid-(1,2-dithiolane derivative) conjugate having Formula 242

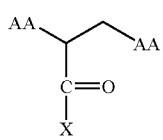

wherein AA is a polyacrylic acid polymer, and
X is a 1,2-dithiolane derivative selected from the group consisting of Formula A

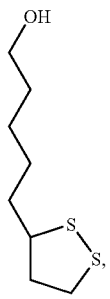,

Formula B

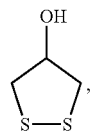,

Formula C

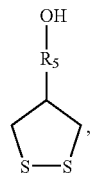,

Formula D

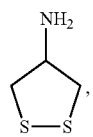,

Formula E

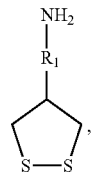,

Formula F

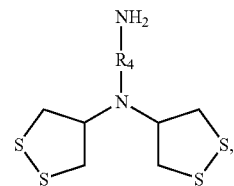,

Formula G

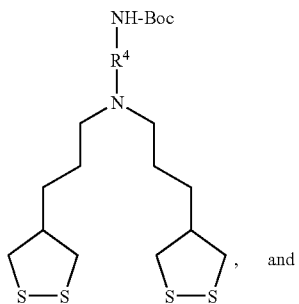, and

-continued

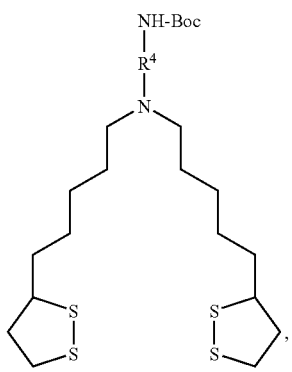

Formula H wherein $R_1$, $R_4$, and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the AA.

50. The compound of claim 49, wherein the polymer has a molecular weight of about 750 to about 100,000 Daltons.

51. The compound of claim 49, wherein the weight % ratio of the 1,2-dithiolane derivative to the AA is at least 10%.

52. A compound comprising a polymethacrylic acid-(1,2-dithiolane derivative) conjugate having

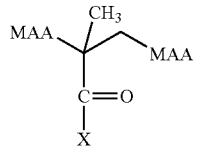

Formula 243 wherein MAA is a polymethacrylic acid polymer, and

X is a 1,2-dithiolane derivative selected from the group consisting of

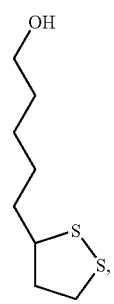

Formula A

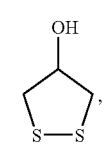

Formula B

-continued

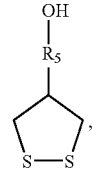

Formula C

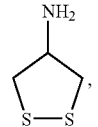

Formula D

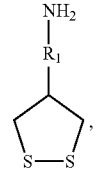

Formula E

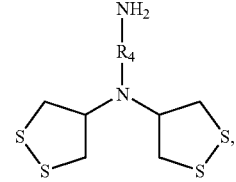

Formula F

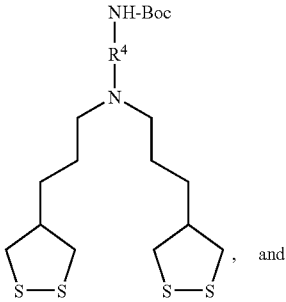

, and

Formula G

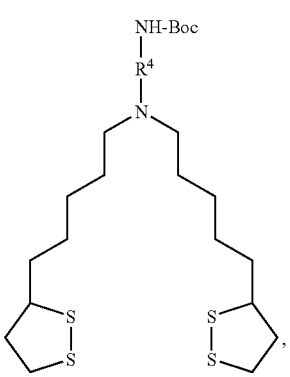

Formula H wherein $R_1$, $R_4$, and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the MAA.

53. The compound of claim 52, wherein the polymer has a molecular weight of about 750 to about 100,000 Daltons.

54. The compound of claim 52, wherein the weight % ratio of the 1,2-dithiolane derivative to the MAA is at least 10%.

55. A compound comprising a linear polyethyleneimine-(α-lipoic acid) conjugate having

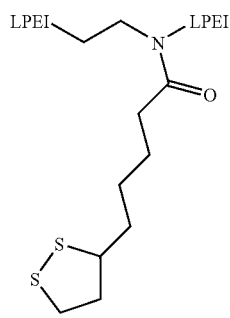

Formula 244 wherein LPEI is a linear polyethyleneimine polymer and the α-lipoic acid is linked via an amide bond to the amine group of a monomeric unit of the LPEI.

56. The compound of claim 55, wherein the polymer has a molecular weight of about 750 to about 100,000 Daltons.

57. The compound of claim 55, wherein the weight % ratio of the α-lipoic acid to the LPEI is at least 10%.

58. A compound comprising a chitosan-(α-lipoic acid) conjugate having

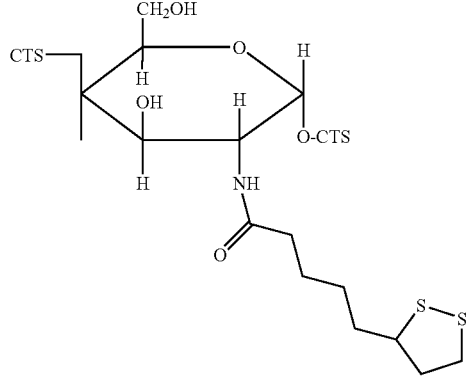

Formula 245 wherein CTS is a chitosan polymer and the α-lipoic acid is linked via an amide bond to the amine group of a monomeric unit of the CTS.

59. The compound of claim 58, wherein the polymer has a molecular weight of about 750 to about 100,000 Daltons.

60. The compound of claim 58, wherein the weight % ratio of the α-lipoic acid to the CTS is at least 10%.

61. A compound comprising a poly(amido amide) (PAMAM)-(α-lipoic acid) dendrimer conjugate wherein the α-lipoic acid is linked via an amide bond to the surface primary amine linker units of the PAMAM dendrimer.

62. The compound of claim 61, wherein the PAMAM dendrimer is selected from the group consisting of a generation 0 dendrimer, a generation 1 dendrimer, a generation 2 dendrimer, a generation 3 dendrimer, a generation 4 dendrimer, and a generation 5 dendrimer.

63. The compound of claim 61, wherein the weight % ratio of the α-lipoic acid to the PAMAM dendrimer is at least 10%.

64. A compound comprising a poly(amido amide) (PAMAM)-(α-lipolol) conjugate wherein α-lipoic acid is linked via an ester bond to the surface carboxylic acid linker units of the PAMAM dendrimer.

65. The compound of claim 64, wherein the PAMAM dendrimer is selected from the group consisting of a generation 0 dendrimer, a generation 1 dendrimer, a generation 2 dendrimer, a generation 3 dendrimer, a generation 4 dendrimer, and a generation 5 dendrimer.

66. The compound of claim 64, wherein the weight % ratio of the α-lipolol to the PAMAM dendrimer is at least 10%.

67. The compound of claim 64, wherein the polymer has a molecular weight in the range of about 750 to about 100,000 Daltons.

68. The compound of claim 64, wherein the weight % ratio of the α-lipoic acid to said PVA is at least 10%.

69. A compound comprising polysaccharide-(α-lipoic acid) conjugate in which α-lipoic acid is linked via ester bond to the hydroxyl group of a monomeric unit of polysaccharide.

70. The compound of claim 69, wherein the polysaccharide is selected from the group consisting of dextran, pullulan, amylose, mannan, amylopectin, and cyclodextrin.

71. The compound of claim 69, wherein the weight % ratio of said α-lipoic acid to polysaccharide is at least 10%.

72. A method of using an antioxidant polymer to treat a condition in a subject in need thereof, comprising:
providing a composition comprising the antioxidant polymer and a pharmaceutically acceptable carrier; and
administering a therapeutically effective amount of the composition to the subject to treat the condition,
wherein the condition is selected from the group consisting of oxidative stress, skin condition caused by reactive oxygen species, and cancer,
wherein the antioxidant polymer is selected from the group consisting of:
a compound having

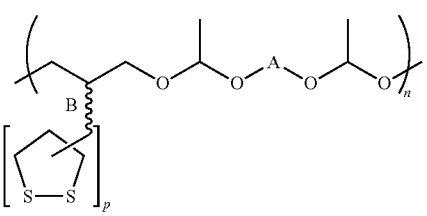

Formula 201 wherein n is an integer of at least 2, P is an integer between 1 and 2, and A and B are each independently selected from the group consisting of a branched or unbranched alkyl, aryl, cycloaliphatic and aralkyl group, is saturated or unsaturated, and optionally comprises hetero atoms;
a compound having

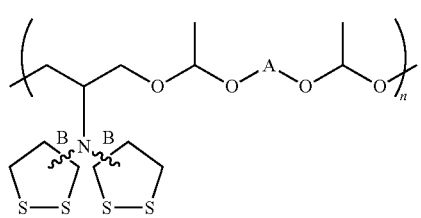

Formula 202 wherein n is an integer of at least 2, and A and B are each independently selected from the group consisting of a branched or unbranched alkyl, aryl, cycloaliphatic and aralkyl group, is saturated or unsaturated, and optionally comprises hetero atoms;

a compound having

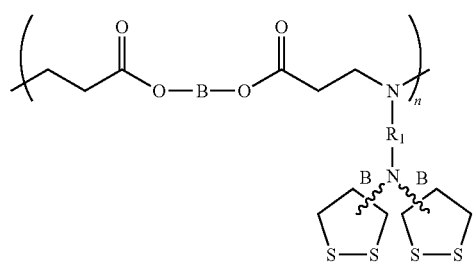

Formula 203 wherein n is an integer of at least 2, $R_1$ is selected from the group consisting of a branched or unbranched alkyl, aryl, cycloaliphatic and aralkyl group, is saturated or unsaturated, and optionally comprises hetero atoms, and B is selected from the group consisting of a branched or unbranched alkyl, aryl, cycloaliphatic and aralkyl group, is saturated or unsaturated, and optionally comprises hetero atoms;

a compound having

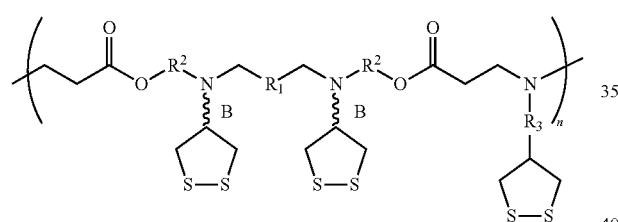

Formula 204 wherein n is an integer of at least 2, $R_1$, $R_2$ and $R_3$ are each independently selected from the group consisting of a branched or unbranched alkyl, aryl, cycloaliphatic and aralkyl group, is saturated or unsaturated, and optionally comprises hetero atoms, and B is selected from the group consisting of a branched or unbranched alkyl, aryl, cycloaliphatic and aralkyl group, is saturated or unsaturated, and optionally comprises hetero atoms;

a compound having

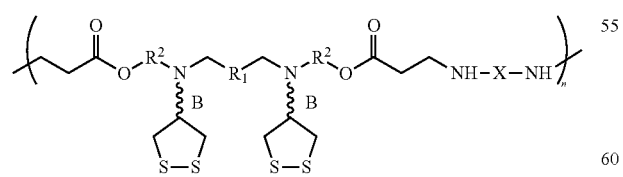

Formula 205 wherein n is an integer of at least 2, and $R_1$, $R_2$, B and X are each independently selected from the group consisting of a branched or unbranched alkyl, aryl, cycloaliphatic and aralkyl group, is saturated or unsaturated, and optionally comprises hetero atoms;

a compound having

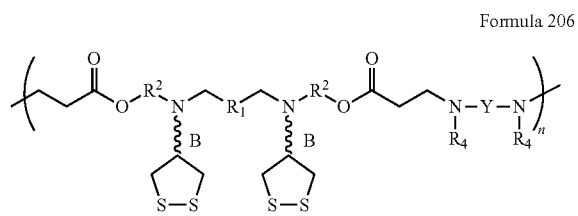

Formula 206 wherein n is an integer of at least 2, $R_1$, $R_2$, B and Y are each independently selected from the group consisting of a branched or unbranched alkyl, aryl, cycloaliphatic and aralkyl group, is saturated or unsaturated, and optionally comprises hetero atoms, and $R_4$ is selected from the group consisting of hydrogen and a branched and unbranched alkyl, aryl, cycloaliphatic or aralkyl group, is saturated or unsaturated, and optionally comprises hetero atoms;

a compound having

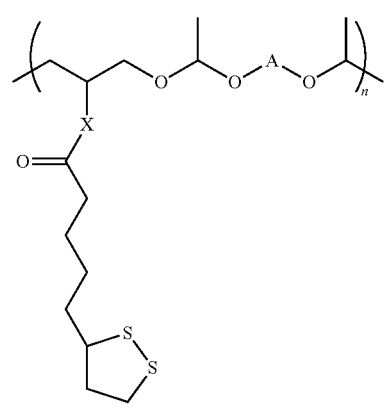

Formula 207 wherein n is an integer of at least 2, X is selected from the group consisting of —O— and —NH—, and A is selected from the group consisting of —$(CH_2)_a$—, and —$CH_2CH_2(OCH_2CH_2)_b$—, wherein a is an integer of 2 to 18, and b is an integer of 1 to 100;

a compound having

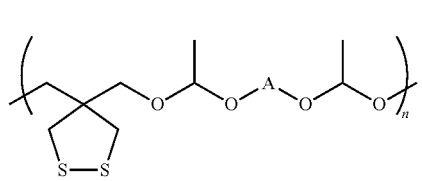

Formula 208 wherein n is an integer of at least 2,

A is selected from the group consisting of —$(CH_2)_a$—, and —$CH_2CH_2(OCH_2CH_2)_b$—, wherein a is an integer of 2 to 18, and b is an integer from 1 to 100;

a compound having

Formula 216 wherein n is an integer of at least 2, R₁ is an alkyl group of 1 to 6 carbon atoms, and X is selected from the group consisting of —O— and —NH—;

a compound having

Formula 217 wherein n is an integer of at least 2, and R₁ is an alkyl group of 1 to 6 carbon atoms;

a compound having

Formula 225 wherein n is an integer between 3 to 100, and X is selected from the group consisting of —O— and —NH—;

a compound having

Formula 226 wherein n is an integer between 3 to 100;

a compound having

Formula 227 wherein n is an integer of at least 2, X is selected from the group consisting of —O— and —NH—, and R₂ is selected from the group consisting of a branched or unbranched alkyl, aryl, cycloaliphatic and aralkyl group, is saturated or unsaturated, and optionally comprises hetero atoms;

a compound having

Formula 228 wherein n is an integer of at least 2, and R₂ is selected from the group consisting of a branched or unbranched alkyl, aryl, cycloaliphatic and aralkyl group, is saturated or unsaturated, and optionally comprises hetero atoms;

a compound having

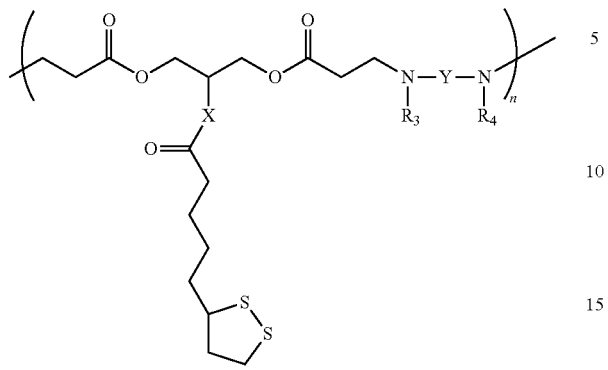

Formula 229 wherein n is an integer of at least 2, X is selected from the group consisting of —O— and —NH—, Y is selected from the group consisting of a branched or unbranched alkyl, aryl, cycloaliphatic and aralkyl group, is saturated or unsaturated, and optionally comprises hetero atoms, and $R_3$ and $R_4$ are each independently selected from the group consisting of hydrogen, and a branched or unbranched alkyl, aryl, cycloaliphatic or aralkyl group, is saturated or unsaturated, and optionally comprises hetero atoms;
a compound having

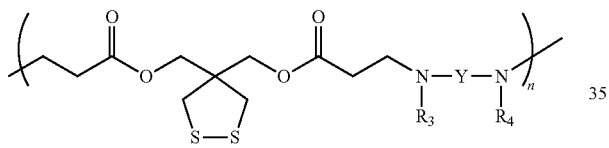

Formula 230 wherein n is an integer of at least 2, Y is selected from the group consisting of a branched or unbranched alkyl, aryl, cycloaliphatic and aralkyl group, is saturated or unsaturated, and optionally comprises hetero atoms, and $R_3$ and $R_4$ are each independently selected from the group consisting of hydrogen and a branched or unbranched alkyl, aryl, cycloaliphatic or aralkyl group, is saturated or unsaturated, and optionally comprises hetero atoms;
a compound having

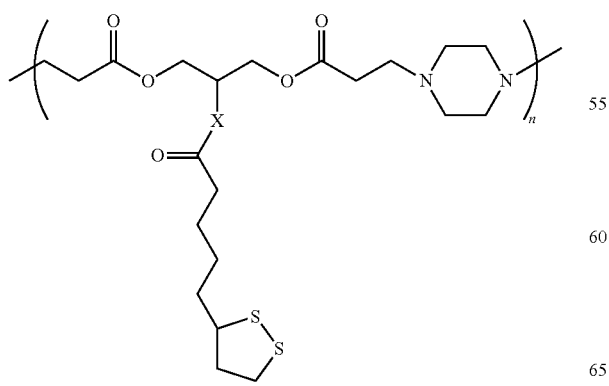

Formula 231 wherein n is an integer of at least 2, and X is selected from the group consisting of —O— and —NH—;
a compound having

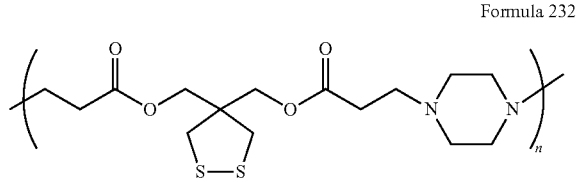

Formula 232 wherein n is an integer of at least 2; and
a compound having

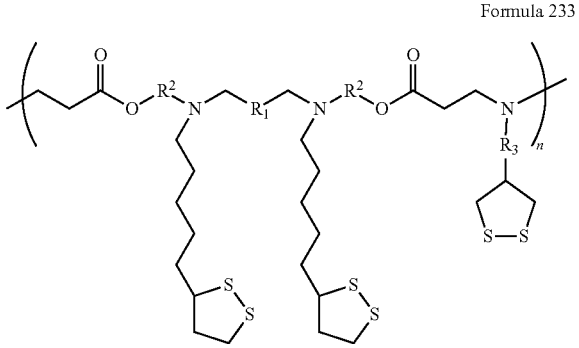

Formula 233 wherein n is an integer of at least 2, $R_1$, $R_2$ and $R_3$ are each independently selected from the group consisting of a branched or unbranched alkyl, aryl, cycloaliphatic and aralkyl group, is saturated or unsaturated, and optionally comprises hetero atoms;
a compound having

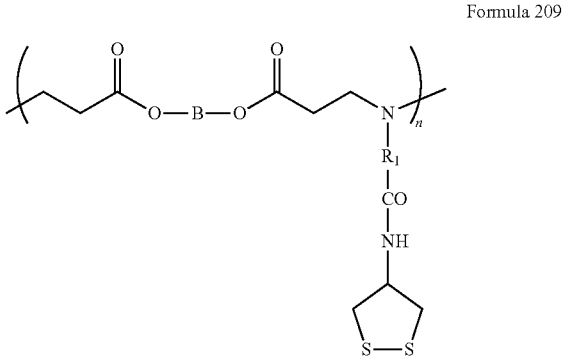

Formula 209 wherein n is an integer of at least 2, B is selected from the group consisting of a branched or unbranched alkyl, aryl, cycloaliphatic and aralkyl group, is saturated or unsaturated, and optionally comprises hetero atoms, and $R_1$ is an alkyl group of 1 to 6 carbon atoms;

a compound having

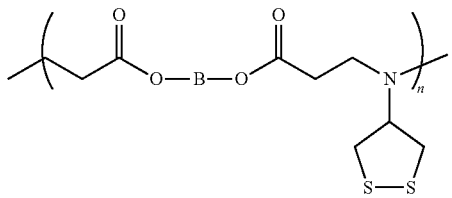

Formula 218 wherein n is an integer of at least 2, and B is selected from the group consisting of a branched or unbranched alkyl, aryl, cycloaliphatic and aralkyl group, is saturated or unsaturated, and optionally comprises hetero atoms;

a compound comprising polyvinyl alcohol-(α-lipoic acid) conjugate having

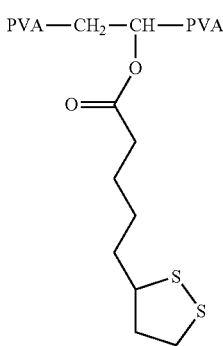

Formula 234 wherein PVA is polyvinyl alcohol polymer and α-lipoic acid and is linked via an ester bond to the hydroxyl group of a monomeric unit of PVA;

a compound having

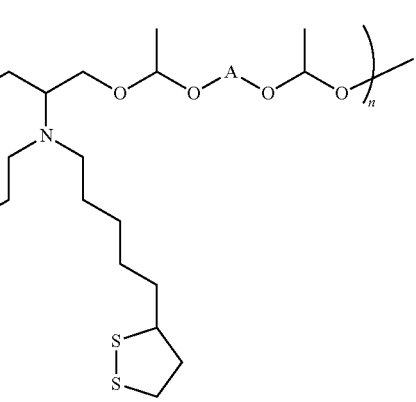

Formula 235 wherein n is an integer of at least 2, and A is selected from the group consisting of a branched or unbranched alkyl, aryl, cycloaliphatic and aralkyl group, is saturated or unsaturated, and optionally comprises hetero atoms;

a compound having

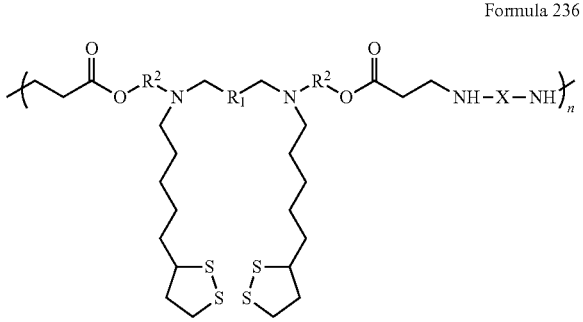

Formula 236 wherein n is an integer of at least 2, $R_1$ and $R_2$ are each independently selected from the group consisting of a branched or unbranched alkyl, aryl, cycloaliphatic and aralkyl group, is saturated or unsaturated, and optionally comprises hetero atoms, and X is selected from the group consisting of a branched or unbranched alkyl, aryl., cycloaliphatic and aralkyl group, is saturated or unsaturated, and optionally comprises hetero atoms; and a compound having

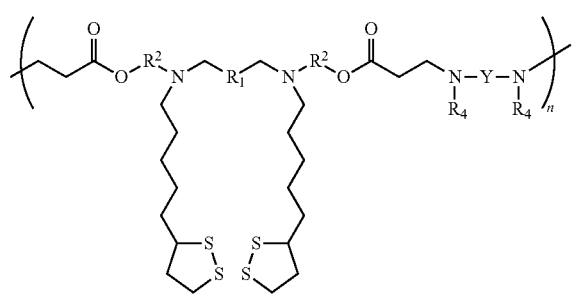

Formula 237 wherein n is an integer of at least 2, $R_1$ and $R_2$ are each independently selected from the group consisting of a branched or unbranched alkyl, aryl, cycloaliphatic and aralkyl group, is saturated or unsaturated, and optionally comprises hetero atoms, $R_4$ is selected from the group consisting of hydrogen and a branched and unbranched alkyl, aryl, cycloaliphatic or aralkyl group, is saturated or unsaturated, and optionally comprises hetero atoms, and Y is selected from the group consisting of a branched or unbranched alkyl, aryl, cycloaliphatic and aralkyl group, is saturated or unsaturated, and may optionally comprise hetero atoms;

a compound comprising a poly-α-aspartic acid-(1,2-dithiolane derivative) conjugate having Formula 238

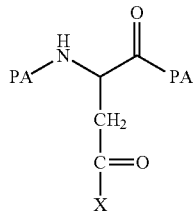

wherein PA is a poly-α-aspartic acid polymer and
X is a 1,2-dithiolane derivative selected from the group consisting of Formula A

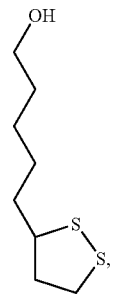

Formula B

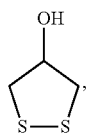

Formula C

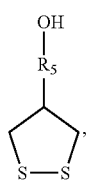

Formula D

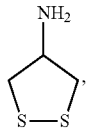

Formula E

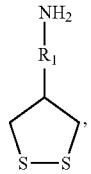

Formula F

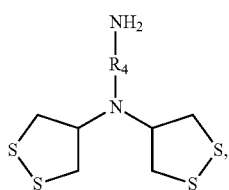

Formula G

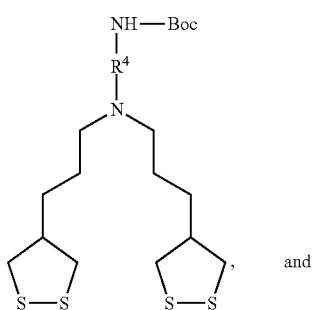

, and

Formula H

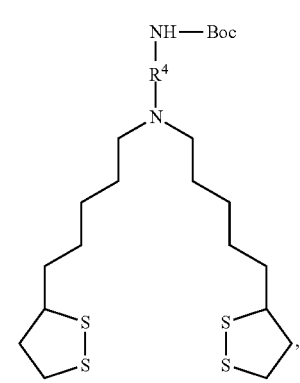

, wherein $R_1$ $R_4$ and $R_5$ are each independently selected from the group consisting of a branched or unbranched alkyl, aryl, cycloaliphatic and aralkyl group, is saturated or unsaturated, and optionally comprises hetero atoms;

a compound comprising a poly-α-glutamic acid-(1,2-dithiolane derivative) conjugate having Formula 239

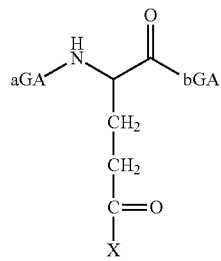

wherein aGA is a poly-α-glutamic acid polymer, and
X is a 1,2-dithiolane derivative selected from the group consisting of Formula A Formula A

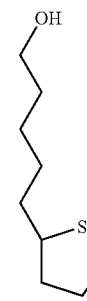

-continued

Formula B

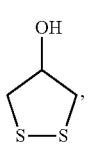

Formula C

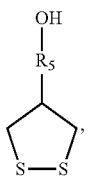

Formula D

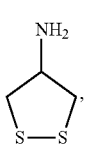

Formula E

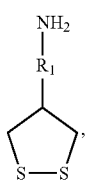

Formula F

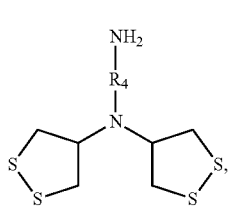

Formula G

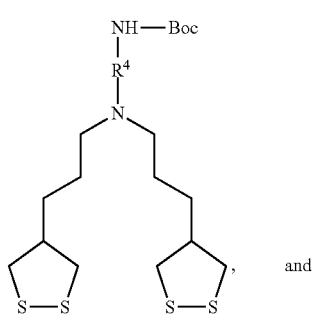

and

Formula H

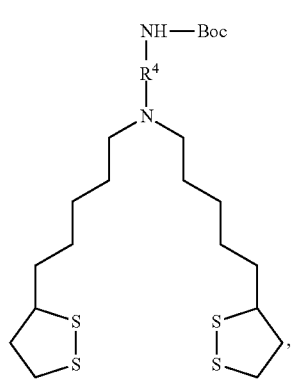

wherein $R_1$, $R_4$ and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the aGA;

a compound comprising a poly-γ-glutamic acid-(1,2-dithiolane derivative) conjugate having Formula 240

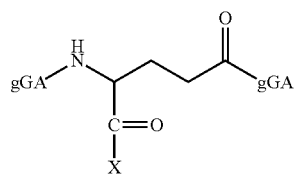

wherein gGA is a poly-γ-glutamic acid polymer, and

X is a 1,2-dithiolane derivative selected from the group consisting of Formula A Formula A

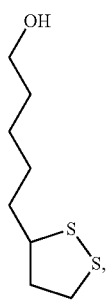

Formula B

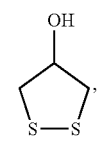

Formula C

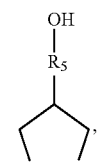

Formula D

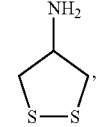

Formula E

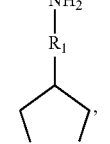

Formula F

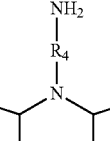

-continued

Formula G

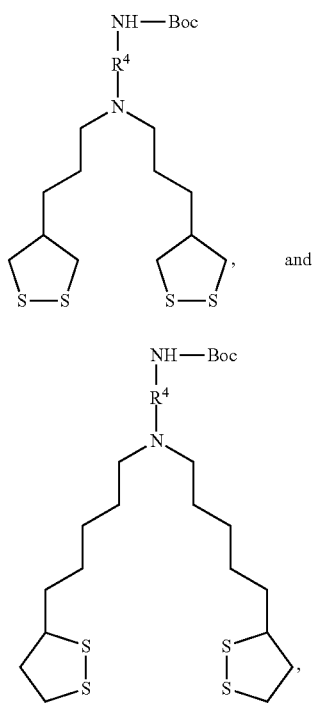

and

Formula H wherein $R_1$, $R_4$ and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the gGA;

a compound comprising a poly-β-malic acid acid-(1,2-dithiolane derivative) conjugate having

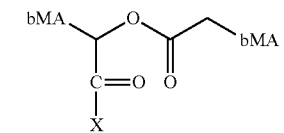

Formula 241 wherein bMA is a poly-β-malic acid acid polymer, and

X is a 1,2-dithiolane derivative selected from the group consisting of

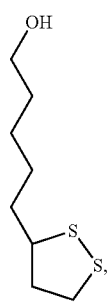

Formula A

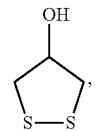

Formula B

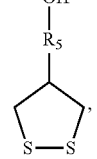

Formula C

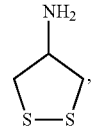

Formula D

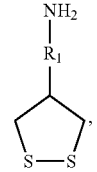

Formula E

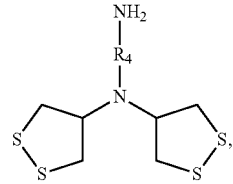

Formula F

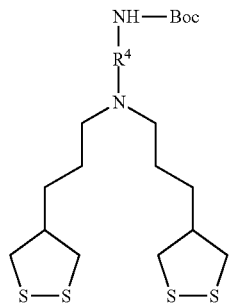

Formula G and

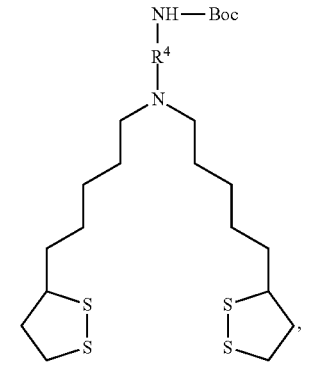

Formula H wherein $R_1$, $R_4$ and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the bMA;

a compound comprising a polyacrylic acid-(1,2-dithiolane derivative) conjugate having

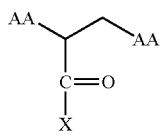

Formula 242 wherein AA is a polyacrylic acid polymer, and

X is a 1,2-dithiolane derivative selected from the group consisting of

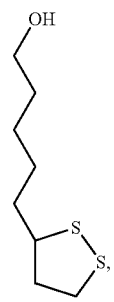

Formula A

Formula B

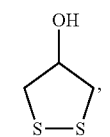

Formula C

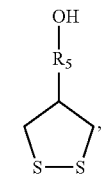

Formula D

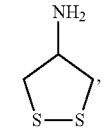

Formula E

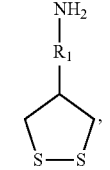

Formula F

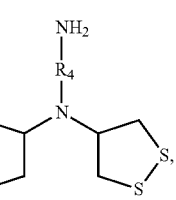

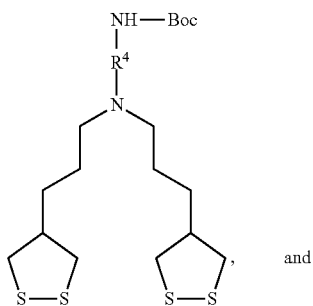

Formula G and

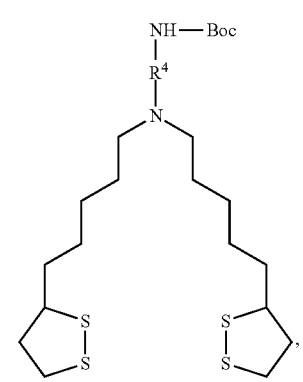

Formula H wherein $R_1$, $R_4$ and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the AA;

a compound comprising a polymethacrylic acid-(1,2-dithiolane derivative) conjugate having

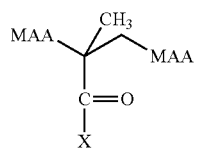

Formula 243 wherein MAA is a polymethacrylic acid polymer, and

X is a 1,2-dithiolane derivative selected from the group consisting of

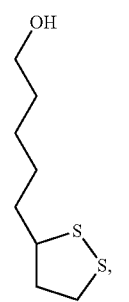

Formula A

-continued

Formula B

[structure: hydroxy-dithiolane]

Formula C

[structure: R5-substituted hydroxy-dithiolane]

Formula D

[structure: amino-dithiolane]

Formula E

[structure: R1-substituted amino-dithiolane]

Formula F

[structure: R4-N-linked bis-dithiolane with NH2]

Formula G

[structure: R4-N-linked bis-dithiolane with NH-Boc]

and

Formula H

[structure: R4-N-linked bis-dithiolane with NH-Boc, longer chains]

wherein $R_1$, $R_4$ and $R_5$ are each independently selected from the group consisting of a branched or unbranched alkyl, aryl, cycloaliphatic and aralkyl group, is saturated or unsaturated, optionally comprises hetero atoms, and linked via an ester or amide bond to the carbonyl group of a monomeric unit of the MAA;

a compound comprising a linear polyethyleneimine-(α-lipoic acid) conjugate having Formula 244

[structure: LPEI-N(LPEI)-C(=O)-chain-lipoic acid dithiolane]

wherein LPEI is a linear polyethyleneimine polymer and the α-lipoic acid is linked via an amide bond to the amine group of a monomeric unit of the LPEI;

a compound comprising a chitosan-(α-lipoic acid) conjugate having

Formula 245

[structure: chitosan monomer with CTS linkages and NH-C(=O)-chain-lipoic acid dithiolane]

wherein CTS is a chitosan polymer and the α-lipoic acid is linked via an amide bond to the amine group of a monomeric unit of the CTS;

a compound comprising a poly(amido amide)(PAMAM)-(α-lipoic acid) dendrimer conjugate wherein the α-lipoic acid is linked via an amide bond to the surface primary amine linker units of the PAMAM dendrimer;

a compound comprising a poly(amido amide)(PAMAM)-(α-lipolol) conjugate wherein α-lipoic acid is linked via an ester bond to the surface carboxylic acid linker units of the PAMAM dendrimer; and a compound comprising polysaccharide-(α-lipoic acid) conjugate in which α-lipoic acid is linked via ester bond to the hydroxyl group of a monomeric unit of polysaccharide;

wherein if the condition is cancer, the composition further comprises an antineoplastic agent and the antioxidant polymer increases the cytotoxicity of the antineoplastic agent.

* * * * *